(12) United States Patent
Reyes et al.

(10) Patent No.: US 6,229,005 B1
(45) Date of Patent: *May 8, 2001

(54) DNA SEQUENCES OF ENTERICALLY TRANSMITTED NON-A/NON-B HEPATITIS VIRAL AGENT

(75) Inventors: Gregory R. Reyes, Palo Alto; Patrice O. Yarbough, Union City, both of CA (US); Daniel W. Bradley, Lawrenceville; Krzysztof Z. Krawczynski, Norcross, both of GA (US); Albert W. Tam, San Francisco; Kirk E. Fry, Palo Alto, both of CA (US)

(73) Assignees: The United States of America as represented by the Department of Health and Human Services, Washington, DC (US); Genelabs Technologies, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/128,275

(22) Filed: Aug. 3, 1998

Related U.S. Application Data

(63) Continuation of application No. 08/279,823, filed on Jul. 25, 1994, now Pat. No. 5,789,559, which is a continuation of application No. 07/681,078, filed on Apr. 5, 1991, now abandoned, which is a continuation-in-part of application No. 07/505,888, filed on Apr. 5, 1990, now abandoned, which is a continuation-in-part of application No. 07/420,921, filed on Oct. 13, 1989, now abandoned, which is a continuation-in-part of application No. 07/367,486, filed on Jun. 16, 1989, now abandoned, which is a continuation-in-part of application No. 07/336,672, filed on Apr. 11, 1989, now abandoned, which is a continuation-in-part of application No. 07/208,997, filed on Jun. 17, 1988, now abandoned.

(51) Int. Cl.[7] .......................... C07H 21/04; G01N 33/00
(52) U.S. Cl. ................. 536/23.72; 536/24.3; 536/24.33; 436/94
(58) Field of Search .................................. 435/5, 6, 91.1, 435/91.2; 436/94; 536/23.1, 23.72, 24.3, 24.33

(56) References Cited

U.S. PATENT DOCUMENTS 5,789,559 * 8/1998 Reyes et al. ...................... 536/23.72

* cited by examiner

*Primary Examiner*—Bradley L. Sisson
(74) *Attorney, Agent, or Firm*—Joanne R. Petithory; Peter J. Dehlinger; Larry W. Thrower

(57) ABSTRACT

Viral proteins derived from an enterically transmitted non-A/non-B viral hepatitis agent (HEV) are disclosed. In one embodiment, the protein is immunologically reactive with antibodies present in individuals infected with the viral hepatitis agent. This protein is useful in a diagnostic method for detecting infection by the enterically transmitted agent. Specific epitopes have been identified that are reactive with sera of individual infected with different strains of HEV. Also disclosed are DNA probes derived from a cloned sequence of the viral agent. These probes are useful for identifying and sequencing the entire viral agent and for assaying the presence of the viral agent in an infected sample, by using probe-specific amplification of virus-derived DNA fragments.

6 Claims, 2 Drawing Sheets

```
                         SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
          (A) LENGTH: 1295 base pairs
          (B) TYPE: nucleic acid
          (C) STRANDEDNESS: double
          (D) TOPOLOGY: linear (ii) MOLECULE TYPE: DNA (iii) HYPOTHETICAL: NO (iv) ANTI-SENSE: NO (vi) ORIGINAL SOURCE:
          (C) INDIVIDUAL ISOLATE: 1.33 kb EcoRI insert of ET1.1,
              forward sequence (ix) FEATURE:
          (A) NAME/KEY: CDS
          (B) LOCATION: 1..1293

(ix) FEATURE:
          (A) NAME/KEY: CDS
          (B) LOCATION: 2..1294

(ix) FEATURE:
          (A) NAME/KEY: CDS
          (B) LOCATION: 3..1295

(xi) SEQUENCE DESCRIPTION: SEQ ID NO:1:

AGACCTGTCC CTGTTGCAGC TGTTCTACCA CCCTGCCCCG AGCTCGAACA GGGCCTTCTC      60

TACCTGCCCC AGGAGCTCAC CACCTGTGAT AGTGTCGTAA CATTTGAATT AACAGACATT     120
```

-continued

```
GTGCACTGCC GCATGGCCGC CCCGAGCCAG CGCAAGGCCG TGCTGTCCAC ACTCGTGGGC      180

CGCTACGGCG TCGCACAAA GCTCTACAAT GCTTCCCACT CTGATGTTCG CGACTCTCTC      240

GCCCGTTTTA TCCCGGCCAT TGGCCCCGTA CAGGTTACAA CTTGTGAATT GTACGAGCTA      300

GTGGAGGCCA TGGTCGAGAA GGGCCAGGAT GGCTCCGCCG TCCTTGAGCT TGATCTTTGC      360

AACCGTGACG TGTCCAGGAT CACCTTCTTC AGAAAGATT GTAACAAGTT CACCACAGGT      420

GAGACCATTG CCCATGGTAA AGTGGGCCAG GGCATCTCGG CCTGGAGCAA GACCTTCTGC      480

GCCCTCTTTG GCCCTTGGTT CCGCGCTATT GAGAAGGCTA TTCTGGCCCT GCTCCCTCAG      540

GGTGTGTTTT ACGGTGATGC CTTTGATGAC ACCGTCTTCT CGGCGGCTGT GGCCGCAGCA      600

AAGGCATCCA TGGTGTTTGA GAATGACTTT TCTGAGTTTG ACTCCACCCA GAATAACTTT      660

TCTCTGGGTC TAGAGTGTGC TATTATGGAG GAGTGTGGGA TGCCGCAGTG GCTCATCCGC      720

CTGTATCACC TTATAAGGTC TGCGTGGATC TTGCAGGCCC CGAAGGAGTC TCTGCGAGGG      780

TTTTGGAAGA ACACTCCGG TGAGCCCGGC ACTCTTCTAT GGAATACTGT CTGGAATATG      840

GCCGTTATTA CCCACTGTTA TGACTTCCGC GATTTTCAGG TGGCTGCCTT TAAAGGTGAT      900

GATTCGATAG TGCTTTGCAG TGAGTATCGT CAGAGTCCAG GAGCTGCTGT CCTGATCGCC      960

GGCTGTGGCT TGAAGTTGAA GGTAGATTTC CGCCCGATCG GTTTGTATGC AGGTGTTGTG     1020

GTGGCCCCCG GCCTTGGCGC GCTCCCTGAT GTTGTGCGCT TCGCCGGCCG GCTTACCGAG     1080

AAGAATTGGG GCCCTGGCCC TGAGCGGGCG GAGCAGCTCC GCCTCGCTGT TAGTGATTTC     1140

CTCCGCAAGC TCACGAATGT AGCTCAGATG TGTGTGGATG TTGTTTCCCG TGTTTATGGG     1200

GTTTCCCCTG GACTCGTTCA TAACCTGATT GGCATGCTAC AGGCTGTTGC TGATGGCAAG     1260

GCACATTTCA CTGAGTCAGT AAAACCAGTG CTCGA                              1295
```

(2) INFORMATION FOR SEQ ID NO:2:

(i) SEQUENCE CHARACTERISTICS:
        (A) LENGTH: 431 amino acids
        (B) TYPE: amino acid
        (D) TOPOLOGY: linear (ii) MOLECULE TYPE: protein (xi) SEQUENCE DESCRIPTION: SEQ ID NO:2:

```
Arg Pro Val Pro Val Ala Ala Val Leu Pro Pro Cys Pro Glu Leu Glu
 1               5                  10                  15

Gln Gly Leu Leu Tyr Leu Pro Gln Glu Leu Thr Thr Cys Asp Ser Val
             20                  25                  30

Val Thr Phe Glu Leu Thr Asp Ile Val His Cys Arg Met Ala Ala Pro
         35                  40                  45

Ser Gln Arg Lys Ala Val Leu Ser Thr Leu Val Gly Arg Tyr Gly Gly
     50                  55                  60

Arg Thr Lys Leu Tyr Asn Ala Ser His Ser Asp Val Arg Asp Ser Leu
 65                  70                  75                  80

Ala Arg Phe Ile Pro Ala Ile Gly Pro Val Gln Val Thr Thr Cys Glu
                 85                  90                  95

Leu Tyr Glu Leu Val Glu Ala Met Val Glu Lys Gly Gln Asp Gly Ser
            100                 105                 110

Ala Val Leu Glu Leu Asp Leu Cys Asn Arg Asp Val Ser Arg Ile Thr
        115                 120                 125

Phe Phe Gln Lys Asp Cys Asn Lys Phe Thr Thr Gly Glu Thr Ile Ala
    130                 135                 140
```

-continued

```
His Gly Lys Val Gly Gln Gly Ile Ser Ala Trp Ser Lys Thr Phe Cys
145                 150                 155                 160

Ala Leu Phe Gly Pro Trp Phe Arg Ala Ile Glu Lys Ala Ile Leu Ala
            165                 170                 175

Leu Leu Pro Gln Gly Val Phe Tyr Gly Asp Ala Phe Asp Asp Thr Val
            180                 185                 190

Phe Ser Ala Ala Val Ala Ala Ala Lys Ala Ser Met Val Phe Glu Asn
            195                 200                 205

Asp Phe Ser Glu Phe Asp Ser Thr Gln Asn Asn Phe Ser Leu Gly Leu
            210                 215                 220

Glu Cys Ala Ile Met Glu Glu Cys Gly Met Pro Gln Trp Leu Ile Arg
225                 230                 235                 240

Leu Tyr His Leu Ile Arg Ser Ala Trp Ile Leu Gln Ala Pro Lys Glu
            245                 250                 255

Ser Leu Arg Gly Phe Trp Lys Lys His Ser Gly Glu Pro Gly Thr Leu
            260                 265                 270

Leu Trp Asn Thr Val Trp Asn Met Ala Val Ile Thr His Cys Tyr Asp
            275                 280                 285

Phe Arg Asp Phe Gln Val Ala Ala Phe Lys Gly Asp Asp Ser Ile Val
            290                 295                 300

Leu Cys Ser Glu Tyr Arg Gln Ser Pro Gly Ala Ala Val Leu Ile Ala
305                 310                 315                 320

Gly Cys Gly Leu Lys Leu Lys Val Asp Phe Arg Pro Ile Gly Leu Tyr
            325                 330                 335

Ala Gly Val Val Val Ala Pro Gly Leu Gly Ala Leu Pro Asp Val Val
            340                 345                 350

Arg Phe Ala Gly Arg Leu Thr Glu Lys Asn Trp Gly Pro Gly Pro Glu
            355                 360                 365

Arg Ala Glu Gln Leu Arg Leu Ala Val Ser Asp Phe Leu Arg Lys Leu
            370                 375                 380

Thr Asn Val Ala Gln Met Cys Val Asp Val Val Ser Arg Val Tyr Gly
385                 390                 395                 400

Val Ser Pro Gly Leu Val His Asn Leu Ile Gly Met Leu Gln Ala Val
            405                 410                 415

Ala Asp Gly Lys Ala His Phe Thr Glu Ser Val Lys Pro Val Leu
            420                 425                 430
```

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: linker - top (5') sequence (xi) SEQUENCE DESCRIPTION: SEQ ID NO:3:

```
GGAATTCGCG GCCGCTCG                                               18
```

(2) INFORMATION FOR SEQ ID NO:4:

```
       (i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (iii) HYPOTHETICAL: NO (iv) ANTI-SENSE: NO (vi) ORIGINAL SOURCE:
           (C) INDIVIDUAL ISOLATE: linker - bottom (3') sequence (xi) SEQUENCE DESCRIPTION: SEQ ID NO:4:

CGAGCGGCCG CGAATTCCTT                                                    20

(2) INFORMATION FOR SEQ ID NO:5:

(i) SEQUENCE CHARACTERISTICS:
           (A) LENGTH: 1295 base pairs
           (B) TYPE: nucleic acid
           (C) STRANDEDNESS: double
           (D) TOPOLOGY: linear (ii) MOLECULE TYPE: DNA (iii) HYPOTHETICAL: NO (iv) ANTI-SENSE: NO (vi) ORIGINAL SOURCE:
           (C) INDIVIDUAL ISOLATE: 1.33 kb EcoRI insert of ET1.1,
               reverse sequence (xi) SEQUENCE DESCRIPTION: SEQ ID NO:5:

TCGAGCACTG GTTTTACTGA CTCAGTGAAA TGTGCCTTGC CATCAGCAAC AGCCTGTAGC         60

ATGCCAATCA GGTTATGAAC GAGTCCAGGG GAAACCCCAT AAACACGGGA ACAACATCC        120

ACACACATCT GAGCTACATT CGTGAGCTTG CGGAGGAAAT CACTAACAGC GAGGCGGAGC       180

TGCTCCGCCC GCTCAGGGCC AGGGCCCCAA TTCTTCTCGG TAAGCCGGCC GGCGAAGCGC       240

ACAACATCAG GGAGCGCGCC AAGGCCGGGG GCCACCACAA CACCTGCATA CAAACCGATC       300

GGGCGGAAAT CTACCTTCAA CTTCAAGCCA CAGCCGGCGA TCAGGACAGC AGCTCCTGGA       360

CTCTGACGAT ACTCACTGCA AAGCACTATC GAATCATCAC CTTTAAAGGC AGCCACCTGA       420

AAATCGCGGA AGTCATAACA GTGGGTAATA ACGGCCATAT TCCAGACAGT ATTCCATAGA       480

AGAGTGCCGG GCTCACCGGA GTGTTTCTTC CAAAACCCTC GCAGAGACTC CTTCGGGGCC       540

TGCAAGATCC ACGCAGACCT TATAAGGTGA TACAGGCGGA TGAGCCACTG CGGCATCCCA       600

CACTCCTCCA TAATAGCACA CTCTAGACCC AGAGAAAAGT TATTCTGGGT GGAGTCAAAC       660

TCAGAAAAGT CATTCTCAAA CACCATGGAT GCCTTTGCTG CGGCCACAGC CGCCGAGAAG       720

ACGGTGTCAT CAAAGGCATC ACCGTAAAAC ACACCCTGAG GGAGCAGGGC CAGAATAGCC       780

TTCTCAATAG CGCGGAACCA AGGGCCAAAG AGGGCGCAGA AGGTCTTGCT CCAGGCCGAG       840

ATGCCCTGGC CCACTTTACC ATGGGCAATG GTCTCACCTG TGGTGAACTT GTTACAATCT       900

TTCTGGAAGA AGGTGATCCT GGACACGTCA CGGTTGCAAA GATCAAGCTC AAGGACGGCG       960

GAGCCATCCT GGCCCTTCTC GACCATGGCC TCCACTAGCT CGTACAATTC ACAAGTTGTA      1020

ACCTGTACGG GGCCAATGGC CGGGATAAAA CGGGCGAGAG AGTCGCGAAC ATCAGAGTGG      1080

GAAGCATTGT AGAGCTTTGT GCGACCGCCG TAGCGCCCA CGAGTGTGGA CAGCACGGCC      1140

TTGCGCTGGC TCGGGCGGC CATGCGGCAG TGCACAATGT CTGTTAATTC AAATGTTACG      1200
```

-continued

```
ACACTATCAC AGGTGGTGAG CTCCTGGGGC AGGTAGAGAA GGCCCTGTTC GAGCTCGGGG    1260

CAGGGTGGTA GAACAGCTGC AACAGGGACA GGTCT                              1295
```

(2) INFORMATION FOR SEQ ID NO:6:

(i) SEQUENCE CHARACTERISTICS:
        (A) LENGTH: 7195 base pairs
        (B) TYPE: nucleic acid
        (C) STRANDEDNESS: double
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: HEV - Burma strain (ix) FEATURE:
        (A) NAME/KEY: CDS
        (B) LOCATION: 28..5106

(ix) FEATURE:
        (A) NAME/KEY: CDS
        (B) LOCATION: 5147..7126

(ix) FEATURE:
        (A) NAME/KEY: CDS
        (B) LOCATION: 5106..5474

(xi) SEQUENCE DESCRIPTION: SEQ ID NO:6:

```
AGGCAGACCA CATATGTGGT CGATGCCATG GAGGCCCATC AGTTTATTAA GGCTCCTGGC      60

ATCACTACTG CTATTGAGCA GGCTGCTCTA GCAGCGGCCA ACTCTGCCCT GGCGAATGCT     120

GTGGTAGTTA GGCCTTTTCT CTCTCACCAG CAGATTGAGA TCCTCATTAA CCTAATGCAA     180

CCTCGCCAGC TTGTTTTCCG CCCCGAGGTT TTCTGGAATC ATCCCATCCA GCGTGTCATC     240

CATAACGAGC TGGAGCTTTA CTGCCGCGCC CGCTCCGGCC GCTGTCTTGA AATTGGCGCC     300

CATCCCCGCT CAATAAATGA TAATCCTAAT GTGGTCCACC GCTGCTTCCT CCGCCCTGTT     360

GGGCGTGATG TTCAGCGCTG GTATACTGCT CCCACTCGCG GGCCGGCTGC TAATTGCCGG     420

CGTTCCGCGC TGCGCGGGCT TCCCGCTGCT GACCGCACTT ACTGCCTCGA CGGGTTTTCT     480

GGCTGTAACT TTCCCGCCGA GACTGGCATC GCCCTCTACT CCCTTCATGA TATGTCACCA     540

TCTGATGTCG CCGAGGCCAT GTTCCGCCAT GGTATGACGC GGCTCTATGC CGCCCTCCAT     600

CTTCCGCCTG AGGTCCTGCT GCCCCCTGGC ACATATCGCA CCGCATCGTA TTTGCTAATT     660

CATGACGGTA GGCGCGTTGT GGTGACGTAT GAGGGTGATA CTAGTGCTGG TTACAACCAC     720

GATGTCTCCA ACTTGCGCTC CTGGATTAGA ACCACCAAGG TTACCGGAGA CCATCCCCTC     780

GTTATCGAGC GGGTTAGGGC CATTGGCTGC ACTTTGTTC TCTTGCTCAC GGCAGCCCCG     840

GAGCCATCAC CTATGCCTTA TGTTCCTTAC CCCCGGTCTA CCGAGGTCTA TGTCCGATCG     900

ATCTTCGGCC CGGGTGGCAC CCCTTCCTTA TTCCCAACCT CATGCTCCAC TAAGTCGACC     960

TTCCATGCTG TCCCTGCCCA TATTTGGGAC CGTCTTATGC TGTTCGGGGC CACCTTGGAT    1020

GACCAAGCCT TTTGCTGCTC CCGTTTAATG ACCTACCTTC GCGGCATTAG CTACAAGGTC    1080

ACTGTTGGTA CCCTTGTGGC TAATGAAGGC TGGAATGCCT CTGAGGACGC CCTCACAGCT    1140

GTTATCACTG CCGCCTACCT TACCATTTGC CACCAGCGGT ATCTCCGCAC CCAGGCTATA    1200

TCCAAGGGGA TGCGTCGTCT GGAACGGGAG CATGCCCAGA AGTTTATAAC ACGCCTCTAC    1260
```

```
AGCTGGCTCT TCGAGAAGTC CGGCCGTGAT TACATCCCTG GCCGTCAGTT GGAGTTCTAC      1320

GCCCAGTGCA GGCGCTGGCT CTCCGCCGGC TTTCATCTTG ATCCACGGGT GTTGGTTTTT      1380

GACGAGTCGG CCCCCTGCCA TTGTAGGACC GCGATCCGTA AGGCGCTCTC AAAGTTTTGC      1440

TGCTTCATGA AGTGGCTTGG TCAGGAGTGC ACCTGCTTCC TTCAGCCTGC AGAAGGCGCC      1500

GTCGGCGACC AGGGTCATGA TAATGAAGCC TATGAGGGGT CCGATGTTGA CCCTGCTGAG      1560

TCCGCCATTA GTGACATATC TGGGTCCTAT GTCGTCCCTG GCACTGCCCT CCAACCGCTC      1620

TACCAGGCCC TCGATCTCCC CGCTGAGATT GTGGCTCGCG CGGGCCGGCT GACCGCCACA      1680

GTAAAGGTCT CCCAGGTCGA TGGGCGGATC GATTGCGAGA CCCTTCTTGG TAACAAAACC      1740

TTTCGCACGT CGTTCGTTGA CGGGGCGGTC TTAGAGACCA ATGGCCCAGA GCGCCACAAT      1800

CTCTCCTTCG ATGCCAGTCA GAGCACTATG GCCGCTGGCC CTTTCAGTCT CACCTATGCC      1860

GCCTCTGCAG CTGGGCTGGA GGTGCGCTAT GTTGCTGCCG GGCTTGACCA TCGGGCGGTT      1920

TTTGCCCCCG GTGTTTCACC CCGGTCAGCC CCCGGCGAGG TTACCGCCTT CTGCTCTGCC      1980

CTATACAGGT TTAACCGTGA GGCCCAGCGC CATTCGCTGA TCGGTAACTT ATGGTTCCAT      2040

CCTGAGGGAC TCATTGGCCT CTTCGCCCCG TTTTCGCCCG GCATGTTTG GGAGTCGGCT       2100

AATCCATTCT GTGGCGAGAG CACACTTTAC ACCCGTACTT GGTCGGAGGT TGATGCCGTC      2160

TCTAGTCCAG CCCGGCCTGA CTTAGGTTTT ATGTCTGAGC CTTCTATACC TAGTAGGGCC      2220

GCCACGCCTA CCCTGGCGGC CCCTCTACCC CCCCCTGCAC CGGACCCTTC CCCCCCTCCC      2280

TCTGCCCCGG CGCTTGCTGA GCCGGCTTCT GGCGCTACCG CCGGGGCCCC GGCCATAACT      2340

CACCAGACGG CCCCGGCACCG CCGCCTGCTC TTCACCTACC CGGATGGCTC TAAGGTATTC     2400

GCCGGCTCGC TGTTCGAGTC GACATGCACG TGGCTCGTTA ACGCGTCTAA TGTTGACCAC     2460

CGCCCTGGCG GCGGGCTTTG CCATGCATTT TACCAAAGGT ACCCCGCCTC CTTTGATGCT     2520

GCCTCTTTTG TGATGCGCGA CGGCGCGGCC GCGTACACAC TAACCCCCCG GCCAATAATT     2580

CACGCTGTCG CCCCTGATTA TAGGTTGGAA CATAACCCAA AGAGGCTTGA GGCTGCTTAT     2640

CGGGAAACTT GCTCCCGCCT CGGCACCGCT GCATACCCGC TCCTCGGGAC CGGCATATAC     2700

CAGGTGCCGA TCGGCCCCAG TTTTGACGCC TGGGAGCGGA ACCACCGCCC CGGGGATGAG     2760

TTGTACCTTC CTGAGCTTGC TGCCAGATGG TTTGAGGCCA ATAGGCCGAC CCGCCCGACT     2820

CTCACTATAA CTGAGGATGT TGCACGGACA GCGAATCTGG CCATCGAGCT TGACTCAGCC     2880

ACAGATGTCG GCCGGGCCTG TGCCGGCTGT CGGGTCACCC CCGGCGTTGT TCAGTACCAG     2940

TTTACTGCAG GTGTGCCTGG ATCCGGCAAG TCCCGCTCTA TCACCCAAGC CGATGTGGAC     3000

GTTGTCGTGG TCCCGACGCG TGAGTTGCGT AATGCCTGGC GCCGTCGCGG CTTTGCTGCT     3060

TTTACCCCGC ATACTGCCGC CAGAGTCACC CAGGGGCGCC GGGTTGTCAT TGATGAGGCT     3120

CCATCCCTCC CCCCTCACCT GCTGCTGCTC CACATGCAGC GGGCCGCCAC CGTCCACCTT     3180

CTTGGCGACC CGAACCAGAT CCCAGCCATC GACTTTGAGC ACGCTGGGCT CGTCCCCGCC     3240

ATCAGGCCCG ACTTAGGCCC CACCTCCTGG TGGCATGTTA CCCATCGCTG GCCTGCGGAT     3300

GTATGCGAGC TCATCCGTGG TGCATACCCC ATGATCCAGA CCACTAGCCG GGTTCTCCGT     3360

TCGTTGTTCT GGGGTGAGCC TGCCGTCGGG CAGAAACTAG TGTTCACCCA GGCGGCCAAG     3420

CCCGCCAACC CCGGCTCAGT GACGGTCCAC GAGGCGCAGG GCGCTACCTA CACGGAGACC     3480

ACTATTATTG CCACAGCAGA TGCCCGGGGC CTTATTCAGT CGTCTCGGGC TCATGCCATT     3540

GTTGCTCTGA CGCGCCACAC TGAGAAGTGC GTCATCATTG ACGCACCAGG CCTGCTTCGC     3600

GAGGTGGGCA TCTCCGATGC AATCGTTAAT AACTTTTTCC TCGCTGGTGG CGAAATTGGT     3660
```

```
CACCAGCGCC CATCAGTTAT TCCCCGTGGC AACCCTGACG CCAATGTTGA CACCCTGGCT    3720

GCCTTCCCGC CGTCTTGCCA GATTAGTGCC TTCCATCAGT TGGCTGAGGA GCTTGGCCAC    3780

AGACCTGTCC CTGTTGCAGC TGTTCTACCA CCCTGCCCCG AGCTCGAACA GGGCCTTCTC    3840

TACCTGCCCC AGGAGCTCAC CACCTGTGAT AGTGTCGTAA CATTTGAATT AACAGACATT    3900

GTGCACTGCC GCATGGCCGC CCCGAGCCAG CGCAAGGCCG TGCTGTCCAC ACTCGTGGGC    3960

CGCTACGGCG GTCGCACAAA GCTCTACAAT GCTTCCCACT CTGATGTTCG CGACTCTCTC    4020

GCCCGTTTTA TCCCGGCCAT TGGCCCCGTA CAGGTTACAA CTTGTGAATT GTACGAGCTA    4080

GTGGAGGCCA TGGTCGAGAA GGGCCAGGAT GGCTCCGCCG TCCTTGAGCT TGATCTTTGC    4140

AACCGTGACG TGTCCAGGAT CACCTTCTTC CAGAAAGATT GTAACAAGTT CACCACAGGT    4200

GAGACCATTG CCCATGGTAA AGTGGGCCAG GGCATCTCGG CCTGGAGCAA GACCTTCTGC    4260

GCCCTCTTTG GCCCTTGGTT CCGCGCTATT GAGAAGGCTA TTCTGGCCCT GCTCCCTCAG    4320

GGTGTGTTTT ACGGTGATGC CTTTGATGAC ACCGTCTTCT CGGCGGCTGT GGCCGCAGCA    4380

AAGGCATCCA TGGTGTTTGA GAATGACTTT TCTGAGTTTG ACTCCACCCA GAATAACTTT    4440

TCTCTGGGTC TAGAGTGTGC TATTATGGAG GAGTGTGGGA TGCCGCAGTG GCTCATCCGC    4500

CTGTATCACC TTATAAGGTC TGCGTGGATC TTGCAGGCCC CGAAGGAGTC TCTGCGAGGG    4560

TTTTGGAAGA AACACTCCGG TGAGCCCGGC ACTCTTCTAT GGAATACTGT CTGGAATATG    4620

GCCGTTATTA CCCACTGTTA TGACTTCCGC GATTTTCAGG TGGCTGCCTT TAAAGGTGAT    4680

GATTCGATAG TGCTTTGCAG TGAGTATCGT CAGAGTCCAG GAGCTGCTGT CCTGATCGCC    4740

GGCTGTGGCT TGAAGTTGAA GGTAGATTTC CGCCCGATCG GTTTGTATGC AGGTGTTGTG    4800

GTGGCCCCCG GCCTTGGCGC GCTCCCTGAT GTTGTGCGCT TCGCCGGCCG GCTTACCGAG    4860

AAGAATTGGG GCCCTGGCCC TGAGCGGGCG GAGCAGCTCC GCCTCGCTGT TAGTGATTTC    4920

CTCCGCAAGC TCACGAATGT AGCTCAGATG TGTGTGGATG TTGTTTCCCG TGTTTATGGG    4980

GTTTCCCCTG GACTCGTTCA TAACCTGATT GGCATGCTAC AGGCTGTTGC TGATGGCAAG    5040

GCACATTTCA CTGAGTCAGT AAAACCAGTG CTCGACTTGA CAAATTCAAT CTTGTGTCGG    5100

GTGGAATGAA TAACATGTCT TTTGCTGCGC CCATGGGTTC GCGACCATGC GCCCTCGGCC    5160

TATTTTGTTG CTGCTCCTCA TGTTTTTGCC TATGCTGCCC GCGCCACCGC CCGGTCAGCC    5220

GTCTGGCCGC CGTCGTGGGC GGCGCAGCGG CGGTTCCGGC GGTGGTTTCT GGGGTGACCG    5280

GGTTGATTCT CAGCCCTTCG CAATCCCCTA TATTCATCCA ACCAACCCCT TCGCCCCCGA    5340

TGTCACCGCT GCGGCCGGGG CTGGACCTCG TGTTCGCCAA CCCGCCCGAC CACTCGGCTC    5400

CGCTTGGCGT GACCAGGCCC AGCGCCCCGC CGTTGCCTCA CGTCGTAGAC CTACCACAGC    5460

TGGGGCCGCG CCGCTAACCG CGGTCGCTCC GGCCCATGAC ACCCCGCCAG TGCCTGATGT    5520

CGACTCCCGC GGCGCCATCT TGCGCCGGCA GTATAACCTA TCAACATCTC CCCTTACCTC    5580

TTCCGTGGCC ACCGGCACTA ACCTGGTTCT TTATGCCGCC CCTCTTAGTC CGCTTTTACC    5640

CCTTCAGGAC GGCACCAATA CCCATATAAT GGCCACGGAA GCTTCTAATT ATGCCCAGTA    5700

CCGGGTTGCC CGTGCCACAA TCCGTTACCG CCCGCTGGTC CCCAATGCTG TCGGCGGTTA    5760

CGCCATCTCC ATCTCATTCT GGCCACAGAC CACCACCACC CCGACGTCCG TTGATATGAA    5820

TTCAATAACC TCGACGGATG TTCGTATTTT AGTCCAGCCC GGCATAGCCT CTGAGCTTGT    5880

GATCCCAAGT GAGCGCCTAC ACTATCGTAA CCAAGGCTGG CGCTCCGTCG AGACCTCTGG    5940

GGTGGCTGAG GAGGAGGCTA CCTCTGGTCT TGTTATGCTT TGCATACATG GCTCACTCGT    6000
```

-continued

```
AAATTCCTAT ACTAATACAC CCTATACCGG TGCCCTCGGG CTGTTGGACT TTGCCCTTGA    6060

GCTTGAGTTT CGCAACCTTA CCCCCGGTAA CACCAATACG CGGGTCTCCC GTTATTCCAG    6120

CACTGCTCGC CACCGCCTTC GTCGCGGTGC GGACGGGACT GCCGAGCTCA CCACCACGGC    6180

TGCTACCCGC TTTATGAAGG ACCTCTATTT TACTAGTACT AATGGTGTCG GTGAGATCGG    6240

CCGCGGGATA GCCCTCACCC TGTTCAACCT TGCTGACACT CTGCTTGGCG GCCTGCCGAC    6300

AGAATTGATT TCGTCGGCTG GTGGCCAGCT GTTCTACTCC CGTCCCGTTG TCTCAGCCAA    6360

TGGCGAGCCG ACTGTTAAGT TGTATACATC TGTAGAGAAT GCTCAGCAGG ATAAGGGTAT    6420

TGCAATCCCG CATGACATTG ACCTCGGAGA ATCTCGTGTG GTTATTCAGG ATTATGATAA    6480

CCAACATGAA CAAGATCGGC CGACGCCTTC TCCAGCCCCA TCGCGCCCTT TCTCTGTCCT    6540

TCGAGCTAAT GATGTGCTTT GGCTCTCTCT CACCGCTGCC GAGTATGACC AGTCCACTTA    6600

TGGCTCTTCG ACTGGCCCAG TTTATGTTTC TGACTCTGTG ACCTTGGTTA ATGTTGCGAC    6660

CGGCGCGCAG GCCGTTGCCC GGTCGCTCGA TTGGACCAAG GTCACACTTG ACGGTCGCCC    6720

CCTCTCCACC ATCCAGCAGT ACTCGAAGAC CTTCTTTGTC CTGCCGCTCC GCGGTAAGCT    6780

CTCTTTCTGG GAGGCAGGCA CAACTAAAGC CGGGTACCCT TATAATTATA ACACCACTGC    6840

TAGCGACCAA CTGCTTGTCG AGAATGCCGC CGGGCACCGG GTCGCTATTT CCACTTACAC    6900

CACTAGCCTG GGTGCTGGTC CCGTCTCCAT TTCTGCGGTT GCCGTTTTAG CCCCCCACTC    6960

TGCGCTAGCA TTGCTTGAGG ATACCTTGGA CTACCCTGCC CGCGCCCATA CTTTTGATGA    7020

TTTCTGCCCA GAGTGCCGCC CCCTTGGCCT TCAGGGCTGC GCTTTCCAGT CTACTGTCGC    7080

TGAGCTTCAG CGCCTTAAGA TGAAGGTGGG TAAAACTCGG GAGTTGTAGT TTATTTGCTT    7140

GTGCCCCCCT TCTTTCTGTT GCTTATTTCT CATTTCTGCG TTCCGCGCTC CCTGA         7195
```

(2) INFORMATION FOR SEQ ID NO:7:

(i) SEQUENCE CHARACTERISTICS:
        (A) LENGTH: 1693 amino acids
        (B) TYPE: amino acid
        (D) TOPOLOGY: linear (ii) MOLECULE TYPE: protein (xi) SEQUENCE DESCRIPTION: SEQ ID NO:7:

```
Met Glu Ala His Gln Phe Ile Lys Ala Pro Gly Ile Thr Thr Ala Ile
  1               5                  10                  15

Glu Gln Ala Ala Leu Ala Ala Asn Ser Ala Leu Ala Asn Ala Val
             20                  25                  30

Val Val Arg Pro Phe Leu Ser His Gln Gln Ile Glu Ile Leu Ile Asn
         35                  40                  45

Leu Met Gln Pro Arg Gln Leu Val Phe Arg Pro Glu Val Phe Trp Asn
     50                  55                  60

His Pro Ile Gln Arg Val Ile His Asn Glu Leu Glu Leu Tyr Cys Arg
 65                  70                  75                  80

Ala Arg Ser Gly Arg Cys Leu Glu Ile Gly Ala His Pro Arg Ser Ile
                 85                  90                  95

Asn Asp Asn Pro Asn Val Val His Arg Cys Phe Leu Arg Pro Val Gly
            100                 105                 110

Arg Asp Val Gln Arg Trp Tyr Thr Ala Pro Thr Arg Gly Pro Ala Ala
        115                 120                 125

Asn Cys Arg Arg Ser Ala Leu Arg Gly Leu Pro Ala Ala Asp Arg Thr
    130                 135                 140
```

```
Tyr Cys Leu Asp Gly Phe Ser Gly Cys Asn Phe Pro Ala Glu Thr Gly
145                 150                 155                 160

Ile Ala Leu Tyr Ser Leu His Asp Met Ser Pro Ser Asp Val Ala Glu
            165                 170                 175

Ala Met Phe Arg His Gly Met Thr Arg Leu Tyr Ala Ala Leu His Leu
        180                 185                 190

Pro Pro Glu Val Leu Pro Pro Gly Thr Tyr Arg Thr Ala Ser Tyr
    195                 200                 205

Leu Leu Ile His Asp Gly Arg Arg Val Val Thr Tyr Glu Gly Asp
    210                 215                 220

Thr Ser Ala Gly Tyr Asn His Asp Val Ser Asn Leu Arg Ser Trp Ile
225                 230                 235                 240

Arg Thr Thr Lys Val Thr Gly Asp His Pro Leu Val Ile Glu Arg Val
            245                 250                 255

Arg Ala Ile Gly Cys His Phe Val Leu Leu Thr Ala Ala Pro Glu
            260                 265                 270

Pro Ser Pro Met Pro Tyr Val Pro Tyr Pro Arg Ser Thr Glu Val Tyr
        275                 280                 285

Val Arg Ser Ile Phe Gly Pro Gly Gly Thr Pro Ser Leu Phe Pro Thr
    290                 295                 300

Ser Cys Ser Thr Lys Ser Thr Phe His Ala Val Pro Ala His Ile Trp
305                 310                 315                 320

Asp Arg Leu Met Leu Phe Gly Ala Thr Leu Asp Asp Gln Ala Phe Cys
            325                 330                 335

Cys Ser Arg Leu Met Thr Tyr Leu Arg Gly Ile Ser Tyr Lys Val Thr
            340                 345                 350

Val Gly Thr Leu Val Ala Asn Glu Gly Trp Asn Ala Ser Glu Asp Ala
        355                 360                 365

Leu Thr Ala Val Ile Thr Ala Ala Tyr Leu Thr Ile Cys His Gln Arg
    370                 375                 380

Tyr Leu Arg Thr Gln Ala Ile Ser Lys Gly Met Arg Arg Leu Glu Arg
385                 390                 395                 400

Glu His Ala Gln Lys Phe Ile Thr Arg Leu Tyr Ser Trp Leu Phe Glu
            405                 410                 415

Lys Ser Gly Arg Asp Tyr Ile Pro Gly Arg Gln Leu Glu Phe Tyr Ala
            420                 425                 430

Gln Cys Arg Arg Trp Leu Ser Ala Gly Phe His Leu Asp Pro Arg Val
        435                 440                 445

Leu Val Phe Asp Glu Ser Ala Pro Cys His Cys Arg Thr Ala Ile Arg
    450                 455                 460

Lys Ala Leu Ser Lys Phe Cys Cys Phe Met Lys Trp Leu Gly Gln Glu
465                 470                 475                 480

Cys Thr Cys Phe Leu Gln Pro Ala Glu Gly Ala Val Gly Asp Gln Gly
            485                 490                 495

His Asp Asn Glu Ala Tyr Glu Gly Ser Asp Val Asp Pro Ala Glu Ser
            500                 505                 510

Ala Ile Ser Asp Ile Ser Gly Ser Tyr Val Val Pro Gly Thr Ala Leu
        515                 520                 525

Gln Pro Leu Tyr Gln Ala Leu Asp Leu Pro Ala Glu Ile Val Ala Arg
    530                 535                 540

Ala Gly Arg Leu Thr Ala Thr Val Lys Val Ser Gln Val Asp Gly Arg
545                 550                 555                 560

Ile Asp Cys Glu Thr Leu Leu Gly Asn Lys Thr Phe Arg Thr Ser Phe
```

-continued

```
                565                 570                 575
Val Asp Gly Ala Val Leu Glu Thr Asn Gly Pro Glu Arg His Asn Leu
            580                 585                 590
Ser Phe Asp Ala Ser Gln Ser Thr Met Ala Ala Gly Pro Phe Ser Leu
            595                 600                 605
Thr Tyr Ala Ala Ser Ala Ala Gly Leu Glu Val Arg Tyr Val Ala Ala
            610                 615                 620
Gly Leu Asp His Arg Ala Val Phe Ala Pro Gly Val Ser Pro Arg Ser
625                 630                 635                 640
Ala Pro Gly Glu Val Thr Ala Phe Cys Ser Ala Leu Tyr Arg Phe Asn
            645                 650                 655
Arg Glu Ala Gln Arg His Ser Leu Ile Gly Asn Leu Trp Phe His Pro
            660                 665                 670
Glu Gly Leu Ile Gly Leu Phe Ala Pro Phe Ser Pro Gly His Val Trp
            675                 680                 685
Glu Ser Ala Asn Pro Phe Cys Gly Glu Ser Thr Leu Tyr Thr Arg Thr
            690                 695                 700
Trp Ser Glu Val Asp Ala Val Ser Ser Pro Ala Arg Pro Asp Leu Gly
705                 710                 715                 720
Phe Met Ser Glu Pro Ser Ile Pro Ser Arg Ala Ala Thr Pro Thr Leu
            725                 730                 735
Ala Ala Pro Leu Pro Pro Ala Pro Asp Pro Ser Pro Pro Pro Ser
            740                 745                 750
Ala Pro Ala Leu Ala Glu Pro Ala Ser Gly Ala Thr Ala Gly Ala Pro
            755                 760                 765
Ala Ile Thr His Gln Thr Ala Arg His Arg Arg Leu Leu Phe Thr Tyr
770                 775                 780
Pro Asp Gly Ser Lys Val Phe Ala Gly Ser Leu Phe Glu Ser Thr Cys
785                 790                 795                 800
Thr Trp Leu Val Asn Ala Ser Asn Val Asp His Arg Pro Gly Gly Gly
            805                 810                 815
Leu Cys His Ala Phe Tyr Gln Arg Tyr Pro Ala Ser Phe Asp Ala Ala
            820                 825                 830
Ser Phe Val Met Arg Asp Gly Ala Ala Ala Tyr Thr Leu Thr Pro Arg
            835                 840                 845
Pro Ile Ile His Ala Val Ala Pro Asp Tyr Arg Leu Glu His Asn Pro
850                 855                 860
Lys Arg Leu Glu Ala Ala Tyr Arg Glu Thr Cys Ser Arg Leu Gly Thr
865                 870                 875                 880
Ala Ala Tyr Pro Leu Leu Gly Thr Gly Ile Tyr Gln Val Pro Ile Gly
            885                 890                 895
Pro Ser Phe Asp Ala Trp Glu Arg Asn His Arg Pro Gly Asp Glu Leu
            900                 905                 910
Tyr Leu Pro Glu Leu Ala Ala Arg Trp Phe Glu Ala Asn Arg Pro Thr
            915                 920                 925
Arg Pro Thr Leu Thr Ile Thr Glu Asp Val Ala Arg Thr Ala Asn Leu
            930                 935                 940
Ala Ile Glu Leu Asp Ser Ala Thr Asp Val Gly Arg Ala Cys Ala Gly
945                 950                 955                 960
Cys Arg Val Thr Pro Gly Val Val Gln Tyr Gln Phe Thr Ala Gly Val
            965                 970                 975
Pro Gly Ser Gly Lys Ser Arg Ser Ile Thr Gln Ala Asp Val Asp Val
            980                 985                 990
```

-continued

Val Val Val Pro Thr Arg Glu Leu Arg Asn Ala Trp Arg Arg Arg Gly
        995                 1000                1005

Phe Ala Ala Phe Thr Pro His Thr Ala Ala Arg Val Thr Gln Gly Arg
    1010                1015                1020

Arg Val Val Ile Asp Glu Ala Pro Ser Leu Pro Pro His Leu Leu Leu
1025                1030                1035                1040

Leu His Met Gln Arg Ala Ala Thr Val His Leu Leu Gly Asp Pro Asn
            1045                1050                1055

Gln Ile Pro Ala Ile Asp Phe Glu His Ala Gly Leu Val Pro Ala Ile
        1060                1065                1070

Arg Pro Asp Leu Gly Pro Thr Ser Trp Trp His Val Thr His Arg Trp
    1075                1080                1085

Pro Ala Asp Val Cys Glu Leu Ile Arg Gly Ala Tyr Pro Met Ile Gln
    1090                1095                1100

Thr Thr Ser Arg Val Leu Arg Ser Leu Phe Trp Gly Glu Pro Ala Val
1105                1110                1115                1120

Gly Gln Lys Leu Val Phe Thr Gln Ala Ala Lys Pro Ala Asn Pro Gly
            1125                1130                1135

Ser Val Thr Val His Glu Ala Gln Gly Ala Thr Tyr Thr Glu Thr Thr
        1140                1145                1150

Ile Ile Ala Thr Ala Asp Ala Arg Gly Leu Ile Gln Ser Ser Arg Ala
        1155                1160                1165

His Ala Ile Val Ala Leu Thr Arg His Thr Glu Lys Cys Val Ile Ile
    1170                1175                1180

Asp Ala Pro Gly Leu Leu Arg Glu Val Gly Ile Ser Asp Ala Ile Val
1185                1190                1195                1200

Asn Asn Phe Phe Leu Ala Gly Gly Glu Ile Gly His Gln Arg Pro Ser
            1205                1210                1215

Val Ile Pro Arg Gly Asn Pro Asp Ala Asn Val Asp Thr Leu Ala Ala
        1220                1225                1230

Phe Pro Pro Ser Cys Gln Ile Ser Ala Phe His Gln Leu Ala Glu Glu
        1235                1240                1245

Leu Gly His Arg Pro Val Pro Val Ala Ala Val Leu Pro Pro Cys Pro
    1250                1255                1260

Glu Leu Glu Gln Gly Leu Leu Tyr Leu Pro Gln Glu Leu Thr Thr Cys
1265                1270                1275                1280

Asp Ser Val Val Thr Phe Glu Leu Thr Asp Ile Val His Cys Arg Met
            1285                1290                1295

Ala Ala Pro Ser Gln Arg Lys Ala Val Leu Ser Thr Leu Val Gly Arg
        1300                1305                1310

Tyr Gly Gly Arg Thr Lys Leu Tyr Asn Ala Ser His Ser Asp Val Arg
        1315                1320                1325

Asp Ser Leu Ala Arg Phe Ile Pro Ala Ile Gly Pro Val Gln Val Thr
    1330                1335                1340

Thr Cys Glu Leu Tyr Glu Leu Val Glu Ala Met Val Glu Lys Gly Gln
1345                1350                1355                1360

Asp Gly Ser Ala Val Leu Glu Leu Asp Leu Cys Asn Arg Asp Val Ser
            1365                1370                1375

Arg Ile Thr Phe Phe Gln Lys Asp Cys Asn Lys Phe Thr Thr Gly Glu
        1380                1385                1390

Thr Ile Ala His Gly Lys Val Gly Gln Gly Ile Ser Ala Trp Ser Lys
        1395                1400                1405

-continued

```
Thr Phe Cys Ala Leu Phe Gly Pro Trp Phe Arg Ala Ile Glu Lys Ala
    1410                1415                1420

Ile Leu Ala Leu Leu Pro Gln Gly Val Phe Tyr Gly Asp Ala Phe Asp
1425                1430                1435                1440

Asp Thr Val Phe Ser Ala Ala Val Ala Ala Lys Ala Ser Met Val
                1445                1450                1455

Phe Glu Asn Asp Phe Ser Glu Phe Asp Ser Thr Gln Asn Asn Phe Ser
                1460                1465                1470

Leu Gly Leu Glu Cys Ala Ile Met Glu Glu Cys Gly Met Pro Gln Trp
            1475                1480                1485

Leu Ile Arg Leu Tyr His Leu Ile Arg Ser Ala Trp Ile Leu Gln Ala
            1490                1495                1500

Pro Lys Glu Ser Leu Arg Gly Phe Trp Lys Lys His Ser Gly Glu Pro
1505                1510                1515                1520

Gly Thr Leu Leu Trp Asn Thr Val Trp Asn Met Ala Val Ile Thr His
                1525                1530                1535

Cys Tyr Asp Phe Arg Asp Phe Gln Val Ala Ala Phe Lys Gly Asp Asp
            1540                1545                1550

Ser Ile Val Leu Cys Ser Glu Tyr Arg Gln Ser Pro Gly Ala Ala Val
            1555                1560                1565

Leu Ile Ala Gly Cys Gly Leu Lys Leu Lys Val Asp Phe Arg Pro Ile
1570                1575                1580

Gly Leu Tyr Ala Gly Val Val Val Ala Pro Gly Leu Gly Ala Leu Pro
1585                1590                1595                1600

Asp Val Val Arg Phe Ala Gly Arg Leu Thr Glu Lys Asn Trp Gly Pro
                1605                1610                1615

Gly Pro Glu Arg Ala Glu Gln Leu Arg Leu Ala Val Ser Asp Phe Leu
            1620                1625                1630

Arg Lys Leu Thr Asn Val Ala Gln Met Cys Val Asp Val Val Ser Arg
            1635                1640                1645

Val Tyr Gly Val Ser Pro Gly Leu Val His Asn Leu Ile Gly Met Leu
            1650                1655                1660

Gln Ala Val Ala Asp Gly Lys Ala His Phe Thr Glu Ser Val Lys Pro
1665                1670                1675                1680

Val Leu Asp Leu Thr Asn Ser Ile Leu Cys Arg Val Glu
                1685                1690

(2) INFORMATION FOR SEQ ID NO:8:

(i) SEQUENCE CHARACTERISTICS:
        (A) LENGTH: 660 amino acids
        (B) TYPE: amino acid
        (D) TOPOLOGY: linear (ii) MOLECULE TYPE: protein (xi) SEQUENCE DESCRIPTION: SEQ ID NO:8:

Met Arg Pro Arg Pro Ile Leu Leu Leu Leu Met Phe Leu Pro Met
    1                5                10                15

Leu Pro Ala Pro Pro Gly Gln Pro Ser Gly Arg Arg Gly Arg
                20                25                30

Arg Ser Gly Gly Ser Gly Gly Phe Trp Gly Asp Arg Val Asp Ser
            35                40                45

Gln Pro Phe Ala Ile Pro Tyr Ile His Pro Thr Asn Pro Phe Ala Pro
            50                55                60

Asp Val Thr Ala Ala Ala Gly Ala Gly Pro Arg Val Arg Gln Pro Ala
```

-continued

```
             65                  70                  75                  80
        Arg Pro Leu Gly Ser Ala Trp Arg Asp Gln Ala Gln Arg Pro Ala Val
                         85                  90                  95
        Ala Ser Arg Arg Arg Pro Thr Thr Ala Gly Ala Ala Pro Leu Thr Ala
                        100                 105                 110
        Val Ala Pro Ala His Asp Thr Pro Val Pro Asp Val Asp Ser Arg
                        115                 120                 125
        Gly Ala Ile Leu Arg Arg Gln Tyr Asn Leu Ser Thr Ser Pro Leu Thr
                        130                 135                 140
        Ser Ser Val Ala Thr Gly Thr Asn Leu Val Leu Tyr Ala Ala Pro Leu
        145                 150                 155                 160
        Ser Pro Leu Leu Pro Leu Gln Asp Gly Thr Asn Thr His Ile Met Ala
                        165                 170                 175
        Thr Glu Ala Ser Asn Tyr Ala Gln Tyr Arg Val Ala Arg Ala Thr Ile
                        180                 185                 190
        Arg Tyr Arg Pro Leu Val Pro Asn Ala Val Gly Gly Tyr Ala Ile Ser
                        195                 200                 205
        Ile Ser Phe Trp Pro Gln Thr Thr Thr Pro Thr Ser Val Asp Met
                        210                 215                 220
        Asn Ser Ile Thr Ser Thr Asp Val Arg Ile Leu Val Gln Pro Gly Ile
        225                 230                 235                 240
        Ala Ser Glu Leu Val Ile Pro Ser Glu Arg Leu His Tyr Arg Asn Gln
                        245                 250                 255
        Gly Trp Arg Ser Val Glu Thr Ser Gly Val Ala Glu Glu Ala Thr
                        260                 265                 270
        Ser Gly Leu Val Met Leu Cys Ile His Gly Ser Leu Val Asn Ser Tyr
                        275                 280                 285
        Thr Asn Thr Pro Tyr Thr Gly Ala Leu Gly Leu Leu Asp Phe Ala Leu
                        290                 295                 300
        Glu Leu Glu Phe Arg Asn Leu Thr Pro Gly Asn Thr Asn Thr Arg Val
        305                 310                 315                 320
        Ser Arg Tyr Ser Ser Thr Ala Arg His Arg Leu Arg Arg Gly Ala Asp
                        325                 330                 335
        Gly Thr Ala Glu Leu Thr Thr Thr Ala Ala Thr Arg Phe Met Lys Asp
                        340                 345                 350
        Leu Tyr Phe Thr Ser Thr Asn Gly Val Gly Glu Ile Gly Arg Gly Ile
                        355                 360                 365
        Ala Leu Thr Leu Phe Asn Leu Ala Asp Thr Leu Leu Gly Gly Leu Pro
                        370                 375                 380
        Thr Glu Leu Ile Ser Ser Ala Gly Gly Gln Leu Phe Tyr Ser Arg Pro
        385                 390                 395                 400
        Val Val Ser Ala Asn Gly Glu Pro Thr Val Lys Leu Tyr Thr Ser Val
                        405                 410                 415
        Glu Asn Ala Gln Gln Asp Lys Gly Ile Ala Ile Pro His Asp Ile Asp
                        420                 425                 430
        Leu Gly Glu Ser Arg Val Val Ile Gln Asp Tyr Asp Asn Gln His Glu
                        435                 440                 445
        Gln Asp Arg Pro Thr Pro Ser Pro Ala Pro Ser Arg Pro Phe Ser Val
                        450                 455                 460
        Leu Arg Ala Asn Asp Val Leu Trp Leu Ser Leu Thr Ala Ala Glu Tyr
        465                 470                 475                 480
        Asp Gln Ser Thr Tyr Gly Ser Ser Thr Gly Pro Val Tyr Val Ser Asp
                        485                 490                 495
```

```
Ser Val Thr Leu Val Asn Val Ala Thr Gly Ala Gln Ala Val Ala Arg
                500                 505                 510

Ser Leu Asp Trp Thr Lys Val Thr Leu Asp Gly Arg Pro Leu Ser Thr
            515                 520                 525

Ile Gln Gln Tyr Ser Lys Thr Phe Phe Val Leu Pro Leu Arg Gly Lys
        530                 535                 540

Leu Ser Phe Trp Glu Ala Gly Thr Thr Lys Ala Gly Tyr Pro Tyr Asn
545                 550                 555                 560

Tyr Asn Thr Thr Ala Ser Asp Gln Leu Leu Val Glu Asn Ala Ala Gly
                565                 570                 575

His Arg Val Ala Ile Ser Thr Tyr Thr Thr Ser Leu Gly Ala Gly Pro
            580                 585                 590

Val Ser Ile Ser Ala Val Ala Val Leu Ala Pro His Ser Ala Leu Ala
        595                 600                 605

Leu Leu Glu Asp Thr Leu Asp Tyr Pro Ala Arg Ala His Thr Phe Asp
610                 615                 620

Asp Phe Cys Pro Glu Cys Arg Pro Leu Gly Leu Gln Gly Cys Ala Phe
625                 630                 635                 640

Gln Ser Thr Val Ala Glu Leu Gln Arg Leu Lys Met Lys Val Gly Lys
                645                 650                 655

Thr Arg Glu Leu
            660

(2) INFORMATION FOR SEQ ID NO:9:

(i) SEQUENCE CHARACTERISTICS:
        (A) LENGTH: 123 amino acids
        (B) TYPE: amino acid
        (D) TOPOLOGY: linear (ii) MOLECULE TYPE: protein (xi) SEQUENCE DESCRIPTION: SEQ ID NO:9:

Met Asn Asn Met Ser Phe Ala Ala Pro Met Gly Ser Arg Pro Cys Ala
 1               5                  10                  15

Leu Gly Leu Phe Cys Cys Cys Ser Ser Cys Phe Cys Leu Cys Cys Pro
            20                  25                  30

Arg His Arg Pro Val Ser Arg Leu Ala Ala Val Val Gly Gly Ala Ala
        35                  40                  45

Ala Val Pro Ala Val Val Ser Gly Val Thr Gly Leu Ile Leu Ser Pro
50                  55                  60

Ser Gln Ser Pro Ile Phe Ile Gln Pro Thr Pro Ser Pro Pro Met Ser
65                  70                  75                  80

Pro Leu Arg Pro Gly Leu Asp Leu Val Phe Ala Asn Pro Pro Asp His
                85                  90                  95

Ser Ala Pro Leu Gly Val Thr Arg Pro Ser Ala Pro Pro Leu Pro His
            100                 105                 110

Val Val Asp Leu Pro Gln Leu Gly Pro Arg Arg
        115                 120

(2) INFORMATION FOR SEQ ID NO:10:

(i) SEQUENCE CHARACTERISTICS:
        (A) LENGTH: 7171 base pairs
        (B) TYPE: nucleic acid
        (C) STRANDEDNESS: double
        (D) TOPOLOGY: linear
```

(ii) MOLECULE TYPE: DNA (iii) HYPOTHETICAL: NO (iv) ANTI-SENSE: NO (vi) ORIGINAL SOURCE:
    (C) INDIVIDUAL ISOLATE: Composite Mexico strain (xi) SEQUENCE DESCRIPTION: SEQ ID NO:10:

| | | | | | |
|---|---|---|---|---|---|
| GCCATGGAGG | CCCACCAGTT | CATTAAGGCT | CCTGGCATCA | CTACTGCTAT | TGAGCAAGCA | 60 |
| GCTCTAGCAG | CGGCCAACTC | CGCCCTTGCG | AATGCTGTGG | TGGTCCGGCC | TTTCCTTTCC | 120 |
| CATCAGCAGG | TTGAGATCCT | TATAAATCTC | ATGCAACCTC | GGCAGCTGGT | GTTTCGTCCT | 180 |
| GAGGTTTTTT | GGAATCACCC | GATTCAACGT | GTTATACATA | ATGAGCTTGA | GCAGTATTGC | 240 |
| CGTGCTCGCT | CGGGTCGCTG | CCTTGAGATT | GGAGCCCACC | CACGCTCCAT | TAATGATAAT | 300 |
| CCTAATGTCC | TCCATCGCTG | CTTTCTCCAC | CCCGTCGGCC | GGGATGTTCA | GCGCTGGTAC | 360 |
| ACAGCCCCGA | CTAGGGGACC | TGCGGCGAAC | TGTCGCCGCT | CGGCACTTCG | TGGTCTGCCA | 420 |
| CCAGCCGACC | GCACTTACTG | TTTTGATGGC | TTTGCCGGCT | GCCGTTTTGC | CGCCGAGACT | 480 |
| GGTGTGGCTC | TCTATTCTCT | CCATGACTTG | CAGCCGGCTG | ATGTTGCCGA | GGCGATGGCT | 540 |
| CGCCACGGCA | TGACCCGCCT | TTATGCAGCT | TTCCACTTGC | CTCCAGAGGT | GCTCCTGCCT | 600 |
| CCTGGCACCT | ACCGGACATC | ATCCTACTTG | CTGATCCACG | ATGGTAAGCG | CGCGGTTGTC | 660 |
| ACTTATGAGG | GTGACACTAG | CGCCGGTTAC | AATCATGATG | TTGCCACCCT | CCGCACATGG | 720 |
| ATCAGGACAA | CTAAGGTTGT | GGGTGAACAC | CCTTTGGTGA | TCGAGCGGGT | GCGGGGTATT | 780 |
| GGCTGTCACT | TTGTGTTGTT | GATCACTGCG | GCCCCTGAGC | CCTCCCCGAT | GCCCTACGTT | 840 |
| CCTTACCCGC | GTTCGACGGA | GGTCTATGTC | CGGTCTATCT | TTGGGCCCGG | CGGGTCCCCG | 900 |
| TCGCTGTTCC | CGACCGCTTG | TGCTGTCAAG | TCCACTTTTC | ACGCCGTCCC | CACGCACATC | 960 |
| TGGGACCGTC | TCATGCTCTT | TGGGGCCACC | CTCGACGACC | AGGCCTTTTG | CTGCTCCAGG | 1020 |
| CTTATGACGT | ACCTTCGTGG | CATTAGCTAT | AAGGTAACTG | TGGGTGCCCT | GGTCGCTAAT | 1080 |
| GAAGGCTGGA | ATGCCACCGA | GGATGCGCTC | ACTGCAGTTA | TTACGGCGGC | TTACCTCACA | 1140 |
| ATATGTCATC | AGCGTTATTT | GCGGACCCAG | GCGATTTCTA | AGGGCATGCG | CCGGCTTGAG | 1200 |
| CTTGAACATG | CTCAGAAATT | TATTTCACGC | CTCTACAGCT | GGCTATTTGA | GAAGTCAGGT | 1260 |
| CGTGATTACA | TCCCAGGCCG | CCAGCTGCAG | TTCTACGCTC | AGTGCCGCCG | CTGGTTATCT | 1320 |
| GCCGGGTTCC | ATCTCGACCC | CCGCACCTTA | GTTTTTGATG | AGTCAGTGCC | TTGTAGCTGC | 1380 |
| CGAACCACCA | TCCGGCGGAT | CGCTGGAAAA | TTTTGCTGTT | TTATGAAGTG | GCTCGGTCAG | 1440 |
| GAGTGTTCTT | GTTTCCTCCA | GCCCGCCGAG | GGGCTGGCGG | GCGACCAAGG | TCATGACAAT | 1500 |
| GAGGCCTATG | AAGGCTCTGA | TGTTGATACT | GCTGAGCCTG | CCACCCTAGA | CATTACAGGC | 1560 |
| TCATACATCG | TGGATGGTCG | GTCTCTGCAA | ACTGTCTATC | AAGCTCTCGA | CCTGCCAGCT | 1620 |
| GACCTGGTAG | CTCGCGCAGC | CCGACTGTCT | GCTACAGTTA | CTGTTACTGA | AACCTCTGGC | 1680 |
| CGTCTGGATT | GCCAAACAAT | GATCGGCAAT | AAGACTTTTC | TCACTACCTT | TGTTGATGGG | 1740 |
| GCACGCCTTG | AGGTTAACGG | GCCTGAGCAG | CTTAACCTCT | CTTTTGACAG | CCAGCAGTGT | 1800 |
| AGTATGGCAG | CCGGCCCGTT | TTGCCTCACC | TATGCTGCCG | TAGATGGCGG | GCTGGAAGTT | 1860 |
| CATTTTTCCA | CCGCTGGCCT | CGAGAGCCGT | GTTGTTTTCC | CCCTGGTAA | TGCCCCGACT | 1920 |
| GCCCCGCCGA | GTGAGGTCAC | CGCCTTCTGC | TCAGCTCTTT | ATAGGCACAA | CCGGCAGAGC | 1980 |
| CAGCGCCAGT | CGGTTATTGG | TAGTTTGTGG | CTGCACCCTG | AAGGTTTGCT | CGGCCTGTTC | 2040 |

```
CCGCCCTTTT CACCCGGGCA TGAGTGGCGG TCTGCTAACC CATTTTGCGG CGAGAGCACG    2100

CTCTACACCC GCACTTGGTC CACAATTACA GACACACCCT TAACTGTCGG GCTAATTTCC    2160

GGTCATTTGG ATGCTGCTCC CCACTCGGGG GGGCCACCTG CTACTGCCAC AGGCCCTGCT    2220

GTAGGCTCGT CTGACTCTCC AGACCCTGAC CCGCTACCTG ATGTTACAGA TGGCTCACGC    2280

CCCTCTGGGG CCCGTCCGGC TGGCCCCAAC CCGAATGGCG TTCCGCAGCG CCGCTTACTA    2340

CACACCTACC CTGACGGCGC TAAGATCTAT GTCGGCTCCA TTTTCGAGTC TGAGTGCACC    2400

TGGCTTGTCA ACGCATCTAA CGCCGGCCAC CGCCCTGGTG GCGGGCTTTG TCATGCTTTT    2460

TTTCAGCGTT ACCCTGATTC GTTTGACGCC ACCAAGTTTG TGATGCGTGA TGGTCTTGCC    2520

GCGTATACCC TTACACCCCG GCCGATCATT CATGCGGTGG CCCCGGACTA TCGATTGGAA    2580

CATAACCCCA AGAGGCTCGA GGCTGCCTAC CGCGAGACTT GCGCCCGCCG AGGCACTGCT    2640

GCCTATCCAC TCTTAGGCGC TGGCATTTAC CAGGTGCCTG TTAGTTTGAG TTTTGATGCC    2700

TGGGAGCGGA ACCACCGCCC GTTTGACGAG CTTTACCTAA CAGAGCTGGC GGCTCGGTGG    2760

TTTGAATCCA ACCGCCCCGG TCAGCCCACG TTGAACATAA CTGAGGATAC CGCCCGTGCG    2820

GCCAACCTGG CCCTGGAGCT TGACTCCGGG AGTGAAGTAG GCCGCGCATG TGCCGGGTGT    2880

AAAGTCGAGC CTGGCGTTGT GCGGTATCAG TTTACAGCCG GTGTCCCCGG CTCTGGCAAG    2940

TCAAAGTCCG TGCAACAGGC GGATGTGGAT GTTGTTGTTG TGCCCACTCG CGAGCTTCGG    3000

AACGCTTGGC GGCGCCGGGG CTTTGCGGCA TTCACTCCGC ACACTGCGGC CCGTGTCACT    3060

AGCGGCCGTA GGGTTGTCAT TGATGAGGCC CCTTCGCTCC CCCCACACTT GCTGCTTTTA    3120

CATATGCAGC GTGCTGCATC TGTGCACCTC CTTGGGGACC CGAATCAGAT CCCCGCCATA    3180

GATTTTGAGC ACACCGGTCT GATTCCAGCA ATACGGCCGG AGTTGGTCCC GACTTCATGG    3240

TGGCATGTCA CCCACCGTTG CCCTGCAGAT GTCTGTGAGT TAGTCCGTGG TGCTTACCCT    3300

AAAATCCAGA CTACAAGTAA GGTGCTCCGT TCCCTTTTCT GGGGAGAGCC AGCTGTCGGC    3360

CAGAAGCTAG TGTTCACACA GGCTGCTAAG GCCGCGCACC CCGGATCTAT AACGGTCCAT    3420

GAGGCCCAGG GTGCCACTTT TACCACTACA ACTATAATTG CAACTGCAGA TGCCCGTGGC    3480

CTCATACAGT CCTCCCGGGC TCACGCTATA GTTGCTCTCA CTAGGCATAC TGAAAAATGT    3540

GTTATACTTG ACTCTCCCGG CCTGTTGCGT GAGGTGGGTA TCTCAGATGC CATTGTTAAT    3600

AATTTCTTCC TTTCGGGTGG CGAGGTTGGT CACCAGAGAC CATCGGTCAT TCCGCGAGGC    3660

AACCCTGACC GCAATGTTGA CGTGCTTGCG GCGTTTCCAC CTTCATGCCA AATAAGCGCC    3720

TTCCATCAGC TTGCTGAGGA GCTGGGCCAC CGGCCGGCGC CGGTGGCGGC TGTGCTACCT    3780

CCCTGCCCTG AGCTTGAGCA GGGCCTTCTC TATCTGCCAC AGGAGCTAGC CTCCTGTGAC    3840

AGTGTTGTGA CATTTGAGCT AACTGACATT GTGCACTGCC GCATGGCGGC CCCTAGCCAA    3900

AGGAAAGCTG TTTTGTCCAC GCTGGTAGGC CGGTATGGCA GACGCACAAG GCTTTATGAT    3960

GCGGGTCACA CCGATGTCCG CGCCTCCCTT GCGCGCTTTA TTCCCACTCT CGGGCGGGTT    4020

ACTGCCACCA CCTGTGAACT CTTTGAGCTT GTAGAGGCGA TGGTGGAGAA GGGCCAAGAC    4080

GGTTCAGCCG TCCTCGAGTT GGATTTGTGC AGCCGAGATG TCTCCCGCAT AACCTTTTTC    4140

CAGAAGGATT GTAACAAGTT CACGACCGGC GAGACAATTG CGCATGGCAA AGTCGGTCAG    4200

GGTATCTTCC GCTGGAGTAA GACGTTTTGT GCCCTGTTTG GCCCCTGGTT CCGTGCGATT    4260

GAGAAGGCTA TTCTATCCCT TTTACCACAA GCTGTGTTCT ACGGGATGCA TTATGACGAC    4320

TCAGTATTCT CTGCTGCCGT GGCTGGCGCC AGCCATGCCA TGGTGTTTGA AAATGATTTT    4380

TCTGAGTTTG ACTCGACTCA GAATAACTTT TCCCTAGGTC TTGAGTGCGC CATTATGGAA    4440
```

```
GAGTGTGGTA TGCCCCAGTG GCTTGTCAGG TTGTACCATG CCGTCCGGTC GGCGTGGATC   4500

CTGCAGGCCC CAAAAGAGTC TTTGAGAGGG TTCTGGAAGA AGCATTCTGG TGAGCCGGGC   4560

AGCTTGCTCT GGAATACGGT GTGGAACATG GCAATCATTG CCCATTGCTA TGAGTTCCGG   4620

GACCTCCAGG TTGCCGCCTT CAAGGGCGAC GACTCGGTCG TCCTCTGTAG TGAATACCGC   4680

CAGAGCCCAG GCGCCGGTTC GCTTATAGCA GGCTGTGGTT TGAAGTTGAA GGCTGACTTC   4740

CGGCCGATTG GGCTGTATGC CGGGGTTGTC GTCGCCCCGG GGCTCGGGGC CCTACCCGAT   4800

GTCGTTCGAT TCGCCGGACG GCTTTCGGAG AAGAACTGGG GGCCTGATCC GGAGCGGGCA   4860

GAGCAGCTCC GCCTCGCCGT GCAGGATTTC CTCCGTAGGT AACGAATGT GGCCCAGATT    4920

TGTGTTGAGG TGGTGTCTAG AGTTTACGGG GTTTCCCCGG GTCTGGTTCA TAACCTGATA   4980

GGCATGCTCC AGACTATTGG TGATGGTAAG GCGCATTTTA CAGAGTCTGT TAAGCCTATA   5040

CTTGACCTTA CACACTCAAT TATGCACCGG TCTGAATGAA TAACATGTGG TTTGCTGCGC   5100

CCATGGGTTC GCCACCATGC GCCCTAGGCC TCTTTTGCTG TTGTTCCTCT TGTTTCTGCC   5160

TATGTTGCCC GCGCCACCGA CCGGTCAGCC GTCTGGCCGC CGTCGTGGGC GGCGCAGCGG   5220

CGGTACCGGC GGTGGTTTCT GGGGTGACCG GGTTGATTCT CAGCCCTTCG CAATCCCCTA   5280

TATTCATCCA ACCAACCCCT TTGCCCCAGA CGTTGCCGCT GCGTCCGGGT CTGGACCTCG   5340

CCTTCGCCAA CCAGCCCGGC CACTTGGCTC CACTTGGCGA GATCAGGCCC AGCGCCCCTC   5400

CGCTGCCTCC CGTCGCCGAC CTGCCACAGC CGGGGCTGCG GCGCTGACGG CTGTGGCGCC   5460

TGCCCATGAC ACCTCACCCG TCCCGGACGT TGATTCTCGC GGTGCAATTC TACGCCGCCA   5520

GTATAATTTG TCTACTTCAC CCCTGACATC CTCTGTGGCC TCTGGCACTA ATTTAGTCCT   5580

GTATGCAGCC CCCCTTAATC CGCCTCTGCC GCTGCAGGAC GGTACTAATA CTCACATTAT   5640

GGCCACAGAG GCCTCCAATT ATGCACAGTA CCGGGTTGCC CGCGCTACTA TCCGTTACCG   5700

GCCCCTAGTG CCTAATGCAG TTGGAGGCTA TGCTATATCC ATTTCTTTCT GGCCTCAAAC   5760

AACCACAACC CCTACATCTG TTGACATGAA TTCCATTACT TCCACTGATG TCAGGATTCT   5820

TGTTCAACCT GGCATAGCAT CTGAATTGGT CATCCCAAGC GAGCGCCTTC ACTACCGCAA   5880

TCAAGGTTGG CGCTCGGTTG AGACATCTGG TGTTGCTGAG GAGGAAGCCA CCTCCGGTCT   5940

TGTCATGTTA TGCATACATG GCTCTCCAGT TAACTCCTAT ACCAATACCC CTTATACCGG   6000

TGCCCTTGGC TTACTGGACT TTGCCTTAGA GCTTGAGTTT CGCAATCTCA CCACCTGTAA   6060

CACCAATACA CGTGTGTCCC GTTACTCCAG CACTGCTCGT CACTCCGCCC GAGGGGCCGA   6120

CGGGACTGCG GAGCTGACCA CAACTGCAGC CACCAGGTTC ATGAAAGATC TCCACTTTAC   6180

CGGCCTTAAT GGGGTAGGTG AAGTCGGCCG CGGGATAGCT CTAACATTAC TTAACCTTGC   6240

TGACACGCTC CTCGGCGGGC TCCCGACAGA ATTAATTTCG TCGGCTGGCG GGCAACTGTT   6300

TTATTCCCGC CCGGTTGTCT CAGCCAATGG CGAGCCAACC GTGAAGCTCT ATACATCAGT   6360

GGAGAATGCT CAGCAGGATA AGGGTGTTGC TATCCCCCAC GATATCGATC TTGGTGATTC   6420

GCGTGTGGTC ATTCAGGATT ATGACAACCA GCATGAGCAG GATCGGCCCA CCCCGTCGCC   6480

TGCGCCATCT CGGCCTTTTT CTGTTCTCCG AGCAAATGAT GTACTTTGGC TGTCCCTCAC   6540

TGCAGCCGAG TATGACCAGT CCACTTACGG GTCGTCAACT GGCCCGGTTT ATATCTCGGA   6600

CAGCGTGACT TTGGTGAATG TTGCGACTGG CGCGCAGGCC GTAGCCCGAT CGCTTGACTG   6660

GTCCAAAGTC ACCCTCGACG GGCGGCCCCT CCCGACTGTT GAGCAATATT CCAAGACATT   6720

CTTTGTGCTC CCCCTTCGTG GCAAGCTCTC CTTTTGGGAG GCCGGCACAA CAAAAGCAGG   6780
```

```
TTATCCTTAT AATTATAATA CTACTGCTAG TGACCAGATT CTGATTGAAA ATGCTGCCGG        6840

CCATCGGGTC GCCATTTCAA CCTATACCAC CAGGCTTGGG GCCGGTCCGG TCGCCATTTC        6900

TGCGGCCGCG GTTTTGGCTC CACGCTCCGC CCTGGCTCTG CTGGAGGATA CTTTTGATTA        6960

TCCGGGGCGG GCGCACACAT TTGATGACTT CTGCCCTGAA TGCCGCGCTT TAGGCCTCCA        7020

GGGTTGTGCT TTCCAGTCAA CTGTCGCTGA GCTCCAGCGC CTTAAAGTTA AGGTGGGTAA        7080

AACTCGGGAG TTGTAGTTTA TTTGGCTGTG CCCACCTACT TATATCTGCT GATTTCCTTT        7140

ATTTCCTTTT TCTCGGTCCC GCGCTCCCTG A                                      7171

(2) INFORMATION FOR SEQ ID NO:11:

(i) SEQUENCE CHARACTERISTICS:
        (A) LENGTH: 1575 base pairs
        (B) TYPE: nucleic acid
        (C) STRANDEDNESS: double
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: T: Mexican strain (xi) SEQUENCE DESCRIPTION: SEQ ID NO:11:

GTTGCGTGAG GTGGGTATCT CAGATGCCAT TGTTAATAAT TTCTTCCTTT CGGGTGGCGA          60

GGTTGGTCAC CAGAGACCAT CGGTCATTCC GCGAGGCAAC CCTGACCGCA ATGTTGACGT         120

GCTTGCGGCG TTTCCACCTT CATGCCAAAT AAGCGCCTTC CATCAGCTTG CTGAGGAGCT         180

GGGCCACCGG CCGGCGCCGG TGGCGGCTGT GCTACCTCCC TGCCCTGAGC TTGAGCAGGG         240

CCTTCTCTAT CTGCCACAGG AGCTAGCCTC CTGTGACAGT GTTGTGACAT TTGAGCTAAC         300

TGACATTGTG CACTGCCGCA TGGCGGCCCC TAGCCAAAGG AAAGCTGTTT TGTCCACGCT         360

GGTAGGCCGG TATGGCAGAC GCACAAGGCT TTATGATGCG GGTCACACCG ATGTCCGCGC         420

CTCCCTTGCG CGCTTTATTC CCACTCTCGG GCGGGTTACT GCCACCACCT GTGAACTCTT         480

TGAGCTTGTA GAGGCGATGG TGGAGAAGGG CCAAGACGGT TCAGCCGTCC TCGAGTTGGA         540

TTTGTGCAGC CGAGATGTCT CCCGCATAAC CTTTTTCCAG AAGGATTGTA ACAAGTTCAC         600

GACCGGCGAG ACAATTGCGC ATGGCAAAGT CGGTCAGGGT ATCTTCCGCT GGAGTAAGAC         660

CTTTTGTGCC CTGTTTGGCC CCTGGTTCCG TGCGATTGAG AAGGCTATTC TATCCCTTTT         720

ACCACAAGCT GTGTTCTACG GGGATGCTTA TGACGACTCA GTATTCTCTG CTGCCGTGGC         780

TGGCGCCAGC CATGCCATGG TGTTTGAAAA TGATTTTTCT GAGTTTGACT CGACTCAGAA         840

TAACTTTTCC CTAGGTCTTG AGTGCGCCAT TATGGAAGAG TGTGGTATGC CCCAGTGGCT         900

TGTCAGGTTG TACCATGCCG TCCGGTCGGC GTGGATCCTG CAGGCCCCAA AAGAGTCTTT         960

GAGAGGGTTC TGGAAGAAGC ATTCTGGTGA GCCGGGCACG TTGCTCTGGA ATACGGTGTG        1020

GAACATGGCA ATCATTGCCC ATTGCTATGA GTTCCGGGAC CTCCAGGTTG CCGCCTTCAA        1080

GGGCGACGAC TCGGTCGTCC TCTGTAGTGA ATACCGCCAG AGCCCAGGCG CCGGTTCGCT        1140

TATAGCAGGC TGTGGTTTGA AGTTGAAGGC TGACTTCCGG CCGATTGGGC TGTATGCCGG        1200

GGTTGTCGTC GCCCCGGGGC TCGGGCCCCT ACCCGATGTC GTTCGATTCG CCGGACGGCT        1260

TTCGGAGAAG AACTGGGGGC CTGATCCGGA GCGGGCAGAG CAGCTCCGCC TCGCCGTGCA        1320

GGATTTCCTC CGTAGGTTAA CGAATGTGGC CCAGATTTGT GTTGAGGTGG TGTCTAGAGT        1380
```

-continued

```
TTACGGGGTT TCCCCGGGTC TGGTTCATAA CCTGATAGGC ATGCTCCAGA CTATTGGTGA      1440

TGGTAAGGCG CATTTTACAG AGTCTGTTAA GCCTATACTT GACCTTACAC ACTCAATTAT      1500

GCACCGGTCT GAATGAATAA CATGTGGTTT GCTGCGCCCA TGGGTTCGCC ACCATGCGCC      1560

CTAGGCCTCT TTTGC                                                      1575
```

(2) INFORMATION FOR SEQ ID NO:12:

(i) SEQUENCE CHARACTERISTICS:
        (A) LENGTH: 874 base pairs
        (B) TYPE: nucleic acid
        (C) STRANDEDNESS: double
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Tashkent strain (xi) SEQUENCE DESCRIPTION: SEQ ID NO:12:

```
CGGGCCCCGT ACAGGTCACA ACCTGTGAGT TGTACGAGCT AGTGGAGGCC ATGGTCGAGA        60

AAGGCCAGGA TGGCTCCGCC GTCCTTGAGC TCGATCTCTG CAACCGTGAC GTGTCCAGGA       120

TCACCTTTTT CCAGAAAGAT TGCAATAAGT TCACCACGGG AGAGACCATC GCCCATGGTA       180

AAGTGGGCCA GGGCATTTCG GCCTGGAGTA AGACCTTCTG TGCCCTTTTC GGCCCCTGGT       240

TCCGTGCTAT TGAGAAGGCT ATTCTGGCCC TGCTCCCTCA GGGTGTGTTT TATGGGGATG       300

CCTTTGATGA CACCGTCTTC TCGGCGCGTG TGGCCGCAGC AAAGGCGTCC ATGGTGTTTG       360

AGAATGACTT TTCTGAGTTT GACTCCACCC AGAATAATTT TTCCCTGGGC CTAGAGTGTG       420

CTATTATGGA GAAGTGTGGG ATGCCGAAGT GGCTCATCCG CTTGTACCAC CTTATAAGGT       480

CTGCGTGGAT CCTGCAGGCC CCGAAGGAGT CCCTGCGAGG GTGTTGGAAG AAACACTCCG       540

GTGAGCCCGG CACTCTTCTA TGGAATACTG TCTGGAACAT GGCCGTTATC ACCCATTGTT       600

ACGATTTCCG CGATTTGCAG GTGGCTGCCT TTAAAGGTGA TGATTCGATA GTGCTTTGCA       660

GTGAGTACCG TCAGAGTCCA GGGGCTGCTG TCCTGATTGC TGGCTGTGGC TTAAAGCTGA       720

AGGTGGGTTT CCGTCCGATT GGTTTGTATG CAGGTGTTGT GGTGACCCCC GGCCTTGGCG       780

CGCTTCCCGA CGTCGTGCGC TTGTCCGGCC GGCTTACTGA GAAGAATTGG GGCCCTGGCC       840

CTGAGCGGGC GGAGCAGCTC CGCCTTGCTG TGCG                                  874
```

(2) INFORMATION FOR SEQ ID NO:13:

(i) SEQUENCE CHARACTERISTICS:
        (A) LENGTH: 449 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: Clone 406.4-2 cDNA (ix) FEATURE:
        (A) NAME/KEY: CDS (B) LOCATION: 2..100

(xi) SEQUENCE DESCRIPTION: SEQ ID NO:13:

C GCC AAC CAG CCC GGC CAC TTG GCT CCA CTT GGC GAG ATC AGG CCC       46
  Ala Asn Gln Pro Gly His Leu Ala Pro Leu Gly Glu Ile Arg Pro
  1               5                  10                  15

AGC GCC CCT CCG CTG CCT CCC GTC GCC GAC CTG CCA CAG CCG GGG CTG     94
Ser Ala Pro Pro Leu Pro Pro Val Ala Asp Leu Pro Gln Pro Gly Leu
                20                  25                  30

CGG CGC TGACGGCTGT GGCGCCTGCC CATGACACCT CACCCGTCCC GGACGTTGAT     150
Arg Arg

TCTCGCGGTG CAATTCTACG CCGCCAGTAT AATTTGTCTA CTTCACCCCT GACATCCTCT  210

GTGGCCTCTG GCACTAATTT AGTCCTGTAT GCAGCCCCCC TTAATCCGCC TCTGCCGCTG  270

CAGGACGGTA CTAATACTCA CATTATGGCC ACAGAGGCCT CCAATTATGC ACAGTACCGG  330

GTTGCCCGCG CTACTATCCG TTACCGGCCC CTAGTGCCTA ATGCAGTTGG AGGCTATGCT  390

ATATCCATTT CTTTCTGGCC TCAAACAACC ACAACCCCTA CATCTGTTGA CATGAATTC   449

(2) INFORMATION FOR SEQ ID NO:14:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO:14:

Ala Asn Gln Pro Gly His Leu Ala Pro Leu Gly Glu Ile Arg Pro Ser
1               5                  10                  15

Ala Pro Pro Leu Pro Pro Val Ala Asp Leu Pro Gln Pro Gly Leu Arg
            20                  25                  30

Arg (2) INFORMATION FOR SEQ ID NO:15:

(i) SEQUENCE CHARACTERISTICS:
        (A) LENGTH: 130 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: Clone 406.3-2

(ix) FEATURE:
        (A) NAME/KEY: CDS
        (B) LOCATION: 5..130

(xi) SEQUENCE DESCRIPTION: SEQ ID NO:15:

GGAT ACT TTT GAT TAT CCG GGG CGG GCG CAC ACA TTT GAT GAC TTC TGC   49
     Thr Phe Asp Tyr Pro Gly Arg Ala His Thr Phe Asp Asp Phe Cys
     1               5                  10                  15

CCT GAA TGC CGC GCT TTA GGC CTC CAG GGT TGT GCT TTC CAG TCA ACT    97
Pro Glu Cys Arg Ala Leu Gly Leu Gln Gly Cys Ala Phe Gln Ser Thr
                20                  25                  30

GTC GCT GAG CTC CAG CGC CTT AAA GTT AAG GTT                       130
Val Ala Glu Leu Gln Arg Leu Lys Val Lys Val

```
                          35                  40

(2) INFORMATION FOR SEQ ID NO:16:

(i) SEQUENCE CHARACTERISTICS:
        (A) LENGTH: 42 amino acids
        (B) TYPE: amino acid
        (D) TOPOLOGY: linear (ii) MOLECULE TYPE: protein (xi) SEQUENCE DESCRIPTION: SEQ ID NO:16:

Thr Phe Asp Tyr Pro Gly Arg Ala His Thr Phe Asp Phe Cys Pro
  1               5                  10                  15

Glu Cys Arg Ala Leu Gly Leu Gln Gly Cys Ala Phe Gln Ser Thr Val
                 20                  25                  30

Ala Glu Leu Gln Arg Leu Lys Val Lys Val
             35                  40

(2) INFORMATION FOR SEQ ID NO:17:

(i) SEQUENCE CHARACTERISTICS:
        (A) LENGTH: 33 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (vi) ORIGINAL SOURCE:
         (C) INDIVIDUAL ISOLATE: 406.4-2 epitope - Mexican strain (xi) SEQUENCE DESCRIPTION: SEQ ID NO:17:

Ala Asn Gln Pro Gly His Leu Ala Pro Leu Gly Glu Ile Arg Pro Ser
  1               5                  10                  15

Ala Pro Pro Leu Pro Pro Val Ala Asp Leu Pro Gln Pro Gly Leu Arg
                 20                  25                  30

Arg (2) INFORMATION FOR SEQ ID NO:18:

(i) SEQUENCE CHARACTERISTICS:
        (A) LENGTH: 33 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (vi) ORIGINAL SOURCE:
         (C) INDIVIDUAL ISOLATE: 406.4-2 epitope - Burma strain (xi) SEQUENCE DESCRIPTION: SEQ ID NO:18:

Ala Asn Pro Pro Asp His Ser Ala Pro Leu Gly Val Thr Arg Pro Ser
  1               5                  10                  15

Ala Pro Pro Leu Pro His Val Val Asp Leu Pro Gln Leu Gly Pro Arg
                 20                  25                  30

Arg
```

-continued

```
(2) INFORMATION FOR SEQ ID NO:19:

(i) SEQUENCE CHARACTERISTICS:
          (A) LENGTH: 42 amino acids
          (B) TYPE: amino acid
          (C) STRANDEDNESS: single
          (D) TOPOLOGY: unknown (ii) MOLECULE TYPE: peptide (iii) HYPOTHETICAL: NO (iv) ANTI-SENSE: NO (vi) ORIGINAL SOURCE:
          (C) INDIVIDUAL ISOLATE: 406.3-2 epitope - Mexican strain (xi) SEQUENCE DESCRIPTION: SEQ ID NO:19:

Thr Phe Asp Tyr Pro Gly Arg Ala His Thr Phe Asp Asp Phe Cys Pro
1               5                   10                  15

Glu Cys Arg Ala Leu Gly Leu Gln Gly Cys Ala Phe Gln Ser Thr Val
            20                  25                  30

Ala Glu Leu Gln Arg Leu Lys Val Lys Val
        35                  40

(2) INFORMATION FOR SEQ ID NO:20:

(i) SEQUENCE CHARACTERISTICS:
          (A) LENGTH: 42 amino acids
          (B) TYPE: amino acid
          (C) STRANDEDNESS: single
          (D) TOPOLOGY: unknown (ii) MOLECULE TYPE: peptide (iii) HYPOTHETICAL: NO (iv) ANTI-SENSE: NO (vi) ORIGINAL SOURCE:
          (C) INDIVIDUAL ISOLATE: 406.3-2 epitope - Burma strain (xi) SEQUENCE DESCRIPTION: SEQ ID NO:20:

Thr Leu Asp Tyr Pro Ala Arg Ala His Thr Phe Asp Asp Phe Cys Pro
1               5                   10                  15

Glu Cys Arg Pro Leu Gly Leu Gln Gly Cys Ala Phe Gln Ser Thr Val
            20                  25                  30

Ala Glu Leu Gln Arg Leu Lys Met Lys Val
        35                  40
```

DNA SEQUENCES OF ENTERICALLY TRANSMITTED NON-A/NON-B HEPATITIS VIRAL AGENT

CROSS-REFERENCE TO RELATED APPLICATIONS

This application is a continuation of U.S. application Ser. No. 08/279,823, filed Jul. 25, 1994, now U.S. Pat. No. 5,789,559 which is a continuation of U.S. application Ser. No. 07/681,078, filed Apr. 5, 1991, now abandoned, which is a continuation-in-part of U.S. application Ser. No.07/505, 888, filed Apr. 5, 1990, now abandoned, which is a continuation-in-part of U.S. application Ser. No. 07/420, 921, filed Oct. 13, 1989, now abandoned, which is a continuation-in-part of U.S. application Ser. No. 07/367, 486, filed Jun. 16, 1989, now abandoned, which is a continuation-in-part of U.S. application Ser. No. 07/336, 672, filed Apr. 11, 1989, now abandoned, which is a continuation-in-part of U.S. application Ser. No. 07/208, 997, filed Jun. 17, 1988, now abandoned, all of which are herein incorporated by reference.

INTRODUCTION

1. Field of Invention

This invention relates to recombinant proteins, genes, and gene probes and more specifically to such proteins and probes derived from an enterically transmitted nonA/nonB hepatitis viral agent, to diagnostic methods and vaccine applications which employ the proteins and probes, and to gene segments that encode specific epitopes (and proteins artificially produced to contain those epitopes) that are particularly useful in diagnosis and prophylaxis.

2. Background

Enterically transmitted non-A/non-B hepatitis viral agent (ET-NANB; also referred to herein as HEV) is the reported cause of hepatitis in several epidemics and sporadic cases in Asia, Africa, Europe, Mexico, and the Indian subcontinent. Infection is usually by water contaminated with feces, although the virus may also spread by close physical contact. The virus does not seem to cause chronic infection. The viral etiology in ET-NANB has been demonstrated by infection of volunteers with pooled fecal isolates; immune electron microscopy (IEM) studies have shown virus particles with 27–34 nm diameters in stools from infected individuals. The virus particles reacted with antibodies in serum from infected individuals from geographically distinct regions, suggesting that a single viral agent or class is responsible for the majority of ET-NANB hepatitis seen worldwide. No antibody reaction was seen in serum from individuals infected with parenterally transmitted NANB virus (also known as hepatitis C virus or HCV), indicating a different specificity between the two NANB types.

In addition to serological differences, the two types of NANB infection show distinct clinical differences. ET-NANB is characteristically an acute infection, often associated with fever and arthralgia, and with portal inflammation and associated bile stasis in liver biopsy specimens (Arankalle). Symptoms are usually resolved within six weeks. Parenterally transmitted NANB, by contrast, produces a chronic infection in about 50% of the cases. Fever and arthralgia are rarely seen, and inflammation has a predominantly parenchymal distribution (Khuroo, 1980). The course of ET-NANBH is generally uneventful in healthy individuals, and the vast majority of those infected recover without the chronic sequelae seen with HCV. One peculiar epidemiologic feature of this disease, however, is the markedly high mortality observed in pregnant women; this is reported in numerous studies to be on the order of 10–20%. This finding has been seen in a number of epidemiologic studies but at present remains unexplained. Whether this reflects viral pathogenicity, the lethal consequence of the interaction of virus and immune suppressed (pregnant) host, or a reflection of the debilitated prenatal health of a susceptible malnourished population remains to be clarified.

The two viral agents can also be distinguished on the basis of primate host susceptibility. ET-NANB, but not the parenterally transmitted agent, can be transmitted to cynomolgus monkeys. The parenterally transmitted agent is more readily transmitted to chimpanzees than is ET-NANB (Bradley, 1987).

There have been major efforts worldwide to identify and clone viral genomic sequences associated with ET-NANB hepatitis. One goal of this effort, requiring virus-specific genomic sequences, is to identify and characterize the nature of the virus and its protein products. Another goal is to produce recombinant viral proteins which can be used in antibody-based diagnostic procedures and for a vaccine. Despite these efforts, viral sequences associated with ET-NANB hepatitis have not been successfully identified or cloned heretofore, nor have any virus-specific proteins been identified or produced.

3. Relevant Literature

Arankalle, V. A., et al., The Lancet, 550 (Mar. 12, 1988).

Bradley, D. W., et al., J Gen. Virol., 69:1 (1988).

Bradley, D. W. et al., Proc. Nat. Acad. Sci., USA, 84:6277 (1987).

Gravelle, C. R. et al., J. Infect. Diseases, 131:167 (1975).

Kane, M. A., et al., JAMA, 252:3140 (1984).

Khuroo, M. S., *Am. J. Med.,* 48:818 (1980).

Khuroo, M. S., et al., Am. J. Med., 68:818 (1983).

Maniatis, T., et al. *Molecular Cloning: A Laboratory Manual,* Cold Spring Harbor Laboratory 1982).

Seto, B., et al., Lancet, 11:941 (1964).

Sreenivasan, M. A., et al., J. Gen. Virol., 65:1005 (1984).

Tabor, E., et al., J. Infect. Dis., 140:789 (1979).

SUMMARY OF THE INVENTION

Novel compositions, as well as methods of preparation and use of the compositions are provided, where the compositions comprise viral proteins and fragments thereof derived from the viral agent for ET-NANB. A number of specific fragments of viral proteins (and the corresponding genetic sequences) that are particularly useful in diagnosis and vaccine production are also disclosed. Methods for preparation of ET-NANB viral proteins include isolating ET-NANB genomic sequences which are then cloned and expressed in a host cell. The resultant recombinant viral proteins find use as diagnostic agents and as vaccines. The genomic sequences and fragments thereof find use in preparing ET-NANB viral proteins and as probes for virus detection.

DESCRIPTION OF SPECIFIC EMBODIMENTS

Figure 1:
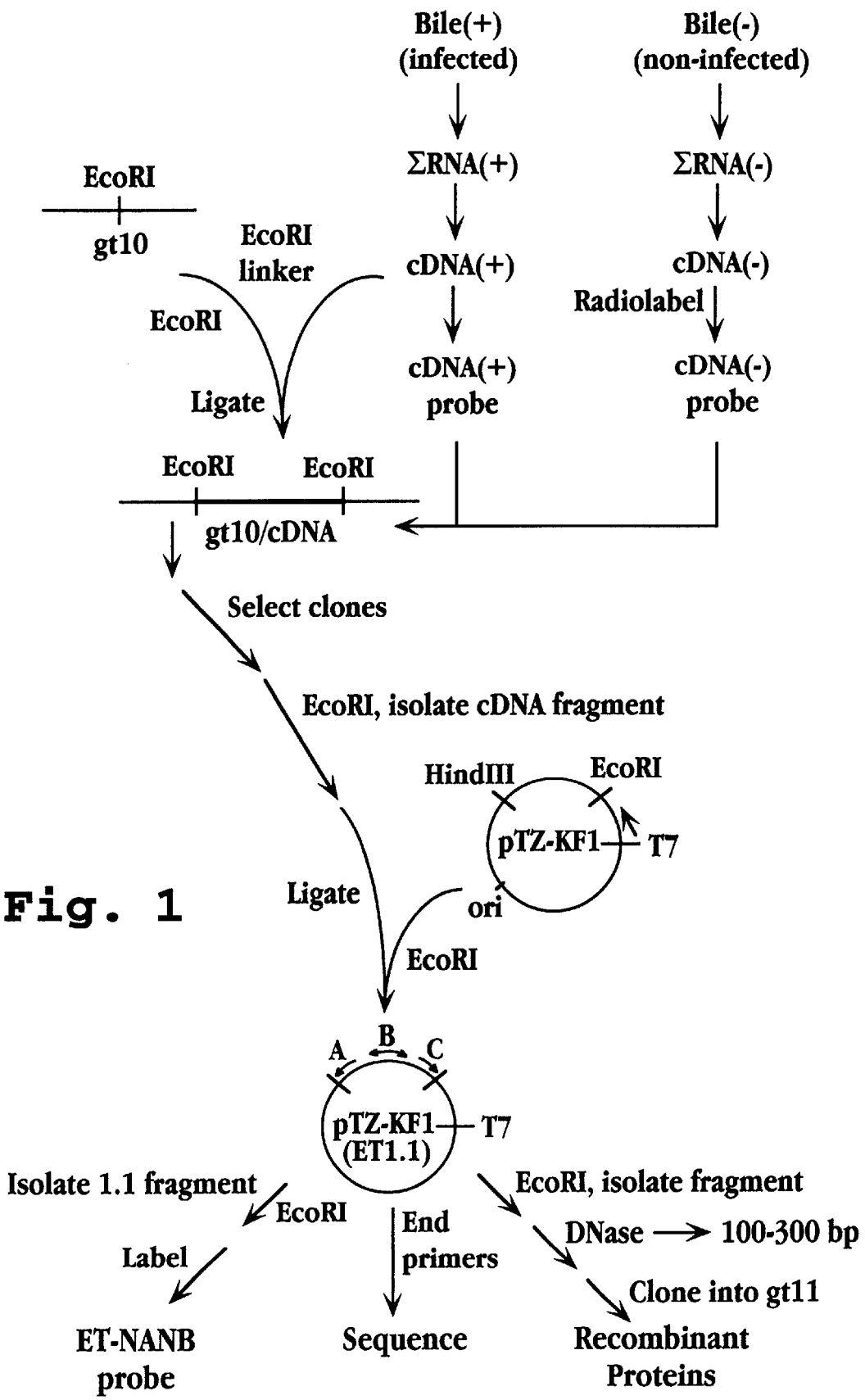
FIG. 1 shows vector constructions and manipulations used in obtaining and sequencing cloned ET-NANB fragment.

Novel compositions comprising generic sequences and fragments thereof derived from the viral agent for ET-NANB are provided, together with recombinant viral proteins produced using the genomic sequences and methods of using these compositions. Epitopes on the viral protein have been identified that are particularly useful in diagnosis and vaccine production. Small peptides containing the epitopes are recognized by multiple sera of patients infected with ET-NANB.

The molecular cloning of HEV was accomplished by two very different approaches. The first successful identification of a molecular clone was based on the differential hybridization of putative HEV cDNA clones to heterogeneous cDNA from infected and uninfected cyno bile. cDNAs from both sources were labeled to high specific activity with $^{32}P$ to identify a clone that hybridized specifically to the infected source probe. A cyno monkey infected with the Burma isolate of HEV was used in these first experiments. The sensitivity of this procedure is directly related to the relative abundance of the specific sequence against the overall background. In control experiments, it was found that specific identification of a target sequence may be obtained with as little as 1 specific part per 1000 background sequences. A number of clones were identified by this procedure using libraries and probes made from infected (Burma isolate) and control uninfected cyno bile. The first extensively characterized clone of the 16 plaques purified by this protocol was given the designation ET1.1.

ET1.1 was first characterized as both derived from and unique to the infected source cDNA. Heterogeneous cDNA was amplified from both infected and uninfected sources using a sequence independent single premier amplification technique (SISPA). This technique is described in copending application Ser. No. 208,512, filed Jun. 17, 1988. The limited pool of cDNA made from Burma infected cyno bile could then be amplified enzymatically prior to cloning or hybridization using putative HEV clones as probes. ET1.1 hybridized specifically to the original bile cDNA from the infected source. Further validation of this clone as derived from the genome of HEV was demonstrated by the similarity of the ET1.1 sequence and those present in SISPA cDNA prepared from five different human stool samples collected from different ET-NANBH epidemics including Somalia, Tashkent, Borneo, Mexico and Pakistan. These molecular epidemiologic studies established the isolated sequence as derived from the virus that represented the major cause of ET-NANBH worldwide.

The viral specificity of ET1.1 was further established by the finding that the clone hybridized specifically to RNA extracted from infected cyno liver. Hybridization analysis of polyadenylated RNA demonstrated a unique 7.5 Kb polyadenylated transcript not present in uninfected liver. The size of this transcript suggested that it represented the full length viral genome. Strand specific oligonucleotides were also used to probe viral genomic RNA extracted directly from semi-purified virions prepared from human stool. The strand specificity was based on the RNA-directed RNA polymerase (RDRP) open reading frame (ORF) identified in ET1.1 (see below). Only the probe detecting the sense strand hybridized to the nucleic acid. These studies characterized HEV as a plus sense, single stranded genome. Strand specific hybridization to RNA extracted from the liver also established that the vast majority of intracellular transcript was positive sense. Barring any novel mechanism for virus expression, the negative strand, although not detectable, would be present at a ratio of less than 1:100 when compared with the sense strand.

ET1.1 was documented as exogenous when tested by both Southern blot hybridization and PCR using genomic DNAs derived from uninfected humans, infected and uninfected cynos and also the genomic DNAs from *E. coli* and various bacteriophage sources. The latter were tested in order to rule out trivial contamination with an exogenous sequence introduced during the numerous enzymatic manipulations performed during cDNA construction and amplification. It was also found that the nucleotide sequence of the ET1.1 clone was not homologous to any entries in the Genebank database. The translated open reading frame of the ET1.1 clone did, however, demonstrate limited homology with consensus amino acid residues consistent with an RNA-directed RNA polymerase. This consensus amino acid motif is shared among all positive strand RNA viruses and, as noted above, is present at the 3' end of the HCV genome. The 1.3 Kb clone was therefore presumed to be derived, at least in part, from the nonstructural portion of the viral genome.

Because of the relationship of different strains of ET-NANB to each other that has been demonstrated by the present invention, the genome of the ET-NANB viral agent is defined in this specification as containing a region which is homologous to the 1.33 kb DNA EcoRI insert present in plasmid pTZKF1 (ET1.1) carried in *E. coli* strain BB4 and having ATCC deposit no. 67717. The ATCC address is 10801 University Blvd, Manasses, Va., 20110-2209. The entire sequence, in both directions, has now been identified as set forth below. The sequences of both strands are provided, since both strands can encode proteins. However, the sequence in one direction has been designated as the "forward" sequence because of statistical similarities to known proteins and because the forward sequence is known to be predominately protein-encoding. This sequence is set forth below along with the three possible translation sequences. There is one long open reading frame that starts at nucleotide 145 with an isoleucine and extends to the end of the sequence. The two other reading frames have many termination codons. Standard abbreviations for nucleotides and amino acids are used here and elsewhere in this specification.

The gene sequence is substantially identical to one given in the parent application. The present sequence differs in the omission of the first 37 nucleotides at the 5' end and last 13 nucleotides at the 3' end, which are derived from the linker used for cloning rather than from the virus. In addition, a G was omitted at position 227 of the sequence given in the parent application.

The gene sequence has SEQ ID NO.1; the first amino acid sequence in reading frame beginning with nucleotide 1 has SEQ ID NO.2.

The complementary strand, referred to here as the "reverse sequence," is set forth below in the same manner as the forward sequence set forth above. Several open reading frames, shorter than the long open reading frame found in the forward sequence, can be seen in this reverse sequence. Because of the relative brevity of the open reading frames in the reverse direction, they are probably not expressed.

The gene sequence has SEQ ID NO.5.

Identity of this sequence with sequences in etiologic agents has been confirmed by locating a corresponding sequence in a viral strain isolated in Burma. The Burmese isolate contains the following sequence of nucleotides (one strand and open reading frames shown). The gene sequence has SEQ ID NO.6; the protein sequence corresponding to ORF1 has SEQ ID NO.7: ORF2 has SEQ ID NO.8; and ORF3 has SEQ ID NO.9.

Total number of bases in the nucleotide sequence as presented is 7195. The poly-A tail present in the cloned sequence has been omitted.

The ability of the methods described herein to isolate and identify genetic material from other NANB hepatitis strains has been confirmed by identifying genetic material from an isolate obtained in Mexico. The sequence of this isolate was about 75% identical to the ET1.1 sequence set forth in SEQ ID NO.1 above. The sequence was identified by hybridization using the conditions set forth in Section II.B below.

In this different approach to isolation of the virus, cDNA libraries were made directly from a semi-purified human stool specimen collected from an outbreak of ET-NANB in Telixtac. The recovery of cDNA and the construction of representative libraries was assured by the application of sequence independent single premier amplification (SISPA). A cDNA library constructed in lambda gt11 from such an amplified cDNA population was screened with a serum considered to have "high" titer anti-HEV antibodies as assayed by direct immunofluorescence on liver sections from infected cynos. Two cDNA clones, denoted 406.3-2 and 406.4-2, were identified by this approach from a total of 60,000 screened. The sequence of these clones was subsequently localized to the 3' half of the viral genome by homology comparison to the HEV (Burma) sequence obtained from clones isolated by hybridization screening of libraries with the original ET1.1 clone.

These isolated cDNA epitopes when used as hybridization probes on Northern blots of RNA extracted from infected cyno liver gave a somewhat different result when compared to the Northern blots obtained with the ET1.1 probe. In addition to the single 7.5 Kb transcript seen using ET1.1, two additional transcripts of 3.7 and 2.0 Kb were identified using either of these epitopes as hybridization probes. These polyadenylated transcripts were identified using the extreme 3' end epitope clone (406.3-2) as probe and therefore established these transcripts as co-terminal with the 3' end of the genome (see below). One of the epitope clones (406.4-2) was subsequently shown to react in a specific fashion with antisera collected from 5 different geographic epidemics (Somalia, Burma, Mexico, Tashkent and Pakistan). The 406.3-2 clone reacted with sera from 4 out of these same 5 epidemics (Yarbough et al., 1990). Both clones reacted with only post inoculation antisera from infected cynos. The latter experiment confirmed that seroconversion in experimentally infected cynos was related to the isolated exogenous cloned sequence.

A composite cDNA sequence (obtained from several clones of the Mexican strain) is the Composite Mexico strain sequence (SEQ ID NO.10).

The sequence was obtained from polyadenylated clones. For clarity the 3' polyA "tail" has been omitted.

The sequence includes a partial cDNA sequence consisting of 1661 nucleotides that was identified in a previous application in this series. The previously identified partial sequence is set forth below, with certain corrections (SEQ ID NO.11). The corrections include deletion of the first 80 bases of the prior reported sequence, which are cloning artifacts; insertion of G after former position 174, of C after 270, and of GGCG after 279; change of C to T at former position 709, of GC to CG at 722–723, of CC to TT at 1238–39, and of C to G at 1606; deletion of T at former position 765; and deletion of the last 11 bases of the former sequence, which are part of a linker sequence and are not of viral origin.

When comparing the Burmese and Mexican strains, 75.7% identity is seen in a 7189 nucleotide overlap beginning at nucleotide 1 of the Mexican strain and nucleotide 25 of the Burmese strain.

In the same manner, a different strain of HEV was identified in an isolate obtained in Tashkent, U.S.S.R. The Tashkent sequence is given as (SEQ ID NO. 12).

As shown in the following comparison of sequences, the Tashkent (Tash.) sequence more closely resembles the Burma sequence than the Mexico sequence, as would be expected of two strains from more closely related geographical areas. The numbering system used in the comparison is based on the Burma sequence. As indicated previously, Burma has SEQ ID NO:6; Mexico, SEQ ID NO:10; and Tashkent, SEQ ID NO:12. The letters present in the lines between the sequences indicate conserved nucleotides.

```
                        10v       20v       30v       40v       50v       60v
        -BURMA    AGGCAGACCACATATGTGGTCGATGCCATGGAGGCCCATCAGTTTATTAAGGCTCCTGGCA
                                              GCCATGGAGGCCCA CAGTT ATTAAGGCTCCTGGCA
        -MEXICO                                GCCATGGAGGCCCACCAGTTCATTAAGGCTCCTGGCA 70v       80v       90v      100v      110v      120v
        -BURMA    TCACTACTGCTATTGAGCAGGCTGCTCTAGCAGCGGCCAACTCTGCCCTGGCGAATGCTG
                  TCACTACTGCTATTGAGCA GC GCTCTAGCAGCGGCCAACTC GCCCT GCGAATGCTG
        -MEXICO   TCACTACTGCTATTGAGCAAGCAGCTCTAGCAGCGGCCAACTCCGCCCTTGCGAATGCTG 130v      140v      150v      160v      170v      180v
        -BURMA    TGGTAGTTAGGCCTTTTCTCTCTCACCAGCAGATTGAGATCCTCATTAACCTAATGCAAC
                  TGGT GT  GGCCTTT CT TC CA CAGCAG TTGAGATCCT AT AA CT ATGCAAC
        -MEXICO   TGGTGGTCCGGCCTTTCCTTTCCCATCAGCAGGTTGAGATCCTTATAAATCTCATGCAAC 190v      200v      210v      220v      230v      240v
        -BURMA    CTCGCCAGCTTGTTTTCCGCCCCGAGGTTTTCTGGAATCATCCCATCCAGCGTGTCATCC
                  CTCG CAGCT GT TT CG CC GAGGTTTT TGGAATCA CC AT CA CGTGT AT C
        -MEXICO   CTCGGCAGCTGGTGTTTCGTCCTGAGGTTTTTTGGAATCACCCGATTCAACGTGTTATAC 250v      260v      270v      280v      290v      300v
        -BURMA    ATAACGAGCTGGAGCTTTACTGCCGCGCCCGCTCCGGCCGCTGTCTTGAAATTGGCGCCC
                  ATAA GAGCT GAGC  TA TGCCG GC CGCTC GG CGCTG CTTGA ATTGG GCCC
        -MEXICO   ATAATGAGCTTGAGCAGTATTGCCGTGCTCGCTCGGGTCGCTGCCTTGAGATTGGAGCCC
```

-continued

```
              310v       320v       330v       340v       350v       360v
-BURMA    ATCCCCGCTCAATAAATGATAATCCTAATGTGGTCCACCGCTGCTTCCTCCGCCCTGTTG
          A CC CGCTC AT AATGATAATCCTAATGT  TCCA CGCTGCTT CTCC CCC GT G
-MEXICO   ACCCACGCTCCATTAATGATAATCCTAATGTCCTCCATCGCTGCTTTCTCCACCCCGTCG 370v       380v       390v       400v       410v       420v
-BURMA    GGCGTGATGTTCAGCGCTGGTATACTGCTCCCACTCGCGGGCCGGCTGCTAATTGCCGGC
          G CG GATGTTCAGCGCTGGTA AC GC CC ACT G GG CC GC GC AA TG CG C
-MEXICO   GCCGGGATGTTCAGCGCTGGTACACAGCCCCGACTAGGGGACCTGCGGCGAACTGTCGCC 430V       440v       450v       460v       470v       480v
-BURMA    GTTCCGCGCTGCGCGGGCTTCCCGCTGCTGACCGCACTTACTGCCTCGACGGGTTTTCTG
          G TC GC CT CG GG CT CC  C GC GACCGCACTTACTG  T GA GG TTT C G
-MEXICO   GCTCGGCACTTCGTGGTCTGCCACCAGCCGACCGCACTTACTGTTTTGATGGCTTTGCCG 490v       500v       510v       520v       530v       540v
-BURMA    GCTGTAACTTTCCCGCCGAGACTGGCATCGCCCTCTACTCCCTTCATGATATGTCACCAT
          GCTG    TTT CCGCCGAGACTGG  T GC CTCTA TC CT CATGA  TG    CC
-MEXICO   GCTGCCGTTTTGCCGCCGAGACTGGTGTGGCTCTCTATTCTCTCCATGACTTGCAGCCGG 550v       560v       570v       580v       590v       600v
-BURMA    CTGATGTCGCCGAGGCCATGTTCCGCCATGGTATGACGCGGCTCTATGCCGCCCTCCATC
          CTGATGT GCCGAGGC ATG    CGCCA GG ATGAC CG CT TATGC GC  TCCA
-MEXICO   CTGATGTTGCCGAGGCGATGGCTCGCCACGGCATGACCCGCCTTTATGCAGCTTTCCACT 610v       620v       630v       640v       650v       660v
-BURMA    TTCCGCCTGAGGTCCTGCTGCCCCCTGGCACATATCGCACCGCATCGTATTTGCTAATTC
          T CC CC GAGGT CT CTGCC CCTGGCAC TA CG AC   CATC TA TTGCT AT C
-MEXICO   TGCCTCCAGAGGTGCTCCTCCTGGCACCTACCGGACATCATCTACTTGCTGATCC 670v       680v       690v       700v       710v       720v
-BURMA    ATGACGGTAGGCGCGTTGTGGTGACGTATGAGGGTGATACTAGTGCTGGTTACAACCACG
          A GA GGTA GCGCG  GT GT AC TATGAGGGTGA ACTAG GC GGTTACAA CA G
-MEXICO   ACGATGGTAAGCGCGCGGTTGTCACTTATGAGGGTGACACTAGCGCCGGTTACAATCATG 730v       740v       750v       760v       770v       780v
-BURMA    ATGTCTCCAACTTGCGCTCCTGGATTAGAACCACCAAGGTTACCGGAGACCATCCCCTCG
          ATGT  CCA C T CGC C TGGAT AG AC AC AAGGTT   GG GA CA CC   T G
-MEXICO   ATGTTGCCACCCTCCGCACATGGATCAGGACAACTAAGGTTGTGGGTGAACACCCTTTGG 790v       800v       810v       820v       830v       840v
-BURMA    TTATCGAGCGGGTTAGGGCCATTGGCTGCCACTTTGTTCTCTTGCTCACGGCAGCCCCGG
          T ATCGAGCGGGT  GGG  ATTGGCTG CACTTTGT  T  TTG TCAC GC GCCCC G
-MEXICO   TGATCGAGCGGGTGCGGGTATTGGCTGTCACTTTGTTGTTGATCACTGCGGCCCCTG 850v       860v       870v       880v       890v       900v
-BURMA    AGCCATCACCTATGCCTTATGTTCCTTACCCCCGGTCTACCGAGGTCTATGTCCGATCGA
          AGCC TC CC ATGCC TA GTTCCTTACCC CG TC AC GAGGTCTATGTCCG TC A
-MEXICO   AGCCCTCCCCGATGCCCTACGTTCCTTACCCGCGTTCGACGGAGGTCTATGTCCGGTCTA 910v       920V       930v       940v       950v       960v
-BURMA    TCTTCGGCCCGGGTGGCACCCCTTCCTTATTCCCAACCTCATGCTCCACTAAGTCGACCT
          TCTT GG CC GG GG  CCCC TC  T TTCCC ACC C TG  C     AAGTC AC T
-MEXICO   TCTTTGGGCCCGGCGGGTCCCCGTCGCTGTTCCCGACCGCTTGTGCTGTCAAGTCCACTT 970v       980v       990v       1000v      1010v      1020v
-BURMA    TCCATGCTGTCCCTGCCCATATTTGGGACCGTCTTATGCTGTTCGGGGCCACCTTGGATG
          T CA GC GTCCC  C CA AT TGGGACCGTCT ATGCT TT GGGGCCACC T GA G
-MEXICO   TTCACGCCGTCCCCACGCACATCTGGGACCGTCTCATGCTCTTTGGGGCCACCCTCGACG 1030v      1040v      1050v      1060v      1070v      1080v
-BURMA    ACCAAGCCTTTTGCTGCTCCCGTTTAATGACCTACCTTCGCGGCATTAGCTACAAGGTCA
          ACCA GCCTTTTGCTGCTCC G  T ATGAC TACCTTCG GGCATTAGCTA AAGGT A
-MEXICO   ACCAGGCCTTTTGCTGCTCCAGGCTTATGACGTACCTTCGTGGCATTAGCTATAAGGTAA 1090v      1100v      1110v      1120v      1130v      1140v
-BURMA    CTGTTGGTACCCTTGTGGCTAATGAAGGCTGGAATGCCTCTGAGGACGCCCTCACAGCTG
          CTGT GGT CCCT GT GCTAATGAAGGCTGGAATGCC C GAGGA GC CTCAC GC G
-MEXICO   CTGTGGGTGCCCTGGTCGCTAATGAAGGCTGGAATGCCACCGAGGATGCGCTCACTGCAG 1150v      1160v      1170v      1180v      1190v      1200v
-BURMA    TTATCACTGCCGCCTACCTTACCATTTGCCACCAGCGGTATCTCCGCACCCAGGCTATAT
          TTAT AC GC GC TACCT AC AT TG CA CAGCG TAT T CG ACCCAGGC AT T
-MEXICO   TTATTACGGCGGCTTACCTCACAATATGTCATCAGCGTTATTTGCGGACCCAGGCGATTT 1210v      1220v      1230v      1240v      1250v      1260v
-BURMA    CCAAGGGGATGCGTCGTCTGGAACGGGAGCATGCCCAGAAGTTTATAACACGCCTCTACA
          C AAGGG ATGCG CG CT GA C  GA CATGC CAGAA TTTAT  CACGCCTCTACA
-MEXICO   CTAAGGGCATGCGCCGGCTTGAGCTTGAACATGCTCAGAAATTTATTTCACGCCTCTACA
```

-continued

```
                  1270v      1280v      1290v      1300v      1310v      1320v
-BURMA    GCTGGCTCTTCGAGAAGTCCGGCCGTGATTACATCCCTGGCCGTCAGTTGGAGTTCTACG
          GCTGGCT TT GAGAAGTC GG CGTGATTACATCCC GGCCG CA TG AGTTCTACG
-MEXICO   GCTGGCTATTTGAGAAGTCAGGTCGTGATTACATCCCAGGCCGCCAGCTGCAGTTCTACG 1330v      1340v      1360v      1360v      1370v      1380v
-BURMA    CCCAGTGCAGGCGCTGGCTCTCCGCCGGCTTTCATCTTGATCCACGGGTGTTGGTTTTG
          C CAGTGC G CGCTGG T TC GCCGG TT CATCT GA CC CG    TT GTTTTTG
-MEXICO   CTCAGTGCCGCCGCTGGTTATCTGCCGGGTTCCATCTCGACCCCCGCACCTTAGTTTTTG 1390v      1400v      1410v      1420v      1430v      1440v
-BURMA    ACGAGTCGGCCCCCTGCCATTGTAGGACCGCGATCCGTAAGGCGCTCTCAAAGTTTTGCT
          A GAGTC G  CC TG    TG G ACC C ATCCG  G         AAA TTTTGCT
-MEXICO   ATGAGTCAGTGCCTTGTAGCTGCCGAACCACCATCCGGCGGATCGCTGGAAAATTTTGCT 1450v      1460v      1470v      1480v      1490v      1500v
-BURMA    GCTTCATGAAGTGGCTTGGTCAGGAGTGCACCTGCTTCCTTCAGCCTGCAGAAGGCGCCG
          G TT ATGAAGTGGCT GGTCAGGAGTG  C TG TTCCT CAGCC GC GA GG      G
-MEXICO   GTTTTATGAAGTGGCTCGGTCAGGAGTGTTCTTGTTTCCTCCAGCCCGCCGAGGGGCTGG 1510v      1520v      1530v      1540v      1550v      1560v
-BURMA    TCGGCGACCAGGGTCATGATAATGAAGCCTATGAGGGGTCCGATGTTGACCCTGCTGAGT
            GGCGACCA GGTCATGA AATGA GCCTATGA GG TC GATGTTGA  CTGCTGAG
-MEXICO   CGGGCGACCAAGGTCATGACAATGAGGCCTATGAAGGCTCTGATGTTGATACTGCTGAGC 1570v      1580v      1590v      1600v      1610v      1620v
-BURMA    CCGCCATTAGTGACATATCTGGGTCCTATGTCGTCCCTGGCACTGCCCTCCAACCGCTCT
          C GCCA      GACAT  C GG TC TA  TCGT     TGG     C CT CAA C  TCT
-MEXICO   CTGCCACCCTAGACATTACAGGCTCATACATCGTGGATGGTCGGTCTCTGCAAACTGTCT 1630v      1640v      1650v      1660v      1670v      1680v
-BURMA    ACCAGGCCCTCGATCTCCCCGCTGAGATTGTGGCTCGCGCGGGCCGGCTGACCGCCACAG
          A CA GC CTCGA CT CC GCTGA  T GT GCTCGCGC G CCG CTG C GC ACAG
-MEXICO   ATCAAGCTCTCGACCTGCCAGCTGACCTGGTAGCTCGCGCAGCCCGACTGTCTGCTACAG 1690v      1700v      1710v      1720v      1730v      1740v
-BURMA    TAAAGGTCTCCCAGGTCGATGGGCGGATCGATTGCGAGACCCTTCTTGGTAACAAAACCT
          T A GT C   A   C  TGG CG  T GATTGC A AC   T  T GG AA AA AC T
-MEXICO   TTACTGTTACTGAAACCTCTGGCCGTCTGGATTGCCAAACAATGATCGGCAATAAGACTT 1750v      1760v      1770v      1780v      1790v      1800v
-BURMA    TTCGCACGTCGTTCGTTGACGGGGCGGTCTTAGAGACCAATGGCCCAGAGCGCCACAATC
          TTC CAC   C TT GTTGA GGGGC    C T GAG    AA GG CC GAGC   C  AA C
-MEXICO   TTCTCACTACCTTTGTTGATGGGGCACGCCTTGAGGTTAACGGGCCTGAGCAGCTTAACC 1810v      1820v      1830v      1840v      1850v      1860v
-BURMA    TCTCCTTCGATGCCAGTCAGAGCACTATGGCCGCTGGCCCTTTCAGTCTCACCTATGCCG
          TCTC TT GA   C   CAG G A TATGGC GC GGCCC TT  G CTCACCTATGC G
-MEXICO   TCTCTTTTGACAGCCAGCAGTGTAGTATGGCAGCCGGCCCGTTTTGCCTCACCTATGCTG 1870v      1880v      1890v      1900v      1910v      1920v
-BURMA    CCTCTGCAGCTGGGCTGGAGGTGCGCTATGTTGCTGCCGGGCTTGACCATCGGGCGGTTT
          CC   G  G  GGGCTGGA GT C  T T    C GC GG CT GA    CG G GTTT
-MEXICO   CCGTAGATGGCGGGCTGGAAGTTCATTTTTCCACCGCTGGCCTCGAGAGCCGTGTTGTTT 1930v      1940v      1950v      1960v      1970v      1980v
-BUPMA    TTGCCCCCGGTGTTTCACCCCGGTCAGCCCCCGGCGAGGTTACCGCCTTCTGCTCTGCCC
          T  CCCC GGT  T C  CC    C  C CC  G GAGGT ACCGCCTTCTGCTC GC C
-MEXICO   TCCCCCCTGGTAATGCCCCGACTGCCCCGCCGAGTGAGGTCACCGCCTTCTGCTCAGCTC 1990v      2000v      2010v      2020v      2030v      2040v
-BURMA    TATACAGGTTTAACCGTGAGGCCCAGCGCCATTCGCTGATCGGTAACTTATGGTTCCATC
          T TA AGG    AACCG  AG  CCAGCGCCA TCG T AT GGTA  TT TGG T CA C
-MEXICO   TTTATAGGCACAACCGGCAGAGCCAGCGCCAGTCGGTATTGGTAGTTTGTGGCTGCACC 2050v      2060v      2070v      2080v      2090v      2100v
-BURMA    CTGAGGGACTCATTGGCCTCTTCGCCCCGTTTTCGCCCGGGCATGTTTGGGAGTCGGCTA
          CTGA GG  T  T GGCCT TTC C CC TTTTC CCCGGGCATG  TGG  GTC GCTA
-MEXICO   CTGAAGGTTTGCTCGGCCTGTTCCCGCCCTTTTCACCCGGGCATGAGTGGCGGTCTGCTA 2110v      2120v      2130v      2140v      2150v      2160v
-BURMA    ATCCATTCTGTGGCGAGAGCACACTTTACACCCGTACTTGGTCGGAGGTTGATGCCGTCT
          A CCATT TG GGCGAGAGCAC CT TACACCCG ACTTGGTC    TT    G C
-MEXICO   ACCCATTTTGCGGCGAGAGCACGCTCTACACCCGCACTTGGTCCACAATTACAGACACAC 2170v      2180v      2190v      2200v      2210v      2220v
-BURMA    CTAGTCCAGCCCGGCCTGACTTAGGTTTTATGTCTGAGCCTTCTATACCTAGTAGGGCCG
          C    CGC GGC    T GGT T TG TG  CT C    C G GGC
-MEXICO   CCTTAACTGTCGGGCTAATTTCCGGTCATTTGGATGCTGCTCCCCACTCGGGGGGGCCAC
```

```
                    2230v       2240v       2250v       2260v       2270v       2280v
-BURMA      CCACGCCTACCCTGGCGGCCCCTCTACCCCCCCCTGCACCGGACCCTTCCCCCCCTCCCT
            C  C  CT CC    G   C  CT TA  C C  CTG   C         C    CCC C
-MEXICO     CTGCTACTGCCACAGGCCCTGCTGTAGGCTCGTCTGACTCTCCAGACCCTGACCCGCTAC 2290v       2300v       2310v       2320v       2330v       2340v
-BURMA      CTGCCCCGGCGCTTGCTGAGCCGGCTTCTGGCGCTACCGCCGGGGCCCCGGCCATAACTC
            CTG       C   TG    C   C TCTGG GC       C G  G CCC    C    A T
-MEXICO     CTGATGTTACAGATGGCTCACGCCCCTCTGGGGCCCGTCCGGCTGGCCCCAACCCGAATG 2350v       2360v       2370v       2380v       2390v       2400v
-BURMA      ACCAGACGGCCCGGCACCGCCGCCTGCTCTTCACCTACCCGGATGGCTCTAAGGTATTCG
                C    CG            CGCCGC T CT    CACCTACCC GA GGC CTAAG T T  G
-MEXICO     GCGTTCCGCAG------CGCCGCTTACTACACACCTACCCTGACGGCGCTAAGATCTATG 2410v       2420v       2430v       2440v       2450v       2460v
-BURMA      CCGGCTCGCTGTTCGAGTCGACATGCACGTGGCTCGTTAACGCGTCTAATGTTGACCACC
             CGGCTC  T  TTCGAGTC   TGCAC TGGCT GT AACGC TCTAA G  G CCACC
-MEXICO     TCGGCTCCATTTTCGAGTCTGAGTGCACCTGGCTTGTCAACGCATCTAACGCCGGCCACC 2470v       2480v       2490v       2500v       2510v       2520v
-BURMA      GCCCTGGCGGCGGGCTTTGCCATGCATTTTACCAAAGGTACCCCGCCTCCTTTGATGCTG
            GCCCTGG  GGCGGGCTTTG CATGC TTTT   CA  G TACCC G  TC TTTGA GC
-MEXICO     GCCCTGGTGGCGGGCTTTGTCATGCTTTTTTTCAGCGTTACCCTGATTCGTTTGACGCCA 2530v       2540v       2550v       2560v       2570v       2580v
-BURMA      CCTCTTTTGTGATGCGCGACGGCGCGGCCGCGTACACACTAACCCCCCGGCCAATAATTC
            CC    TTTGTGATGCG GA GG     GCCGCGTA AC CT AC CCCCGGCC AT ATTC
-MEXICO     CCAAGTTTGTGATGCGTGATGGTCTTGCCGCGTATACCCTTACACCCCGGCCGATCATTC 2590v       2600v       2610v       2620v       2630v       2640v
-BURMA      ACGCTGTCGCCCCTGATTATAGGTTGGAACATAACCCAAAGAGGCTTGAGGCTGCTTATC
            A GC GT GCCCC  GA TAT G TTGGAACATAACCC  AAGAGGCT GAGGCTGC TA C
-MEXICO     ATGCGGTGGCCCCGGACTATCGATTGGAACATAACCCCAAGAGGCTCGAGGCTGCCTACC 2650v       2660v       2670v       2680v       2690v       2700v
-BURMA      GGGAAACTTGCTCCCGCCTCGGCACCGCTGCATACCCGCTCCTCGGGACCGGCATATACC
            G GA ACTTGC CCCGCC  GGCAC GCTGC TA CC CTC T GG  C GGCAT TACC
-MEXICO     GCGAGACTTGCGCCCGCCGAGGCACTGCTGCCTATCCACTCTTAGGCGCTGGCATTTACC 2710v       2720v       2730v       2740v       2750v       2760v
-BURMA      AGGTGCCGATCGGCCCCAGTTTTGACGCCTGGGAGCGGAACCACCGCCCCGGGGATGAGT
            AGGTGCC   T  G    AGTTTTGA GCCTGGGAGCGGAACCACCGCCC    GA GAG
-MEXICO     AGGTGCCTGTTAGTTTGAGTTTTGATGCCTGGGAGCGGAACCACCGCCCGTTTGACGAGC 2770v       2780v       2790v       2800v       2810v       2820v
-BURMA      TGTACCTTCCTGAGCTTGCTGCCAGATGGTTTGAGGCCAATAGGCCGACCCGCCCGACTC
            T TACCT  C GAGCT GC GC  G TGGTTTGA CCAA  G CC     C  CC AC
-MEXICO     TTTACCTAACAGAGCTGGCGGCTCGGTGGTTTGAATCCAACCGCCCCGGTCAGCCCACGT 2830v       2840v       2850v       2860v       2870v       2880v
-BURMA      TCACTATAACTGAGGATGTTGCACGGACAGCGAATCTGGCCATCGAGCTTGACTCAGCCA
            T A  ATAACTGAGGAT    GC CG   C GC AA  CTGGCC T GAGCTTGACTC  G  A
-MEXICO     TGAACATAACTGAGGATACCGCCCGTGCGGCCAACCTGGCCCTGGAGCTTGACTCCGGGA 2890v       2900v       2910v       2920v       2930v       2940v
-BURMA      CAGATGTCGGCCGGGCCTGTGCCGGCTGTCGGGTCACCCCCGGCGTTGTTCAGTACCAGT
              GA GT GGCCG GC  TGTGCCGG TGT    GTC   CC GGCGTTGT C GTA CAGT
-MEXICO     GTGAAGTAGGCCGCGCATGTGCCGGGTGTAAAGTCGAGCCTGGCGTTGTGCGGTATCAGT 2950v       2960v       2970v       2980v       2990v       3000v
-BURMA      TTACTGCAGGTGTGCCTGGATCCGGCAAGTCCCGCTCTATCACCCAAGCCGATGTGGACG
            TTAC GC GGTGT CC GG TC GGCAAGTC    TC  T   CA GC GATGTGGA G
-MEXICO     TTACAGCCGGTGTCCCCGGCTCTGGCAAGTCAAAGTCCGTGCAACAGGCGGATGTGGATG 3010v       3020v       3030v       3040v       3050v       3060v
-BURMA      TTGTCGTGGTCCCGACGCGTGAGTTGCGTAATGCCTGGCGCCGTCGCGGCTTTGCTGCTT
            TTGT GT GT CC AC CG GAG T CG AA CG  TGGCG CG CG GGCTTTGC GC T
-MEXICO     TTGTTGTTGTGCCCACTCGCGAGCTTCGGAACGCTTGGCGGCGCCGGGGCTTTGCGGCAT 3070v       3080v       3090v       3100v       3110v       3120v
-BURMA      TTACCCCGCATACTGCCGCCAGAGTCACCCAGGGGCGCCGGGTTGTCATTGATGAGGCTC
            T AC  CCGCA ACTGC GCC G  GTCAC    GG CG  GGGTTGTCATTGATGAGGC C
-MEXICO     TCACTCCGCACACTGCGGCCCGTGTCACTAGCGGCCGTAGGGTTGTCATTGATGAGGCCC 3130v       3140v       3150v       3160v       3170v       3180v
-BURMA      CATCCCTCCCCCCTCACCTGCTGCTGCTCCACATGCAGCGGGCCGCCACCGTCCACCTTC
            C TC CTCCCCCC  CAC TGCTGCT  T CA ATGCAGCG GC GC   C GT CACCT C
-MEXICO     CTTCGCTCCCCCCACACTTGCTGCTTTTACATATGCAGCGTGCTGCATCTGTGCACCTCC
```

-continued

```
            3190v      3200v      3210v      3220v      3230v      3240v
-BURMA      TTGGCGACCCGAACCAGATCCCAGCCATCGACTTTGAGCACGCTGGGCTCGTCCCCGCCA
            TTGG  GACCCGAA CAGATCCC GCCAT GA TTTGAGCAC C GG CT  T CC GC A
-MEXICO     TTGGGGACCCGAATCAGATCCCCGCCATAGATTTTGAGCACACCGGTCTGATTCCAGCAA 3250v      3260v      3270v      3280v      3290v      3300v
-BURMA      TCAGGCCCGACTTAGGCCCCACCTCCTGGTGGCATGTTACCCATCGCTGGCCTGCGGATG
            T  GGCC GA TT G CCC AC TC TGGTGGCATGT ACCCA CG TG CCTGC GATG
-MEXICO     TACGGCCGGAGTTGGTCCCGACTTCATGGTGGCATGTCACCCACCGTTGCCCTGCAGATG 3310v      3320v      3330v      3340v      3350v      3360v
-BURMA      TATGCGAGCTCATCCGTGGTGCATACCCCATGATCCAGACCACTAGCCGGGTTCTCCGTT
            T  TG GAG T  TCCGTGGTGC TACCC A  ATCCAGAC AC AG   GGT CTCCGTT
-MEXICO     TCTGTGAGTTAGTCCGTGGTGCTTACCCTAAAATCCAGACTACAAGTAAGGTGCTCCGTT 3370v      3380v      3390v      3400v      3410v      3420v
-BURMA      CGTTGTTCTGGGGTGAGCCTGCCGTCGGGCAGAAACTAGTGTTCACCCAGGCGGCCAAGC
            C  T  TTCTGGGG GAGCC GC GTCGG CAGAA CTAGTGTTCAC CAGGC GC AAG
-MEXICO     CCCTTTTCTGGGGAGAGCCAGCTGTCGGCCAGAAGCTAGTGTTCACACAGGCTGCTAAGG 3430v      3440v      3450v      3460v      3470v      3480v
-BURMA      CCGCCAACCCCGGCTCAGTGACGGTCCACGAGGCGCAGGGCGCTACCTACACGGAGACCA
            CCGC  ACCCCGG TC  T ACGGTCCA GAGGC CAGGG GC AC T  AC   AC A
-MEXICO     CCGCGCACCCCGGATCTATAACGGTCCATGAGGCCCAGGGTGCCACTTTTACCACTACAA 3490v      3500v      3510v      3520v      3530v      3540v
-BURMA      CTATTATTGCCACAGCAGATGCCCGGGGCCTTATTCAGTCGTCTCGGGCTCATGCCATTG
            CTAT ATTGC AC GCAGATGCCCG GGCCT AT CAGTC TC CGGGCTCA GC AT G
-MEXICO     CTATAATTGCAACTGCAGATGCCCGTGGCCTCATACAGTCCTCCCGGGCTCACGCTATAG 3550v      3560v      3570v      3580v      3590v      3600v
-BURMA      TTGCTCTGACGCGCCACACTGAGAAGTGCGTCATCATTGACGCACCAGGCCTGCTTCGCG
            TTGCTCT AC   G CA ACTGA AA TG GT AT   TTGAC C CC GGCCTG T CG G
-MEXICO     TTGCTCTCACTAGGCATACTGAAAAATGTGTTATACTTGACTCTCCCGGCCTGTTGCGTG 3610v      3620v      3630v      3540v      3650v      3660v
-BURMA      AGGTGGGCATCTCCGATGCAATCGTTAATAACTTTTTCCTCGCTGGTGGCGAAATTGGTC
            AGGTGGG ATCTC GATGC AT GTTAATAA TT TTCCT  C GGTGGCGA  TTGGTC
-MEXICO     AGGTGGGTATCTCAGATGCCATTGTTAATAATTTCTTCCTTTCGGGTGGCGAGGTTGGTC 3670v      3680v      3690v      3700v      3710v      3720v
-BURMA      ACCAGCGCCCATCAGTTATTCCCCGTGGCAACCCTGACGCCAATGTTGACACCCTGGCTG
            ACCAG G CCATC GT ATTCC CG GGCAACCCTGAC  CAATGTTGAC   CT GC G
-MEXICO     ACCAGAGACCATCGGTCATTCCGCGAGGCAACCCTGACCGCAATGTTGACGTGCTTGCGG 3730v      3740v      3750v      3760v      3770v      3780v
-BURMA      CCTTCCCGCCGTCTTGCCAGATTAGTGCCTTCCATCAGTTGGCTGAGGAGCTTGGCCACA
            C  TT CC CC TC TGCCA AT AG GCCTTCCATCAG T GCTGAGGAGCT GGCCAC
-MEXICO     CGTTTCCACCTTCATGCCAAATAAGCGCCTTCCATCAGCTTGCTGAGGAGCTGGGCCACC 3790v      3800v      3810v      3820v      3830v      3840v
-BURMA      GACCTGTCCCTGTTGCAGCTGTTCTACCACCCTGCCCCGAGCTCGAACAGGGCCTTCTCT
            G  CC G  CC GT GC GCTGT CTACC CCCTGCCC GAGCT GA CAGGGCCTTCTCT
-MEXICO     GGCCGGCGCCGGTGGCGGCTGTGCTACCTCCTGCCCTGAGCTTGAGCAGGGCCTTCTCT 3850v      3860v      3870v      3880v      3890v      3900v
-BURMA      ACCTGCCCCAGGAGCTCACCACCTGTGATAGTGTCGTAACATTTGAATTAACAGACATTG
            A CTGCC CAGGAGCT  CC CCTGTGA AGTGT GT ACATTTGA  TAAC GACATTG
-MEXICO     ATCTGCCACAGGAGCTAGCCTCCTGTGACAGTGTTGTGACATTTGAGCTAACTGACATTG 3910v      3920v      3930v      3940v      3950v      3950v
-BURMA      TGCACTGCCGCATGGCCGCCCCGAGCCAGCGCAAGGCCGTGCTGTCCACACTCGTGGGCC
            TGCACTGCCGCATGGC GCCCC AGCCA  GAA GC GT  TGTCCAC CT GT GGCC
-MEXICO     TGCACTGCCGCATGGCGGCCCCTAGCCAAAGGAAAGCTGTTTTGTCCACGCTGGTAGGCC 3970v      3980v      3990v      4000v      4010v      4020v
-BURMA      GCTACGGCGGTCGCACAAAGCTCTACAATGCTTCCCACTCTGATGTTCGCGACTCTCTCG
            G  TA GGC G CGCACAA GCT TA  ATGC   CAC C GATGT CGCG CTC CT G
-MEXICO     GGTATGGCAGACGCACAAGGCTTTATGATGCGGGTCACACCGATGTCCGCGCCTCCCTTG 4030v      4040v      4050v      4060v      4070v      4080v
-TASHKENT                          GGCCCCGTACAGGTCACAACCTGTGAGTTGTACGAGCTAG
                                   GGCCCCGTACAGGT ACAAC TGTGA TTGTACGAGCTAG
-BURMA      CCCGTTTTATCCCGGCCATTGGCCCCGTACAGGTTACAACTTGTGAATTGTACGAGCTAG
            C CG TTTAT CC  C  T GG C  GT   G AC AC TGTGAA T T  GAGCT G
-MEXICO     CGCGCTTTATTCCCACTCTCGGGCGGGTTACTGCCACCACCTGTGAACTCTTTGAGCTTG
```

```
                    -continued
           4090v      4100v      4110v      4120v      4130v      4140v
-TASHKENT  TGGAGGCCATGGTCGAGAAAGGCCAGGATGGCTCCGCCGTCCTTGAGCTCGATCTCTGCA
           TGGAGGCCATGGTCGAGAA GGCCAGGATGGCTCCGCCGTCCTTGAGCT GATCT TGCA
-BURMA     TGGAGGCCATGGTCGAGAAGGGCCAGGATGGCTCCGCCGTCCTTGAGCTTGATCTTTGCA
           T GAGGC ATGGT GAGAAGGGCCA GA GG TC GCCGTCCT GAG T GAT T TGCA
-MEXICO    TAGAGGCGATGGTGGAGAAGGGCCAAGACGGTTCAGCCGTCCTCGAGTTGGATTTGTGCA 4150v      4160v      4170v      4180v      4190v      4200v
-TASHKENT  ACCGTGACGTGTCCAGGATCACCTTTTTCCAGAAAGATTGCAATAAGTTCACCACGGGAG
           ACCGTGACGTGTCCAGGATCACCTT TTCCAGAAAGATTG AA AAGTTCACCAC GG G
-BURMA     ACCGTGACGTGTCCAGGATCACCTTCTTCCAGAAAGATTGTAACAAGTTCACCACAGGTG
            CCG GA GT TCC G AT ACCTT TTCCAGAA GATTGTAACAAGTTCAC AC GG G
-MEXICO    GCCGAGATGTCTCCCGCATAACCTTTTTCCAGAAGGATTGTAACAAGTTCACGACCGGCG 4210v      4220v      4230v      4240v      4250v      4260v
-TASHKENT  AGACCATCGCCCATGGTAAAGTGGGCCAGGGCATTTCGGCCTGGAGTAAGACCTTCTGTG
           AGACCAT GCCCATGGTAAAGTGGGCCAGGGCATTTCGGCCTGGAG AAGACCTTCTG G
-BURMA     AGACCATTGCCCATGGTAAAGTGGGCCAGGGCATCTCGGCCTGGAGCAAGACCTTCTGCG
            AGAC ATTGC CATGG AAAGT GG CAGGG ATCT    CTGGAG AAGAC TT TG G
-MEXICO    AGACAATTGCGCATGGCAAAGTCGGTCAGGGTATCTTCCGCTGGAGTAAGACGTTTTGTG 4270v      4280v      4290v      4300v      4310v      4320v
-TASHKENT  CCCTTTTCGGCCCCTGGTTCCGTGCTATTGAGAAGGCTATTCTGGCCCTGCTCCCTCAGG
           CCCT TT GGCCC TGGTTCCG GCTATTGAGAAGGCTATTCTGGCCCTGCTCCCTCAGG
-BURMA     CCCTCTTTGGCCCTTGGTTCCGCGCTATTGAGAAGGCTATTCTGGCCCTGCTCCCTCAGG
           CCCT TTTGGCCC TGGTTCCG GC ATTGAGAAGGCTATTCT  CCCT  T CC CA G
-MEXICO    CCCTGTTTGGCCCCTGGTTCCGTGCGATTGAGAAGGCTATTCTATCCCTTTTACCACAAG 4330v      4340v      4350v      4360v      4370v      4380v
-TASHKENT  GTGTGTTTTATGGGGATGCCTTTGATGACACCGTCTTCTCGGCGCGTGTGGCCGCAGCAA
           GTGTGTTTTA GG GATGCCTTTGATGACACCGTCTTCTCGGCG TGTGGCCGCAGCAA
-BURMA     GTGTGTTTTACGGTGATGCCTTTGATGACACCGTCTTCTCGGCGGTGTGGCCGCAGCAA
            TGTGTT TACGG GATGC T TGA GAC C GT TTCTC GC GC GTGGC G  GC A
-MEXICO    CTGTGTTCTACGGGGATGCTTATGACGACTCAGTATTCTCTGCTGCCGTGGCTGGCGCCA 4390v      4400v      4410v      4420v      4430v      4440v
-TASHKENT  AGGCGTCCATGGTGTTTGAGAATGACTTTTCTGAGTTTGACTCCACCCAGAATAATTTTT
           AGGC TCCATGGTGTTTGAGAATGACTTTTCTGAGTTTGACTCCACCCAGAATAA TTTT
-BURMA     AGGCATCCATGGTGTTTGAGAATGACTTTTCTGAGTTTGACTCCACCCAGAATAACTTTT
                  CCATGGTGTTTGA AATGA TTTTCTGAGTTTGACTC AC CAGAATAACTTTT
-MEXICO    GCCATGCCATGGTGTTTGAAAATGATTTTTCTGAGTTTGACTCGACTCAGAATAACTTTT 4450v      4460v      4470v      4480v      4490v      4500v
-TASHKENT  CCCTGGGCCTAGAGTGTGCTATTATGGAGAAGTGTGGGATGCCGAAGTGGCTCATCCGCT
           C CTGGG CTAGAGTGTGCTATTATGGAG AGTGTGGGATGCCG AGTGGCTCATCCGC
-BURMA     CTCTGGGTCTAGAGTGTGCTATTATGGAGGAGTGTGGGATGCCGCAGTGGCTCATCCGCC
           C CT GGTCT GAGTG GC ATTATGGA GAGTGTGG ATGCC CAGTGGCT  TC G
-MEXICO    CCCTAGGTCTTGAGTGCGCCATTATGGAAGAGTGTGGTATGCCCCAGTGGCTTGTCAGGT 4510v      4520v      4530v      4540v      4550v      4560v
-TASHKENT  TGTACCACCTTATAAGGTCTGCGTGGATCCTGCAGGCCCCGAAGGAGTCCCTGCGAGGGT
           TGTA CACCTTATAAGGTCTGCGTGGATC TGCAGGCCCCGAAGGAGTC CTGCGAGGGT
-BURMA     TGTATCACCTTATAAGGTCTGCGTGGATCTTGCAGGCCCCGAAGGAGTCTCTGCGAGGGT
            TGTA CA    T  GGTC GCGTGGATC TGCAGGCCCC AA GAGTCT TG GAGGGT
-MEXICO    TGTACCATGCCGTCCGGTCGGCGTGGATCCTGCAGGCCCCAAAAGAGTCTTTGAGAGGGT 4570v      4580v      4590v      4600v      4610v      4620v
-TASHKENT  GTTGGAAGAAACACTCCGGTGAGCCCGGCACTCTTCTATGGAATACTGTCTGGAACATGG
            TTGGAAGAAACACTCCGGTGAGCCCGGCACTCTTCTATGGAATACTGTCTGGAA ATGG
-BURMA     TTTGGAAGAAACACTCCGGTGAGCCCGGCACTCTTCTATGGAATACTGTCTGGAATATGG
           T TGGAAGAA CA TC GGTGAGCC GGCA   T CT TGGAATAC GT TGGAA ATGG
-MEXICO    TCTGGAAGAAGCATTCTGGTGAGCCGGGCAGCTTGCTCTGGAATACGGTGTGGAACATGG 4630v      4640v      4650v      4660v      4670v      4680v
-TASKENT   CCGTTATCACCCATTGTTACGATTTCCGCGATTTGCAGGTGGCTGCCTTTAAAGGTGATG
           CCGTTAT ACCCA TGTTA GA TTCCGCGATTT  AGGTGGCTGCCTTTAAAGGTGATG
-BURMA     CCGTTATTACCCACTGTTATGACTTCCGCGATTTTCAGGTGGCTGCCTTTAAAGGTGATG
           C  T ATT CCCA TG TATGA TTCCG GA  T CAGGT GC GCCTT AA GG GA G
-MEXICO    CAATCATTGCCCATTGCTATGAGTTCCGGGACCTCCAGGTTGCCGCCTTCAAGGGCGACG 4690v      4700v      4710v      4720v      4730v      4740v
-TASHKENT  ATTCGATAGTGCTTTGCAGTGAGTACCGTCAGAGTCCAGGGGCTGCTGTCCTGATTGCTG
           ATTCGATAGTGCTTTGCAGTGAGTA CGTCAGAGTCCAGG GCTGCTGTCCTGAT GC G
-BURMA     ATTCGATAGTGCTTTCCAGTGAGTATCGTCAGAGTCCAGGAGCTGCTGTCCTGATCGCCG
            A TCG T GT CT TG AGTGA TA CG CAGAG CCAGG GC G T   CT AT GC G
-MEXICO    ACTCGGTCGTCCTCTGTAGTGAATACCGCCAGAGCCCAGGCGCCGGTTCGCTTATAGCAG
```

```
                    -continued
                4750v     4760v     4770v     4780v     4790v     4800v
-TASHKENT  GCTGTGGCTTAAAGCTGAAGGTGGGTTTCCGTCCGATTGGTTTGTATGCAGGTGTTGTGG
           GCTGTGGCTT AAG TGAAGGT G TTTCCG CCGAT GGTTTGTATGCAGGTGTTGTGG
-BURMA     GCTGTGGCTTGAAGTTGAAGGTAGATTTCCGCCCGATCGGTTTGTATGCAGGTGTTGTGG
           GCTGTGG TTGAAGTTGAAGG  GA TTCCG CCGAT GG  TGTATGC GG GTTGT G
-MEXICO    GCTGTGGTTTGAAGTTGAAGGCTGACTTCCGGCCGATTGGGCTGTATGCCGGGGTTGTCG 4810v     4820v     4830v     4840v     4850v     4860v
-TASHKENT  TGACCCCCGGCCTTGGCGCGCTTCCCGACGTCGTGCGCTTGTCCGGCCGGCTTACTGAGA
           TG CCCCCGGCCTTGGCGCGCTTCCCGA GT GTGCGCTTG CCGGCCGGCTTAC GAGA
-BURMA     TGGCCCCCGGCCTTGGCGCGCTCCCTGATGTTGTGCGCTTCGCCGGCCGGCTTACCGAGA
           T GCCCC GG CT GG GC CT CC GATGT GT CG TTCGCCGG CGGCTT C GAGA
-MEXICO    TCGCCCCGGGGCTCGGGGCCCTACCCGATGTCGTTCGATTCGCCGGACGGCTTTCGGAGA 4870v     4880v     4890v     4900v     4910v     4920v
-TASHKENT  AGAATTGGGGCCCTGGCCCTGAGCGGGCGGAGCAGCTCCGCCTTGCTGT
           AGAATTGGGGCCCTGGCCCTGAGCGGGCGGAGCAGCTCCGCCT GCTGT
-BURMA     AGAATTGGGGCCCTGGCCCTGAGCGGGCGGAGCAGCTCCGCCTCGCTGTTAGTGATTTCC
           AGAA TGGGG CCTG  CC GAGCGGGC GAGCAGCTCCGCCTCGC GT    GATTTCC
-MEXICO    AGAACTGGGGCCTGATCCGGAGCGGGCAGAGCAGCTCCGCCTCGCCGTGCAGGATTTCC 4930v     4940v     4950v     4960v     4970v     4980v
-BURMA     TCCGCAAGCTCACGAATGTAGCTCAGATGTGTGTGGATGTTGTTTCCCGTGTTTATGGGG
           TCCG A G T ACGAATGT GC CAGAT TGTGT GA GT GT TC  G GTTTA GGGG
-MEXICO    TCCGTAGGTTAACGAATGTGGCCCAGATTTGTGTTGAGGTGGTGTCTAGAGTTTACGGGG 4990v     5000v     5010v     5020v     5030v     5040v
-BURMA     TTTCCCCTGGACTCGTTCATAACCTGATTGGCATGCTACAGGCTGTTGCTGATGGCAAGG
           TTTCCCC GG CT GTTCATAACCTGAT GGCATGCT CAG CT TTG TGATGG AAGG
-MEXICO    TTTCCCCGGGTCTGGTTCATAACCTGATAGGCATGCTCCAGACTATTGGTGATGGTAAGG 5050v     5060v     5070v     5080v     5090v     5100v
-BURMA     CACATTTCACTGAGTCAGTAAAACCAGTGCTGACTTGACAAATTCAATCTTGTGTCGGG
           C CATTT AC GAGTC GT AA CC   T CT GAC T ACA A TCAAT  TG   CGG
-MEXICO    CGCATTTTACAGAGTCTGTTAAGCCTATACTTGACCTTACACACTCAATTATGCACCGGT 5110v     5120v     5130v     5140v     5150v     5160v
-BURMA     TGGAATGAATAACATGTCTTTTGCTGCGCCCATGGGTTCGCGACCATGCGCCCTCGGCCT
              GAATGAATAACATGT    TTTTGCTGCGCCCATGGGTTCGC ACCATGCGCCCT GGCCT
-MEXICO    CTGAATGAATAACATGTGGTTTGCTGCGCCCATGGGTTCGCCACCATGCGCCCTAGGCCT 5170v     5180v     5190v     5200v     5210v     5220v
-BURMA     ATTTTGTTGCTGCTCCTCATGTTTTTGCCTATGCTGCCCGCGCCACCGCCCGGTCAGCCG
            TTTTG TG TG TCCTC TGTTT  TGCCTATG TGCCCGCGCCACCG CCGGTCAGCCG
-MEXICO    CTTTTGCTGTTGTTCCTCTTGTTTCTGCCTATGTTGCCCGCGCCACCGACCGGTCAGCCG 5230v     5240v     5250v     5260v     5270v     5280v
-BURMA     TCTGGCCGCCGTCGTGGGCGGCGCAGCGGCGGTTCCGGCGGTGGTTTCTGGGGTGACGGG
           TCTGGCCGCCGTCGTGGGCGGCGCAGCGGCGGT  CCGGCGGTGGTTTCTGGGGTGACCGG
-MEXICO    TCTGGCCGCCGTCGTGGGCGGCGCAGCGGCGGTACCGGCGGTGGTTTCTGGGGTGACCGG 5290v     5300v     5310v     5320v     5330v     5340v
-BURMA     GTTGATTCTCAGCCCTTCGCAATCCCCTATATTCATCCAACCAACCCCTTCGCCCCCGAT
           GTTGATTCTCAGCCCTTCGCAATCCCCTATATTCATCCAACCAACCCCTT GCCCC GA
-MEXICO    GTTGATTCTCAGCCCTTCGCAATCCCCTATATTCATCCAACCAACCCCTTTGCCCCAGAC 5350v     5360v     5370v     5380v     5390v     5400v
-BURMA     GTCACCGCTGCGGCCGGGGCTGGACCTCGTGTTCGCCAACCCGCCCGACCACTCGGCTCC
           GT   CCGCTGCG CCGGG CTGGACCTCG  TTCGCCAACC GCCCG CCACT GGCTCC
-MEXICO    GTTGCCGCTGCGTCCGGGTCTGGACCTCGCCTTCGCCAACCAGCCCGGCCACTTGGCTCC 5410v     5420v     5430v     5440v     5450v     5460v
-BURMA     GCTTGGCGTGACCAGGCCCAGCGCCCCGCCGTTGCCTCACGTCGTAGACCTACCACAGCT
            CTTGGCG GA CAGGCCCAGCGCCCC CCG TGCCTC CGTCG  GACCT CCACAGC
-MEXICO    ACTTGGCGAGATCAGGCCCAGCGCCCCTCCGCTGCCTCCCGTCGCCGACCTGCCACAGCC 5470v     5480v     5490v     5500v     5510v     5520v
-BURMA     GGGGCCGCGCCGCTAACCGCGGTCGCTCCGGCCCATGACACCCCGCCAGTGCCTGATGTC
           GGGGC GCG CGCT AC GC GT GC CC GCCCATGACACC C CC GT CC GA GT
-MEXICO    GGGGCTGCGGCGCTGACGGCTGTGGCGCCTGCCCATGACACCTCACCCGTCCCGGACGTT 5530v     5540v     5550v     5560v     5570v     5580v
-BURMA     GACTCCCGCGGCGCCATCTTGCGCCGGCAGTATAACCTATCAACATCTCCCCTTACCTCT
           GA TC CGCGG GC AT  T CGCCG CAGTATAA  T TC AC TC CCCCT AC TC
-MEXICO    GATTCTCGCGGTGCAATTCTACGCCGCCAGTATAATTTGTCTACTTCACCCCTGACATCC 5590v     5600v     5610v     5620v     5630v     5640v
-BURMA     TCCGTGGCCACCGGCACTAACCTGGTTCTTTATGCCGCCCCTCTTAGTCCGCTTTTACCC
           TC GTGGCC C GGCACTAA  T GT CT TATGC GCCCC CTTA TCCGC T T CC
-MEXICO    TCTGTGGCCTCTGGCACTAATTTAGTCCTGTATGCAGCCCCCCTTAATCCGCCTCTGCCG
```

```
                    5650v      5660v      5670v      5680v      5690v      5700v
-BURMA     CTTCAGGACGGCACCAATACCCATATAATGGCCACGGAAGCTTCTAATTATGCCCAGTAC
           CT CAGGACGG AC AATAC CA AT ATGGCCAC GA GC TC AATTATGC CAGTAC
-MEXICO    CTGCAGGACGGTACTAATACTCACATTATGGCCACAGAGGCCTCCAATTATGCACAGTAC 5710v      5720v      5730v      5740v      5750v      5760v
-BURMA     CGGGTTGCCCGTGCCACAATCCGTTACCGCCCGCTGGTCCCCAATGCTGTCGGCGGTTAC
           CGGGTTGCCCG GC AC ATCCGTTACCG CC CT GT CC AATGC GT GG GG TA
-MEXICO    CGGGTTGCCCGCGCTACTATCCGTTACCGGCCCCTAGTGCCTAATGCAGTTGGAGGCTAT 5770v      5780v      5790v      5800v      5810v      5820v
-BURMA     GCCATCTCCATCTCATTCTGGCCACAGACCACCACCACCCCGACGTCCGTTGATATGAAT
           GC AT TCCAT TC TTCTGGCC CA AC ACCAC ACCCC AC TC GTTGA ATGAAT
-MEXICO    GCTATATCCATTTCTTTCTGGCCTCAAACAACCACAACCCCTACATCTGTTGACATGAAT 5830v      5840v      5350v      5850v      5870v      5880v
-BURMA     TCAATAACCTCGACGGATGTTCGTATTTTAGTCCAGCCCGGCATAGCCTCTGAGCTTGTG
           TC AT AC TC AC GATGT  G ATT T GT CA CC GGCATAGC TCTGA  T GT
-MEXICO    TCCATTACTTCCACTGATGTCAGGATTCTTGTTCAACCTGGCATAGCATCTGAATTGGTC 5890v      5900v      5910v      5920v      5930v      5940v
-BURMA     ATCCCAAGTGAGCGCCTACACTATCGTAACCAAGGCTGGCGCTCCGTCGAGACCTCTGGG
           ATCCCAAG GAGCGCCT CACTA CG AA CAAGG TGGCGCTC GT GAGAC TCTGG
-MEXICO    ATCCCAAGCGAGCGCCTTCACTACCGCAATCAAGGTTGGCGCTCGGTTGAGACATCTGGT 5950v      5960v      5970v      5980v      5990v      6000v
-BURMA     GTGGCTGAGGAGGAGGCTACCTCTGGTCTTGTTATGCTTTGCATACATGGCTCACTCGTA
           GT GCTGAGGAGGA GC ACCTC GGTCTTGT ATG T TGCATACATGGCTC C  GT
-MEXICO    GTTGCTGAGGAGGAAGCCACCTCCGGTCTTGTCATGTTATGCATACATGGCTCTCCAGTT 6010v      6020v      6030v      6040v      6050v      6060v
-BURMA     AATTCCTATACTAATACACCCTATACCGGTGCCCTCGGGCTGTTGGACTTTGCCCTTGAG
           AA TCCTATAC AATAC CC TATACCGGTGCCCT GG  T  TGGACTTTGCC T GAG
-MEXICO    AACTCCTATACCAATACCCCTTATACCGGTGCCCTTGGCTTACTGGACTTTGCCTTAGAG 6070v      6080v      6090v      6100v      6110v      6120v
-BURMA     CTTGAGTTTCGCAACCTTACCCCCGGTAACACCAATACGCGGGTCTCCCGTTATTCCAGC
           CTTGAGTTTCGCAA CT ACC CC GTAACACCAATAC CG GT TCCCGTTA TCCAGC
-MEXICO    CTTGAGTTTCGCAATCTCACCACCTGTAACACCAATACACGTGTGTCCCGTTACTCCAGC 6130v      6140v      6150v      6160v      6170v      6180v
-BURMA     ACTGCTCGCCACCGCCTTCGTCGCGGTGCGGACGGGACTGCCGAGCTCACCACCACGGCT
           ACTGCTCG CAC  C   CG G G    GACGGGACTGC GAGCT ACCAC AC GC
-MEXICO    ACTGCTCGTCACTCCGCCCGAGGGGCC---GACGGGACTGCGGAGCTGACCACAACTGCA 6190v      6200v      6210v      6220v      6230v      6240v
-BURMA     GCTACCCGCTTTATGAAGGACCTCTATTTTACTAGTACTAATGGTGTCGGTGAGATCGGC
           GC ACC G TT ATGAA GA CTC A TTTAC  G   TAATGG GT GGTGA TCGGC
-MEXICO    GCCACCAGGTTCATGAAAGATCTCCACTTTACCGGCCTTAATGGGGTAGGTGAAGTCGGC 6250v      6260v      6270v      6280v      6290v      6300v
-BURMA     CGCGGGATAGCCCTCACCCTGTTCAACCTTGCTGACACTCTGCTTGGCGGCCTGCCGACA
           CGCGGGATAGC CT AC  T  T AACCTTGCTGACAC CT CT GGCGG CT CCGACA
-MEXICO    CGCGGGATAGCTCTAACATTACTAACCTTGCTGACACGCTCCTCGGCGGGCTCCCGACA 6310v      6320v      6330v      6340v      6350v      6360v
-BURMA     GAATTGATTTCGTCGGCTGGTGGCCAGCTGTTCTACTCCCGTCCCGTTGTCTCAGCCAAT
           GAATT ATTTCGTCGGCTGG GG CA CTGTT TA TCCCG CC GTTGTCTCAGCCAAT
-MEXICO    GAATTAATTTCGTCGGCTGGCGGGCAACTGTTTTATTCCCGCCGGTTGTCTCAGCCAAT 6370v      6350v      6390v      6400v      6410v      6420v
-BURMA     GGCGAGCCGACTGTTAAGTTGTATACATCTGTAGAGAATGCTCAGCAGGATAAGGGTATT
           GGCGAGCC AC GT AAG T TATACATC GT GAGAATGCTCAGCAGGATAAGGGT TT
-MEXICO    GGCGAGCCAACCGTGAAGCTCTATACATCAGTGGAGAATGCTCAGCAGGATAAGGGTGTT 6430v      6440v      6450v      6460v      6470v      6480v
-BURMA     GCAATCCCGCATGACATTGACCTCGGAGAATCTCGTGTGGTTATTCAGGATTATGATAAC
           GC ATCCC CA GA AT GA CT GG GA TC CGTGTGGT ATTCAGGATTATGA AAC
-MEXICO    GCTATCCCCACGATATCGATCTTGGTGATTCGCGTGTGGTCATTCAGGATTATGACAAC 6490v      6500v      6510v      6520v      6530v      6540v
-BURMA     CAACATGAACAAGATCGGCCGACGCCTTCTCCAGCCCCATCGCGCCCTTTCTCTGTCCTT
           CA CATGA CA GATCGGCC AC CC TC CC GC CCATC CG CCTTT TCTGT CT
-MEXICO    CAGCATGAGCAGGATCGGCCCACCCCGTCGCCTGCGCCATCTCGGCCTTTTTCTGTTCTC 6550v      6560v      6570v      6580v      6590v      6600v
-BURMA     CGAGCTAATGATGTGCTTTGGCTCTCTCTCACCGCTGCCGAGTATGACCAGTCCACTTAT
           CGAGC AATGATGT CTTTGGCT TC CTCAC GC GCCGAGTATGACCAGTCCACTTA
-MEXICO    CGAGCAAATGATGTACTTTGGCTGTCCCTCACTGCAGCCGAGTATGACCAGTCCACTTAC
```

-continued

```
            6610v      6620v      6630v      6640v      6650v      6660v
-BURMA      GGCTCTTCGACTGGCCCAGTTTATGTTTCTGACTCTGTGACCTTGGTTAATGTTGCGACC
            GG TC TC ACTGGCCC GTTTAT T TC GAC   GTGAC TTGGT AATGTTGCGAC
-MEXICO     GGGTCGTCAACTGGCCCGGTTTATATCTCGGACAGCGTGACTTTGGTGAATGTTGCGACT 6670v      6680v      6690v      6700v      6710v      6720v
-BURMA      GGCGCGCAGGCCGTTGCCCGGTCGCTCGATTGGACCAAGGTCACACTTGACGGTCGCCCC
            GGCGCGCAGGCCGT GCCCG TCGCT GA TGG CCAA GTCAC CT GACGG CG CCC
-MEXICO     GGCGCGCAGGCCGTAGCCCGATCGCTTGACTGGTCCAAAGTCACCCTCGACGGGCGGCCC 6730v      6740v      6750v      6760v      6770v      6780v
-BURMA      CTCTCCACCATCCAGCAGTACTCGAAGACCTTCTTTGTCCTGCCGCTCCGCGGTAAGCTC
            CTC C AC  T   AGCA TA TC AAGAC TTCTTTGT CT CC CT CG GG AAGCTC
-MEXICO     CTCCCGACTGTTGAGCAATATTCCAAGACATTCTTTGTGCTCCCCCTTCGTGGCAAGCTC 6790v      6800v      6810v      6820v      6830v      6840v
-BURMA      TCTTTCTGGGAGGCAGGCACAACTAAAGCCGGGTACCCTTATAATTATAACACCACTGCT
            TC TT TGGGAGGC GGCACAAC AAAGC GG TA CCTTATAATTATAA AC ACTGCT
-MEXICO     TCCTTTTGGGAGGCCGGCACAACAAAAGCAGGTTATCCTTATAATTATAATACTACTGCT 6850v      6860v      6870v      6880v      6890v      6900v
-BURMA      AGCGACCAACTGCTTGTCGAGAATGCCGCCGGGCACCGGGTCGCTATTTCCACTTACACC
            AG GACCA    T CT  T GA AATGC GCCGG CA CGGGTCGC ATTTC AC TA ACC
-MEXICO     AGTGACCAGATTCTGATTGAAAATGCTGCCGGCCATCGGGTCGCCATTTCAACCTATACC 6910v      6920v      6930v      6940v      6950v      6960v
-BURMA      ACTAGCCTGGGTGCTGGTCCCGTCTCCATTTCTGCGGTTGCCGTTTTAGCCCCCCACTCT
            AC AG CT GG GC GGTCC GTC CCATTTCTGCGG  GC GTTTT GC CC C CTC
-MEXICO     ACCAGGCTTGGGGCCGGTCCGGTCGCCATTTCTGCGGCCGCGGTTTTGGCTCCACGCTCC 6970v      6980v      6990v      7000v      7010v      7020v
-BURMA      GCGCTAGCATTGCTTGAGGATACCTTGGACTACCCTGCCCGCGCCCATACTTTTGATGAT
            GC CT GC   TGCT GAGGATAC TT GA TA CC G   CG GC CA AC TTTGATGA
-MEXICO     GCCCTGGCTCTGCTGGAGGATACTTTTGATTATCCGGGGCGGGCGCACACATTTGATGAC 7030v      7040v      7050v      7060v      7070v      7080v
-BURMA      TTCTGCCCAGAGTGCCGCCCCCTTGGCCTTCAGGGCTGCGCTTTCCAGTCTACTGTCGCT
            TTCTGCCC GA TGCCGC C   T GGCCT CAGGG TG GCTTTCCAGTC ACTGTCGCT
-MEXICO     TTCTGCCCTGAATGCCGCGCTTTAGGCCTCCAGGGTTGTGCTTTCCAGTCAACTGTCGCT 7090v      7100v      7110v      7120v      7130v      7140v
-BURMA      GAGCTTCAGCGCCTTAAGATGAAGGTGGGTAAAACTCGGGAGTTGTAGTTTATTTGCTTG
            GAGCT CAGCGCCTTAA   T AAGGTGGGTAAAACTCGGGAGTTGTAGTTTATTTG  TG
-MEXICO     GAGCTCCAGCGCCTTAAAGTTAAGGTGGGTAAAACTCGGGAGTTGTAGTTTATTTGGCTG 7150v      7160v                 7170v      7180v      7190v
-BURMA      TGCCCCCCTTCTTTCTGTTGC---------TTATTTCTCATTTCTGCGTTCCGCGCTCCC
            TGCCC CCT CTT    TGC         TTATTTC   TTTCT GT CCGCGCTCCC
-MEXICO     TGCCCACCTACTTATATCTGCTGATTTCCTTTATTTCCTTTTTCTCGGTCCCGCGCTCCC v 7195
-BURMA      TGA
            TGA
-MEXICO     TGA
```

A number of open reading frames, which are potential coding regions, have been found within the DNA sequences set forth above. As has already been noted, consensus residues for the RNA-directed RNA polymerase (RDRP) were identified in the HEV (Burma) strain clone ET1.1. Once a contiguous overlapping set of clones was accumulated, it became clear that the nonstructural elements containing the RDRP as well as what were identified as consensus residues for the helicase domain were located in the first large open reading frame (ORFI). ORFI covers the 5' half of the genome and begins at the first encoded met, after the 27th bp of the apparent non-coding sequence, and then extends 5079 bp before reaching a termination codon. Beginning 37 bp downstream from the ORFI stop codon in the plus 1 frame is the second major opening reading frame (ORF2) extending 1980 bp and terminating 68 bp upstream from the point of poly A addition. The third forward ORF (in the plus 2 frame) is also utilized by HEV. ORF3 is only 370 bp in length and would not have been predicted to be utilized by the virus were it not for the identification of the immunoreactive cDNA clone 406.4-2 from the Mexico SISPA cDNA library (see below for detailed discussion). This epitope confirmed the utilization of ORF3 by the virus, although the means by which this ORF is expressed has not yet been fully elucidated. If we assume that the first met is utilized, ORF3 overlaps ORF1 by 1 bp at its 5' end and ORF2 by 328 bp at its 3'end. ORF2 contains the broadly reactive 406.3-2 epitope and also a signal sequence at its extreme 5' end. The first half of this ORF2 also has a high pI value (>10) similar to that seen with other virus capsid proteins. These data suggest that the ORF2 might be the predominant structural gene of HEV.

The existence of subgenomic transcripts prompted a set of experiments to determine whether these RNAs were produced by splicing from the 5' end of the genome. An analysis using subgenomic probes from throughout the genome, including the extreme 5' end, did not provide evidence for a spliced transcript. However, it was discovered that a region of the genome displayed a high degree of homology with a 21 bp segment identified in Sindbis as a probably internal initiation site for RNA transcription used in the production of its subgenomic messages. Sixteen of 21 (76%) of the nucleotides are identical.

Two cDNA clones which encode an epitope of HEV that is recognized by sera collected from different ET-NANB outbreaks (i.e., a universally recognized epitope) have been isolated and characterized. One of the clones immunoreacted with 8 human sera from different infected individuals and the other clone immunoreacted with 7 of the human sera tested. Both clones immunoreacted specifically with cyno sera from infected animals and exhibited no immunologic response to sera from uninfected animals. The sequences of the cDNAs in these recombinant phages, designated 406.3-2 and 406.4-2 have been determined. The HEV open reading frames are shown to encode epitopes specifically recognized by sera from patients with HEV infections. The cDNA sequences and the polypeptides that they encode are set forth below.

Epitopes derived from Mexican strain of HEV:

406;4-2 sequence (nucleotide sequence has SEQ ID NO.13; amino acid sequence has SEQ ID NO.14).

406.3-2 sequence (nucleotide sequence has SEQ ID NO:15; amino acid sequence has SEQ ID NO:16):

The universal nature of these epitopes is evident from the homology exhibited by the DNA that encodes them. If the epitope coding sequences from the Mexican strains shown above are compared to DNA sequences from other strains, such as the Burmese strain also set forth above, similarities are evident, as shown in the following comparisons.

Comparison of 406.4-2 epitopes, HEV Mexico and Burma strains:

```
                           10        20        30
MEXICAN   (SEQ ID NO.17)   ANQPGHLAPLGEIRPSAPPLPPVADLPQPGLRR
                           ::..:.: ::::  .:::::::::.:.:::: : ::
BURMA     (SEQ ID NO.18)   ANPPDHSAPLGVTRPSAPPLPHVVDLPQLGPRR
                           10        20        30
```

There is 73.5% identity in a 33-amino acid overlap.
Comparison of 406.3-2 epitopes, HEV Mexico and Burma strains: MEXICAN(SEQ ID No.19)

```
       10        20        30        40
TFDYPGRAHTFDDFCPECRALGLQGCAFQSTVAELQRLKVKV
:.::::.::::::::::::::.:::::::::::::::::.::
TLDYPARAHTFDDFCPECRPLGLQGCAFQSTVAELQRLKMKV
       10        20        30        40
```

BURMA (SEQ ID No.20)
There is 90.5% identity in the 42-amino acid overlap.

It will be recognized by one skilled in the art of molecular genetics that each of the specific DNA sequences given above shows a corresponding complementary DNA sequence as well as RNA sequences corresponding to both the principal sequence shown and the complementary DNA sequence. Additionally, open reading frames encoding peptides are present, and expressible peptides are disclosed by the nucleotide sequences without setting forth the amino acid sequences explicitly, in the same manner as if the amino acid sequences were explicitly set forth as in the ET1.1 sequence or other sequences above.

DETAILED DESCRIPTION OF THE INVENTION

I. Definitions

The terms defined below have the following meaning herein:

1. "Enterically transmitted non-A/non-B hepatitis viral agent, ET-NANB, or HEV" means a virus, virus type, or virus class which (1) causes water-borne, infectious hepatitis, (ii) is transmissible in cynomolgus monkeys, (iii) is serologically distinct from hepatitis A virus (HAV), hepatitis B virus (HBV), hepatitis C virus (HCV), and hepatitis D virus, and (iv) includes a genomic region which is homologous to the 1.33 kb cDNA insert in plasmid pTZKF1 (ET1.1) carried in *E. coli* strain BB4 identified by ATCC deposit number 67717.

2. Two nucleic acid fragments are "homologous" if they are capable of hybridizing to one another under hybridization conditions described in Maniatis et al., op. cit., pp. 320–323. However, using the following wash conditions: 2× SCC, 0.1% SDS, room temperature twice, 30 minutes each; then 2×SCC, 0.1% SDS, 50° C. once, 30 minutes; then 2×SCC, room temperature twice, 10 minutes each, homologous sequences can be identified that contain at most about 25–30% basepair mismatches. More preferably, homologous nucleic acid strands contain 15–25% basepair mismatches, even more preferably 5–15% basepair mismatches. These degrees of homology can be selected by using more stringent wash conditions for identification of clones from gene libraries (or other sources of genetic material), as is well known in the art.

3. Two amino acid sequences or two nucleotide sequences (in an alternative definition for homology between two nucleotide sequences) are considered homologous (as this term is preferably used in this specification) if they have an alignment score of >5 (in standard deviation units) using the program ALIGN with the mutation gap matrix and a gap penalty of 6 or greater. See Dayhoff, M. O., in *Atlas of Protein Sequence and Structure* (1972) Vol. 5, National Biomedical Research Foundation, pp. 101–110, and Supplement 2 to this volume, pp. 1–10. The two sequences (or parts thereof, preferably at least 30 amino acids in length) are more preferably homologous if their amino acids are greater than or equal to 50% identical when optimally aligned using the ALIGN program mentioned above.

4. A DNA fragment is "derived from" an ET-NANB viral agent if it has the same or substantially the same basepair sequence as a region of the viral agent genome.

5. A protein is "derived from" an ET-NANB viral agent if it is encoded by an open reading frame of a DNA or RNA fragment derived from an ET-NANB viral agent.

II. Obtaining Cloned ET-NANB Fragments

According to one aspect of the invention, it has been found that a virus-specific DNA clone can be produced by (a) isolating RNA from the bile of a cynomolgus monkey having a known ET-NANB infection, (b) cloning the cDNA fragments to form a fragment library, and (c) screening the library by differential hybridization to radiolabeled cDNAs from infected and non-infected bile sources.

A. cDNA Fragment Mixture

ET-NANB infection in cynomolgus monkeys is initiated by inoculating the animals intravenously with a 10% w/v suspension from human case stools positive for 27–34 nm ET-NANB particles (mean diameter 32 nm). An infected animal is monitored for elevated levels of alanine aminotransferase, indicating hepatitis infection. ET-NANB infection is confirmed by immunospecific binding of seropositive antibodies to virus-like particles (VLPs), according to published methods (Gravelle). Briefly, a stool (or bile)

specimen taken from the infected animal 3–4 weeks after infection is diluted 1:10 with phosphate-buffered saline, and the 10t suspension is clarified by low-speed centrifugation and filtration successively through 1.2 and 0.45 micron filters. The material may be further purified by pelleting through a 30% sucrose cushion (Bradley). The resulting preparation of VLPs is mixed with diluted serum from human patients with known E--NANB infection. After incubation overnight, the mixture is centrifuged overnight to pellet immune aggregates, and these are stained and examined by electron microscopy for antibody binding to the VLPs.

ET-NANB infection can also be confirmed by seroconversion to VLP-positive serum. Here the serum of the infected animal is mixed as above with 27–34 nm VLPs isolated from the stool specimens of infected human cases and examined by immune electron microscopy for antibody binding to the VLPs.

Bile can be collected from ET-NANB positive animals by either cannulating the bile duct and collecting the bile fluid or by draining the bile duct during necropsy. Total RNA is extracted from the bile by hot phenol extraction, as outlined in Example 1A. The RNA fragments are used to synthesize corresponding duplex cDNA fragments by random priming, also as referenced in Example 1A. The cDNA fragments may be fractionated by gel electrophoresis or density gradient centrifugation to obtain a desired size class of fragments, e.g., 500–4,000 basepair fragments.

Although alternative sources of viral material, such as VLPs obtained from stool samples (as described in Example 4), may be used for producing a CDNA fraction, the bile source is preferred. According to one aspect of the invention, it has been found that bile from ET-NANB-infected monkeys shows a greater number of intact viral particles than material obtained from stool samples, as evidenced by immune electron microscopy. Bile obtained from an ET-NANB infected human or cynomolgus macaque, for use as a source of ET-NANB viral protein or genomic material, or intact virus, forms part of the present invention.

B. cDNA Library and Screening

The cDNA fragments from above are cloned into a suitable cloning vector to form a cDNA library. This may be done by equipping blunt-ended fragments with a suitable end linker, such as an EcoRI sequence, and inserting the fragments into a suitable insertion site of a cloning vector, such as at a unique EcoRI site. After initial cloning, the library may be re-cloned, if desired, to increase the percentage of vectors containing a fragment insert. The library construction described in Example 1B is illustrative. Here cDNA fragments were blunt-ended, equipped with EcoRI ends, and inserted into the EcoRI site of the lambda phage vector gt10. The library phage, which showed less than 5% fragment inserts, was isolated, and the fragment inserts re-cloned into the lambda gt10 vector, yielding more than 95% insert-containing phage.

The cDNA library is screened for sequences specific for ET-NANB by differential hybridization to cDNA probes derived from infected and non-infected sources. cDNA fragments from infected and non-infected source bile or stool viral isolates can be prepared as above. Radiolabeling the fragments is by random labeling, nick translation, or end labeling, according to conventional methods (Maniatis, p. 109). The CDNA library from above is screened by transfer to duplicate nitrocellulose filters, and hybridization with both infected-source and non-infected-source (control) radiolabeled probes, as detailed in Example 2. In order to recover sequences that hybridize at the preferred outer limit of 25–30% basepair mismatches, clones can be selected if they hybridize under the conditions described in Maniatis et al., op. cit., pp. 320–323, but using the following wash conditions: 2×SCC, 0.1% SDS, room temperature—twice, 30 minutes each; then 2×SCC, 0.1% SDS, 50° C.—once, 30 minutes; then 2× SCC, room temperature—twice, 10 minutes each. These conditions allowed identification of the Mexican isolate discussed above using the ET1.1 sequence as a probe. Plaques which show selective hybridization to the infected-source probes are preferably re-plated at low plating density and re-screened as above, to isolate single clones which are specific for ET-NANB sequences. As indicated in Example 2, sixteen clones which hybridized specifically with infected-source probes were identified by these procedures. One of the clones, designated lambda gt101.1, contained a 1.33 kilobase fragment insert.

C. ET-NANB Sequences

The basepair sequence of cloned regions of the ET-NANB fragments from Part B are determined by standard sequencing methods. In one illustrative method, described in Example 3, the fragment insert from the selected cloning vector is excised, isolated by gel electrophoresis, and inserted into a cloning vector whose basepair sequence on either side of the insertion site is known. The particular vector employed in Example 3 is a pTZKF1 vector shown at the left in FIG. 1. The ET-NANB fragment from the gt10-1.1 phage was inserted at the unique EcoRI site of the pTZKF1 plasmid. Recombinants carrying the desired insert were identified by hybridization with the isolated 1.33 kilobase fragment, as described in Example 3. One selected plasmid, identified as pTZKF1 (ET1.1), gave the expected 1.33 kb fragment after vector digestion with EcoRI. *E. coli* strain BB4 infected with the pTZKF1(ET1.1) plasmid has been deposited with the American Type Culture Collection, Rockville, Md., and is identified by ATCC deposit number 67717.

The pTZKF1(ET1.1) plasmid is illustrated at the bottom in FIG. 1. The fragment insert has 5' and 3' end regions denoted at A and C, respectively, and an intermediate region, denoted at B. The sequences in these regions were determined by standard dideoxy sequencing and were set forth in an earlier application in this series. The three short sequences (A, B, and C) are from the same insert strand. As will be seen in Example 3, the B-region sequence was actually determined from the opposite strand, so that the B region sequence shown above represents the complement of the sequence in the sequenced strand. The base numbers of the partial sequences are approximate.

Later work in the laboratory of the inventors identified the full sequence, set forth above. Fragments of this total sequence can readily be prepared using restriction endonucleases. Computer analysis of both the forward and reverse sequence has identified a number of cleavage sites.

III. ET-NANB Fragments

According to another aspect, the invention includes ET-NANB-specific fragments or probes which hybridize with ET-NANB genomic sequences or cDNA fragments derived therefrom. The fragments may include full-length cDNA fragments such as described in Section II, or may be derived from shorter sequence regions within cloned cDNA fragments. Shorter fragments can be prepared by enzymatic digestion of full-length fragments under conditions which yield desired-sized fragments, is will be described in Section IV. Alternatively, the fragments can be produced by oligonucleotide synthetic methods, using sequences derived from the cDNA fragments. Methods or commercial services for producing selected-sequence oligonucleotide fragments are available. Fragments are usually at least 12 nucleotides in length, preferably at least 14, 20, 30 or 50 nucleotides, when used as probes. Probes can be full length or less than 500, preferably less than 300 or 200, nucleotides in length.

To confirm that a given ET-NANB fragment is in fact derived from the ET-NANB viral agent, the fragment can be shown to hybridize selectively with cDNA from infected sources. By way of illustration, to confirm that the 1.33 kb fragment in the pTZKF1(ET1.1) plasmid is ET-NANB in origin, the fragment was excised from the pTZKF1(ET1.1) plasmid, purified, and radiolabeled by random labeling. The radiolabeled fragment was hybridized with fractionated cDNAs from infected and non-infected sources to confirm that the probe reacts only with infected-source cDNAs. This method is illustrated in Example 4, where the above radiolabeled 1.33 kb fragment from pTZKF1(ET1.1) plasmld was examined for binding to cDNAs prepared from infected and non-infected sources. The infected sources are (1) bile from a cynomolgus macaque infected with a strain of virus derived from stool samples from human patients from Burma with known ET-NANB infections and (2) a viral agent derived from the stool sample of a human ET-NANB patient from Mexico. The cDNAs in each fragment mixture were first amplified by a linker/primer amplification method described in Example 4. Fragment separation was on agarose gel, followed by Southern blotting and then hybridization to bind the radiolabeled 1.33 kb fragment to the fractionated cDNAs. The lane containing cDNAs from the infected sources showed a smeared band of bound probe, as expected (cDNAs amplified by the linker/primer amplification method would be expected to have a broad range of sizes). No probe binding to the amplified cDNAs from the non-infected sources was observed. The results indicate that the 1.33 kb probe is specific for cDNA fragments associated with ET-NANB infection. This same type of study, using ET 1.1 as the probe, has demonstrated hybridization to ET-NANB samples collected from Tashkent, Somalia, Borneo and Pakistan. Secondly, the fact that the probe is specific for ET-NANB related sequences derived from different continents (Asia, Africa and North America) indicates the cloned ET-NANB Burma sequence (ET1.1) is derived from a common ET-NANB virus or virus class responsible for ET-NANB hepatitis infection worldwide.

In a related confirmatory study, probe binding to fractionated genomic fragments prepared from human or cynomolgus macaque genomic DNA (both infected and uninfected) was examined. No probe binding was observed to either genomic fraction, demonstrating that the ET-NANB fragment is not an endogenous human or cynomolgus genomic fragment and additionally demonstrating that HEV is an RNA virus.

Another confirmation of ET-NANB specific sequences in the fragments is the ability to express ET-NANB proteins from coding regions in the fragments and to demonstrated specific sero-reactivity of these proteins with sera collected during documented outbreaks of ET-NANB. Section IV below discusses methods of protein expression using the fragments.

One important use of the ET-NANB-specific fragments is for identifying ET-NANB-derived cDNAs which contain additional sequence information. The newly identified cDNAs, in turn, yield new fragment probes, allowing further iterations until the entire viral genome is identified and sequenced. Procedures for identifying additional ET-NANB library clones and generating new probes therefrom generally follow the cloning and selection procedures described in Section II.

The fragments (and oligonucleotides prepared based on the sequences given above) are also useful as primers for a polymerase chain reaction method of detecting ET-NANB viral genomic material in a patient sample. This diagnostic method will be described in Section V below.

Two specific genetic sequences derived from the Mexican strain, identified herein as 406.3-2 and 406.4-2, have been identified that encode immunogenic epitopes. This was done by isolating clones which encode epitopes that immunologically react specifically with sera from individuals and experimental animals infected with HEV. Comparison of the isolated sequences with those in the Genebank collection of genetic sequences indicate that these viral sequences are novel. Since these sequences are unique, they can be used to identify the presence of HEV and to distinguish this strain of hepatitis from HAV, HBV, and HCV strains. The sequences are also useful for the design of oligonucleotide probes to diagnose the presence of virus in samples. They can be used for the synthesis of polypeptides that themselves are used in immunoassays. The specific 406.3-2 and 406.4-2 sequences can be incorporated into other genetic material, such as vectors, for ease of expression or replication. They can also be used (as demonstrated above) for identifying similar antigenic regions encoded by related viral strains, such as the Burmese strain.

IV. ET-NANB Proteins

As indicated above, ET-NANB proteins can be prepared by expressing open reading-frame coding regions in ET-NANB fragments. In one preferred approach, the ET-NANB fragments used for protein expression are derived from cloned cDNAs which have been treated to produce desired-size fragments, and preferably random fragments with sizes predominantly between about 100 to about 300 base pairs. Example 5 describes the preparation of such fragments by DNAs digestion. Because it is desired to obtain peptide antigens of between about 30 to about 100 amino acids, the digest fragments are preferably size fractionated, for example by gel electrophoresis, to select those in the approximately 100–300 basepair size range. Alternatively, cDNA libraries constructed directly from HEV-containing sources (e.g., bile or stool) can be screened directly if cloned into an appropriate expression vector (see below).

For example, the ET-NANB proteins expressed by the 406.3-2 and 406.4-2 sequences (and peptide fragments thereof) are particularly preferred since these proteins have been demonstrated to be immunoreactive with a variety of different human sera, thereby indicating the presence of one or more epitopes specific for HEV on their surfaces. These clones were identified by direct screening of a gt11 library.

A. Expression Vector

The ET-NANB fragments are inserted into a suitable expression vector. One exemplary expression vector is lambda gt11, which contains a unique EcoRI insertion site 53 base pairs upstream of the translation termination codon of the beta-galactosidase gene. Thus, the inserted sequence will be expressed as a beta-galactosidase fusion protein which contains the N-terminal portion of the beta-galactosidase gene, the heterologous peptide, and optionally the C-terminal region of the beta-galactosidase peptide (the C-terminal portion being expressed when the heterologous peptide coding sequence does not contain a translation termination codon). This vector also produces a temperature-sensitive repressor (c1857) which causes viral lysogeny at permissive temperatures, e.g., 32° C., and leads to viral lysis at elevated temperatures, e.g., 37° C. Advantages of this vector include: (1) highly efficient recombinant generation, (2) ability to select lysogenized host cells on the basis of host-cell growth at permissive, but not nonpermissive, temperatures, and (3) high levels of recombinant fusion protein production. Further, since phage containing a heterologous insert produces an inactive beta-galactosidase enzyme, phage with inserts can be readily identified by a beta-galactosidase colored-substrate reaction For insertion into the expression vector, the viral digest fragments may be modified, if needed, to contain selected restriction-site linkers, such as EcoRI linkers, according to conventional procedures. Example 1 illustrates methods for cloning the digest fragments into lambda gt11, which includes the steps of blunt-ending the fragments, ligating with EcoRI linkers, and introducing the fragments into EcoRI-cut lambda gt11. The resulting viral genomic library may be checked to confirm that a relatively large (representative) library has been produced. This can be done, in the case of the lambda gt11 vector, by infecting a suitable bacterial host, plating the bacteria, and examining the plaques for loss of beta-galactosidase activity. Using the procedures described in Example 1, about 50% of the plaques showed loss of enzyme activity.

B. Peptide Antigen Expression

The viral genomic library formed above is screened for production of peptide antigen (expressed as a fusion protein) which is immunoreactive with antiserum from ET-NANB seropositive individuals. In a preferred screening method, host cells infected with phage library vectors are plated, as above, and the plate is blotted with a nitrocellulose filter to transfer recombinant protein antigens produced by the cells onto the filter. The filter is then reacted with the ET-NANB antiserum, washed to remove unbound antibody, and reacted with reporter-labeled, anti-human antibody, which becomes bound to the filter, in sandwich fashion, through the anti-ET-NANB antibody.

Typically phage plaques which are identified by virtue of their production of recombinant antigen of interest are re-examined at a relatively low density for production of antibody-reactive fusion protein. Several recombinant phage clones which produced immunoreactive recombinant antigen were identified in the procedure.

The selected expression vectors may be used for scale-up production, for purposes of recombinant protein purification. Scale-up production is carried out using one of a variety of reported methods for (a) lysogenizing a suitable host, such as *E. coli,* with a selected lambda gt11 recombinant (b) culturing the transduced cells under conditions that yield high levels of the heterologous peptide, and (c) purifying the recombinant antigen from the lysed cells.

In one preferred method involving the above lambda gt11 cloning vector, a high-producer *E. coli* host, BNN103, is infected with the selected library phage and replica plated on two plates. One of the plates is grown at 32° C., at which viral lysogeny can occur, and the other at 42° C., at which the infecting phage is in a lytic stage and therefore prevents cell growth. Cells which grow at the lower but not the higher temperature are therefore assumed to be successfully lysogenized.

The lysogenized host cells are then grown under liquid culture conditions which favor high production of the fused protein containing the viral insert, and lysed by rapid freezing to release the desired fusion protein.

C. Peptide Purification

The recombinant peptide can be purified by standard protein purification procedures which may include differential precipitation, molecular sieve chromatography, ion-exchange chromatography, isoelectric focusing, gel electrophoresis and affinity chromatography. In the case of a fused protein, such as the beta-galactosidase fused protein prepared as above, the protein isolation techniques which are used can be adapted from those used in isolation of the native protein. Thus, for isolation of a soluble beta-galactosidase fusion protein, the protein can be isolated readily by simple affinity chromatography, by passing the cell lysis material over a solid support having surface-bound anti-beta-galactosidase antibody.

D. Viral Proteins

The ET-NANB protein of the invention may also be derived directly from the ET-NANB viral agent. VLPs or protein isolated from stool or liver samples from an infected individual, as above, are one suitable source of viral protein material. The VLPs isolated from the stool sample may be further purified by affinity chromatography prior to protein isolation (see below). The viral agent may also be raised in cell culture, which provides a convenient and potentially concentrated source of viral protein. For example, one might construct an immortalized trioma liver cell which supports NANB infection in cell culture. The trioma cell line is prepared by fusing human liver cells with a mouse/human fusion partner selected for human chromosome stability. Cells containing the desired NANB viral agent can be identified by immunofluorescence methods, employing anti-ET-NANB human antibodies.

The viral agent is disrupted, prior to protein isolation, by conventional methods, which can include sonication, high- or low-salt conditions, or use of detergents.

Purification of ET-NANB viral protein can be carried out by affinity chromatography, using a purified anti-ET-NANB antibody attached according to standard methods to a suitable solid support. The antibody itself may be purified by affinity chromatography, where an immunoreactive recombinant ETNANB protein, such as described above, is attached to a solid support, for isolation of anti-ET-NANB antibodies from an immune serum source. The bound antibody is released from the support by standard methods.

Alternatively, the anti-ET-NANB antibody may be an antiserum or a monoclonal antibody (Mab) prepared by immunizing a mouse or other animal with recombinant ETNANB protein. For Mab production, lymphocytes are isolated from the animal and immortalized with a suitable fusion partner, and successful fusion products which react with the recombinant protein immunogen are selected. These in turn may be used in affinity purification procedures, described above, to obtain native ET-NANB antigen.

V. Utility

Although ET-NANB is primarily of interest because of its effects on humans, recent data has shown that this virus is also capable of infecting other animals, especially mammals. Accordingly, any discussion herein of utility applies to both human and veterinary uses, especially commercial veterinary uses, such as the diagnosis and treatment of pigs, cattle, sheep, horses, and other domesticated animals.

A. Diagnostic Methods

The particles and antigens of the invention, as well as the genetic material, can be used in diagnostic assays. Methods for detecting the presence of ET-NANB hepatitis comprise analyzing a biological sample such as a blood sample, stool sample or liver biopsy specimen for the presence of an analyte associated with ET-NANB hepatitis virus.

The analyte can be a nucleotide sequence which hybridizes with a probe comprising a sequence of at least about 16 consecutive nucleotides, usually 30 to 200 nucleotides, up to substantially the full sequence of the sequences shown above (cDNA sequences). The analyte can be RNA or cDNA. The analyte is typically a virus particle suspected of being ET-NANB or a particle for which this classification is being ruled out. The virus particle can be further characterized as having an RNA viral genome comprising a sequence at least about 70% homologous to a sequence of at least 12 consecutive nucleotides of the "forward" and "reverse" sequences given above, usually at least about 80% homologous to at least about 60 consecutive nucleotides within the sequences, and may comprise a sequence substantially homologous to the full-length sequences. In order to detect an analyte, where the analyte hybridizes to a probe, the probe may contain a detectable label. Particularly preferred for use as a probe are sequences of consecutive nucleotides derived from the 406.3-2 and 406.4-2 clones described herein, since these clones appear to be particularly diagnostic for HEV.

The analyte can also comprise an antibody which recognizes an antigen, such as a cell surface antigen, on a ET-NANB virus particle. The analyte can also be a ET-NANB viral antigen. Where the analyte is an antibody or an antigen, either a labelled antigen or antibody, respectively, can be used to bind to the analyte to form an immunological complex, which can then be detected by means of the label.

Typically, methods for detecting analytes such as surface antigens and/or whole particles are based on immunoassays. Immunoassays can be conducted either to determine the presence of antibodies in the host that have arisen from infection by ET-NANB hepatitis virus or by assays that directly determine the presence of virus particles or antigens. Such techniques are well known and need not be described here in detail. Examples include both heterogeneous and homogeneous immunoassay techniques. Both techniques are based on the formation of an immunological complex between the virus particle or its antigen and a corresponding specific antibody. Heterogeneous assays for viral antigens typically use a specific monoclonal or polyclonal antibody bound to a solid surface. Sandwich assays are becoming increasingly popular. Homogeneous assays, which are carried out in solution without the presence of a solid phase, can also be used, for example by determining the difference in enzyme activity brought on by binding of free antibody to an enzyme-antigen conjugate. A number of suitable assays are disclosed in U.S. Pat. Nos. 3,817,837, 4,006,360, 3,996,345.

When assaying for the presence of antibodies induced by ET-NANB viruses, the viruses and antigens of the invention can be used as specific binding agents to detect either IgG or IgM antibodies. Since IgM antibodies are typically the first antibodies that appear during the course of an infection, when IgG synthesis may not yet have been initiated, specifically distinguishing between IgM and IgG antibodies present in the blood stream of a host will enable a physician or other investigator to determine whether the infection is recent or convalescent. Proteins expressed by the 406.3-2 and 406.4-2 clones described herein and peptide fragments thereof are particularly preferred for use as specific binding agents to detect antibodies since they have been demonstrated to be reactive with a number of different human HEV sera. Further, they are reactive with both acute and convalescent sera.

In one diagnostic configuration, test serum is reacted with a solid phase reagent having surface-bound ET-NANB protein antigen. After binding anti-ET-NANB antibody to the reagent and removing unbound serum components by washing, the reagent is reacted with reporter-labeled anti-human antibody to bind reporter to the reagent in proportion to the amount of bound anti-ET-NANB antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric or colorimetric substrate.

The solid surface reagent in the above assay prepared by known techniques for attaching protein material to solid support material, such as polymeric beads, dip sticks, or filter material. These attachment methods generally include non-specific adsorption of the protein to the support or covalent attachment of the protein, typically through a free amine group, to a chemically reactive group on the solid support, such as an activate carboxyl, hydroxyl, or aldehyde group.

In a second diagnostic configuration, known as a homogeneous assay, antibody binding to a solid support produces some change in the reaction medium which can be directly detected in the medium. Known general types of homogeneous assays proposed heretofore include (a) spin-labeled reporters, where antibody binding to the antigen is detected by a change in reported mobility (broadening of the spin splitting peaks), (b) fluorescent reporters, where binding is detected by a change in fluorescence efficiency, (c) enzyme reporters, where antibody binding effects enzyme/substrate interactions, and (d) liposome-bound reporters, where binding leads to liposome lysis and release of encapsulated reporter. The adaptation of these methods to the protein antigen of the present invention follows conventional methods for preparing homogeneous assay reagents.

In each of the assays described above, the assay method involves reacting the serum from a test individual with the protein antigen and examining the antigen for the presence of bound antibody. The examining may involve attaching a labeled anti-human antibody to the antibody being examined, either Igm (acute phase) or IgG (convalescent phase), and measuring the amount of reporter bound to the solid support, as in the first method, or may involve observing the effect of antibody binding on a homogeneous assay reagent, as in the second method.

Also forming part of the invention is an assay system or kit for carrying out the assay method just described. The kit generally includes a support with surface-bound recombinant protein antigen which is (a) immunoreactive with antibodies present in individuals infected with enterically transmitted nonA/nonB viral agent and (b) derived from a viral hepatitis agent whose genome contains a region which is homologous to the 1.33 kb DNA EcoRI insert present in plasmid pTZKF1(ET1.1) carried in *E. Coli* strain BB4, and having ATCC deposit no. 67717. A reporter-labeled anti-human antibody in the kit is used for detecting surface-bound anti-ET-NANB antibody.

B. Viral Genome Diagnostic Applications

The genetic material of the invention can itself be used in numerous assays as probes for genetic material present in naturally occurring infections. One method for amplification of target nucleic acids, for later analysis by hybridization assays, is known as the polymerase chain reaction or PCR technique. The PCR technique can be applied to detecting virus particles of the invention in suspected pathological samples using oligonucleotide primers spaced apart from each other and based on the genetic sequence set forth above. The primers are complementary to opposite strands of a double stranded DNA molecule and are typically separated by from about 50 to 450 nt or more (usually not more than 2000 nt). This method entails preparing the specific oligonucleotide primers and then repeated cycles of target DNA denaturation, primer binding, and extension with a DNA polymerase to obtain DNA fragments of the expected length based on the primer spacing. Extension products generated from one primer serve as additional target sequences for the other primer. The degree of amplification of a target sequence is controlled by the number of cycles that are performed and is theoretically calculated by the simple formula $2^n$ where n is the number of cycles. Given that the average efficiency per cycle ranges from about 65% to 85%, 25 cycles produce from 0.3 to 4.8 million copies of the target sequence. The PCR method is described in a number of publications, including Saiki et al., Science (1985) 230:1350–1354; Saiki et al., Nature (1986) 324:163–166; and Scharf et al., Science (1986) 233:1076–1078. Also see U.S. Pat. Nos. 4,683,194; 4,683,195; and 4,683,202.

The invention includes a specific diagnostic method for determination of ET-NANB viral agent, based on selective amplification of ET-NANB fragments. This method employs a pair of single-strand primers derived from non-homologous regions of opposite strands of a DNA duplex fragment, which in turn is derived from an enterically transmitted viral hepatitis agent whose genome contains a region which is homologous to the 1.33 kb DNA EcoRI insert present in plasmid pTZXF1(ET1.1) carried in E. coli strain BB4, and having ATCC deposit no. 67717. These "primer fragments," which form one aspect of the invention, are prepared from ET-NANB fragments such as described in Section III above. The method follows the process for amplifying selected nucleic acid sequences as disclosed in U.S. Pat. No. 4,683,202, as discussed above.

C. Peptide Vaccine

Any of the antigens of the invention can be used in preparation of a vaccine. A preferred starting material for preparation of a vaccine is the particle antigen isolated from bile. The antigens are preferably initially recovered as intact particles as described above. However, it is also possible to prepare a suitable vaccine from particles isolated from other sources or non-particle recombinant antigens. When non-particle antigens are used (typically soluble antigens), proteins derived from the viral envelope or viral capsid are preferred for use in preparing vaccines. These proteins can be purified by affinity chromatography, also described above.

If the purified protein is not immunogenic per se, it can be bound to a carrier to make the protein immunogenic. Carriers include bovine serum albumin, keyhole limpet hemocyanin and the like. It is desirable, but not necessary, to purify antigens to be substantially free of human protein. However, it is more important that the antigens be free of proteins, viruses, and other substances not of human origin that may have been introduced by way of, or contamination of, the nutrient medium, cell lines, tissues, or pathological fluids from which the virus is cultured or obtained.

Vaccination can be conducted in conventional fashion. For example, the antigen, whether a viral particle or a protein, can be used in a suitable diluent such as water, saline, buffered salines, complete or incomplete adjuvants, and the like. The immunogen is administered using standard techniques for antibody induction, such as by subcutaneous administration of physiologically compatible, sterile solutions containing inactivated or attenuated virus particles or antigens. An immune response producing amount of virus particles is typically administered per vaccinizing injection, typically in a volume of is one milliliter or less.

A specific example of a vaccine composition includes, in a pharmacologically acceptable adjuvant, a recombinant protein or protein mixture derived from an enterically transmitted nonA/nonB viral hepatitis agent whose genome contains a region which is homologous to the 1.33 kb DNA EcoRI insert present in plasmid pTZKF1(ET1.1) carried in E. coli strain BB4, and having ATCC deposit no. 67717. The vaccine is administered at periodic intervals until a significant titer of anti-ET-NANB antibody is detected in the serum. The vaccine is intended to protect against ET-NANB infection.

Particularly preferred are vaccines prepared using proteins expressed by the 406.3-2 and 406.4-2 clones described herein and equivalents thereof, including fragments of the expressed proteins. Since these clones have already been demonstrated to be reactive with a variety of human HEV-positive sera, their utility in protecting against a variety of HEV strains is indicated.

D. Prophylactic and Therapeutic Antibodies and Antisera

In addition to use as a vaccine, the compositions can be used be prepare antibodies to ET-NANB virus particles. The antibodies can be used directly as antiviral agents. To prepare antibodies, a host animal is immunized using the virus particles or, as appropriate, non-particle antigens native to the virus particle are bound to a carrier as described above for vaccines. The host serum or plasma is collected following an appropriate time interval to provide a composition comprising antibodies reactive with the virus particle. The gamma globulin fraction or the IgG antibodies can be obtained, for example, by use of saturated ammonium sulfate or DEAE Sephadex, or other techniques known to those skilled in the art. The antibodies are substantially free of many of the adverse side effects which may be associated with other anti-viral agents such as drugs.

The antibody compositions can be made even more compatible with the host system by minimizing potential adverse immune system responses. This is accomplished by removing all or a portion of the FC portion of a foreign species antibody or using an antibody of the same species as the host animal, for example, the use of antibodies from human/human hybridomas.

The antibodies can also be used as a means of enhancing the immune response since antibody-virus complexes are recognized by macrophages. The antibodies can be administered in amounts similar to those used for other therapeutic administrations of antibody. For example, pooled gamma globulin is administered at 0.02–0.1 ml/lb body weight during the early incubation of other viral diseases such as rabies, measles and hepatitis B to interfere with viral entry into cells. Thus, antibodies reactive with the ET-NANB virus particle can be passively administered alone or in conjunction with another anti-viral agent to a host infected with an ET-NANB virus to enhance the immune response and/or the effectiveness of an antiviral drug.

Alternatively, anti-ET-NANB-virus antibodies can be induced by administering anti-idiotype antibodies as immunogens. Conveniently, a purified anti-ET-NANB-virus antibody preparation prepared as described above is used to induce anti-idiotype antibody in a host animal. The composition is administered to the host animal in a suitable diluent. Following administration, usually repeated administration, the host produces anti-idiotype antibody. To eliminate an immunogenic response to the Fc region, antibodies produced by the same species as the host animal can be used or the Fc region of the administered antibodies can be removed. Following induction of anti-idiotype antibody in the host animal, serum or plasma is removed to provide an antibody composition. The composition can be purified as described above for anti-ET-NANB virus antibodies, or by affinity chromatography using anti-ET-NANB-virus antibodies bound to the affinity matrix. The anti-idiotype antibodies produced are similar in conformation to the authentic ET-NANB antigen and may be used to prepare an ET-NANB vaccine rather than using a ET-NANB particle antigen.

When used as a means of inducing anti-ET-NANB virus antibodies in a patient, the manner of injecting the antibody is the same as for vaccination purposes, namely intramuscularly, intraperitoneally, subcutaneously or the like in an effective concentration in a physiologically suitable diluent with or without adjuvant. One or more booster injections may be desirable. The anti-idiotype method of induction of anti-ET-NANB virus antibodies can alleviate problems which may be caused by passive administration of anti-ET-NANB-virus antibodies, such as an adverse immune response, and those associated with administration of purified blood components, such as infection with as yet undiscovered viruses.

The ET-NANB derived proteins of the invention are also intended for use in producing antiserum designed for pre- or post-exposure prophylaxis. Here an ET-NANB protein, or mixture of proteins is formulated with a suitable adjuvant and administered by injection to human volunteers, according to known methods for producing human antisera. Antibody response to the injected proteins is monitored, during a several-week period following immunization, by periodic serum sampling to detect the presence an anti-ET-NANB serum antibodies, as described in Section IIA above.

The antiserum from immunized individuals may be administered as a pre-exposure prophylactic measure for individuals who are at risk of contracting infection. The antiserum is also useful in treating an individual post-exposure, analogous to the use of high titer antiserum against hepatitis B virus for post-exposure prophylaxis.

E. Monoclonal Antibodies

For both in vivo use of antibodies to ET-NANB virus particles and proteins and anti-idiotype antibodies and diagnostic use, it may be preferable to use monoclonal antibodies. Monoclonal anti-virus particle antibodies or anti-idiotype antibodies can be produced as follows. The spleen or lymphocytes from an immunized animal are removed and immortalized or used to prepare hybridomas by methods known to those skilled in the art. To produce a human-human hybridoma, a human lymphocyte donor is selected. A donor known to be infected with a ET-NANB virus (where infection has been shown for example by the presence of anti-virus antibodies in the blood or by virus culture) may serve as a suitable lymphocyte donor. Lymphocytes can be isolated from a peripheral blood sample or spleen cells may be used if the donor is subject to splenectomy. Epstein-Barr virus (EBV) can be used to immortalize human lymphocytes or a human fusion partner can be used to produce human-human hybridomas. Primary in vitro immunization with peptides can also be used in the generation of human monoclonal antibodies.

Antibodies secreted by the immortalized cells are screened to determine the clones that secrete antibodies of the desired specificity. For monoclonal anti-virus particle antibodies, the antibodies must bind to ET-NANB virus particles. For monoclonal anti-idiotype antibodies, the antibodies must bind to anti-virus particle antibodies. Cells producing antibodies of the desired specificity are selected.

The following examples illustrate various aspects of the invention, but are in no way intended to limit the scope thereof.

MATERIAL

The materials used in the following Examples were as follows:

Enzymes: DNAse I and alkaline phosphatase were obtained from Boehringer Mannheim Biochemicals (BMB, Indianapolis, Ind.); EcoRI, EcoRI methylase, DNA ligase, and DNA Polymerase I, from New England Biolabs (NEB, Beverly Mass.); and RNase A was obtained from Sigma (St. Louis, Mo.)

Other reagents: EcoRI linkers were obtained from NEB; and nitro blue tetrazolium (NBT), 5-bromo-4-chloro-3-indolyl phosphate (BCIP) 5-bromo-4-chloro-3-indolyl-B-D-galactopyranoside (Xgal) and isopropyl B-D-thiogalactopyranoside (IPTG) were obtained from Sigma.

cDNA synthesis kit and random priming labeling kits are available from Boehringer-Mannheim Biochemical (BMB, Indianapolis, Ind.).

EXAMPLE 1

Preparing cDNA Library

A. Source of ET-NANB virus

Two cynomolgus monkeys (cynos) were intravenously injected with a 10% suspension of a stool pool obtained from a second-passage cyno (cyno #37) infected with a strain of ET-NANB virus isolated from Burma cases whose stools were positive for ET-NANB, as evidenced by binding of 27–34 nm virus-like particles (VLPs) in the stool to immune serum from a known ETNANB patient. The animals developed elevated levels of alanine aminotransferase (ALT) between 24–36 days after inoculation, and one excreted 27–34 nm VLPs in its bile in the pre-acute phase of infection.

The bile duct of each infected animal was cannulated and about 1–3 cc of bile was collected daily. RNA was extracted from one bile specimen (cyno #121) by hot phenol extraction, using a standard RNA isolation procedure. Double-strand cDNA was formed from the isolated RNA by a random primer for first-strand generation, using a cDNA synthesis kit obtained from Boehringer-Mannheim (Indianapolis, Ind.).

B. Cloning the Duplex Fragments

The duplex cDNA fragments were blunt-ended with T4 DNA polymerase under standard conditions (Maniatis, p. 118), then extracted with phenol/chloroform and precipitated with ethanol. The blunt-ended material was ligated with EcoRI linkers under standard conditions (Maniatis, pp. 396–397) and digested with EcoRI to remove redundant linker ends. Non-ligated linkers were removed by sequential isopropanol precipitation.

Lambda gt10 phage vector (Huynh) was obtained from Promega Biotec (Madison, Wis.). This cloning vector has a unique EcoRI cloning site in the phage CI repressor gene. The cDNA fragments from above were introduced into the EcoRI site by mixing 0.5–1.0 µg EcoRI-cleaved gt10, 0.5–3 µl of the above duplex fragments, 0.5 µl 10X ligation buffer, 0.5 µl ligase (200 units), and distilled water to 5 µl. The mixture was incubated overnight at 14° C., followed by in vitro packaging, according to standard methods (Maniatis, pp. 256–268).

The packaged phage were used to infect an E. coli hfl strain, such as strain HG415. Alternatively, E. coli, strain C600 hfl available from Promega Biotec, Madison, Wis., could be used. The percentage of recombinant plaques obtained with insertion of the EcoRI-ended fragments was less than 5% by analysis of 20 random plaques.

The resultant cDNA library was plated and phage were eluted from the selection plates by addition of elution buffer. After DNA extraction from the phage, the DNA was digested with EcoRI to release the heterogeneous insert population, and the DNA fragments were fractionated on agarose to remove phage fragments. The 500–4,000 basepair inserts were isolated and recloned into lambda gt10 as above, and the packaged phage was used to infect E. coli strain HG415. The percentage of successful recombinants was greater than 95%. The phage library was plated on *E. coli* strain HG415, at about 5,000 plaques/plate, on a total of 8 plates.

EXAMPLE 2

Selecting ET-NANB Cloned Fragments

A. CDNA Probes

Duplex cDNA fragments from noninfected and ETNANB-infected cynomolgus monkeys were prepared as in Example 1. The cDNA fragments were radiolabeled by random priming, using a random-priming labeling kit obtained from Boehringer-Mannheim (Indianapolis, Ind.).

B. Clone Selection

The plated CDNA library from Example 1 was transferred to each of two nitrocellulose filters, and the phage DNA was fixed on the filters by baking, according to standard methods (Maniatis, pp. 320323). The duplicate filters were hybridized with either infected-source or control CDNA probes from above. Autoradiographs of the filters were examined to identify library clones which hybridized with radiolabeled CDNA probes from infected source only, i.e., did not hybridize with cDNA probes from the non-infected source. Sixteen such clones, out of a total of about 40,000 clones examined, were identified by this subtraction selection method.

Each of the sixteen clones was picked and replated at low concentration on an agar plate. The clones on each plate were transferred to two nitrocellulose ag duplicate lifts, and examined for hybridization to radiolabeled cDNA probes from infected and noninfected sources, as above. Clones were selected which showed selective binding for infected-source probes (i.e., binding with infected-source probes and substantially no binding with non-infected-source probes). One of the clones which bound selectively to probe from infected source was isolated for further study. The selected vector was identified as lambda gt10-1.1, indicated in FIG. 1.

EXAMPLE 3

ET-NANB Sequence

Clone lambda gt10-1.1 from Example 2 was digested with EcoRI to release the heterologous insert, which was separated from the vector fragments by gel electrophoresis. The electrophoretic mobility of the fragment was consistent with a 1.33 kb fragment. This fragment, which contained EcoRI ends, was inserted into the EcoRI site of a pTZKF1 vector, whose construction and properties are described in co-owned U.S. patent application for "Cloning Vector System and Method for Rare Clone Identification", Ser. No. 125,650, filed Nov. 25, 1987, now abandoned. Briefly, and as illustrated in FIG. 1, this plasmid contains a unique EcoRI site adjacent a T7 polymerase promoter site, and plasmid and phage origins of replication. The sequence immediately adjacent each side of the EcoRI site is known. *E. coli* BB4 bacteria, obtained from Stratagene (La Jolla, Calif., were transformed with the plasmid.

Radiolabeled ET-NANB probe was prepared by excising the 1.33 kb insert from the lambda gt10-1.1 phage in Example 2, separating the fragment by gel electrophoresis, and randomly labeling as above. Bacteria transfected with the above pTZKF1 and containing the desired ET-NANB insert were selected by replica lift and hybridization with the radiolabeled ET-NANB probe, according to methods outlined in Example 2.

One bacterial colony containing a successful recombinant was used for sequencing a portion of the 1.33 kb insert. This isolate, designated pTZKF1 (ET1.1), has been deposited with the American Type Culture Collection, and is identified by ATCC deposit no. 67717. Using a standard dideoxy sequencing procedure, and primers for the sequences flanking the EcoRI site, about 200–250 basepairs of sequence from the 5'-end region and 3'-end region of the insert were obtained. The sequences are given above in Section II. Later sequencing by the same techniques gave the full sequence in both directions, also given above.

EXAMPLE 4

Detecting ET-NANB Sequences cDNA fragment mixtures from the bile of noninfected and ET-NANB-infected cynomolgus monkeys were prepared as above. The cDNA fragments obtained from human stool samples were prepared as follows. Thirty ml of a 10% stool suspension obtained from an individual from Mexico a as infected with ET-NANB as a result of an ET-NANB outbreak, and a similar volume of stool from a healthy, non-infected individual, were layered over g 30% sucrose density gradient cushion, and Centrifuged at 25,000×g for 6 hr in an SW27 rotor, at 15° C. The pelleted material from the infected-source stool contained 27–34 nm VLP particles characteristic of ET-NANB infection in the infected-stool sample. RNA was isolated from the sucrose-gradient pellets in both the infected and non-infected samples, and the isolated RNA was used to produce cDNA fragments as described in Example 1.

The CDNA fragment mixtures from infected and non-infected bile source, and from infected and non-infected human-stool source were each amplified by a novel linker/primer replication method described in co-owned patent application Ser. No. 07/208,512 for "DNA Amplification and Subtraction Technique," filed Jun. 17, 1988. Briefly, the fragments in each sample were blunt-ended with DNA Pol I then extracted with phenol/chloroform and precipitated with ethanol. The blunt-ended material was ligated with linkers having the following sequence (top or 5' sequence has SEQ ID NO.3; bottom or 3' sequence has SEQ ID NO:4):

```
5'-GGAATTCGCGGCCGCTCG-3'

3'-TTCCTTAAGCGCCGGCGAGC-5'
```

The duplex fragments were digested with NruI to remove linker dimers, mixed with a primer having the sequence represented by SEQ ID NO:3, and then heat denatured and cooled to room temperature to form single-strand DNA/primer complexes. The complexes were replicated to form duplex fragments by addition of *Thermus aquaticus* (Taq) polymerase and all four deoxynucleotides. The replication procedures, involving successive strand denaturation, formation of strand/primer complexes, and replication, was repeated 25 times.

Figure 2:
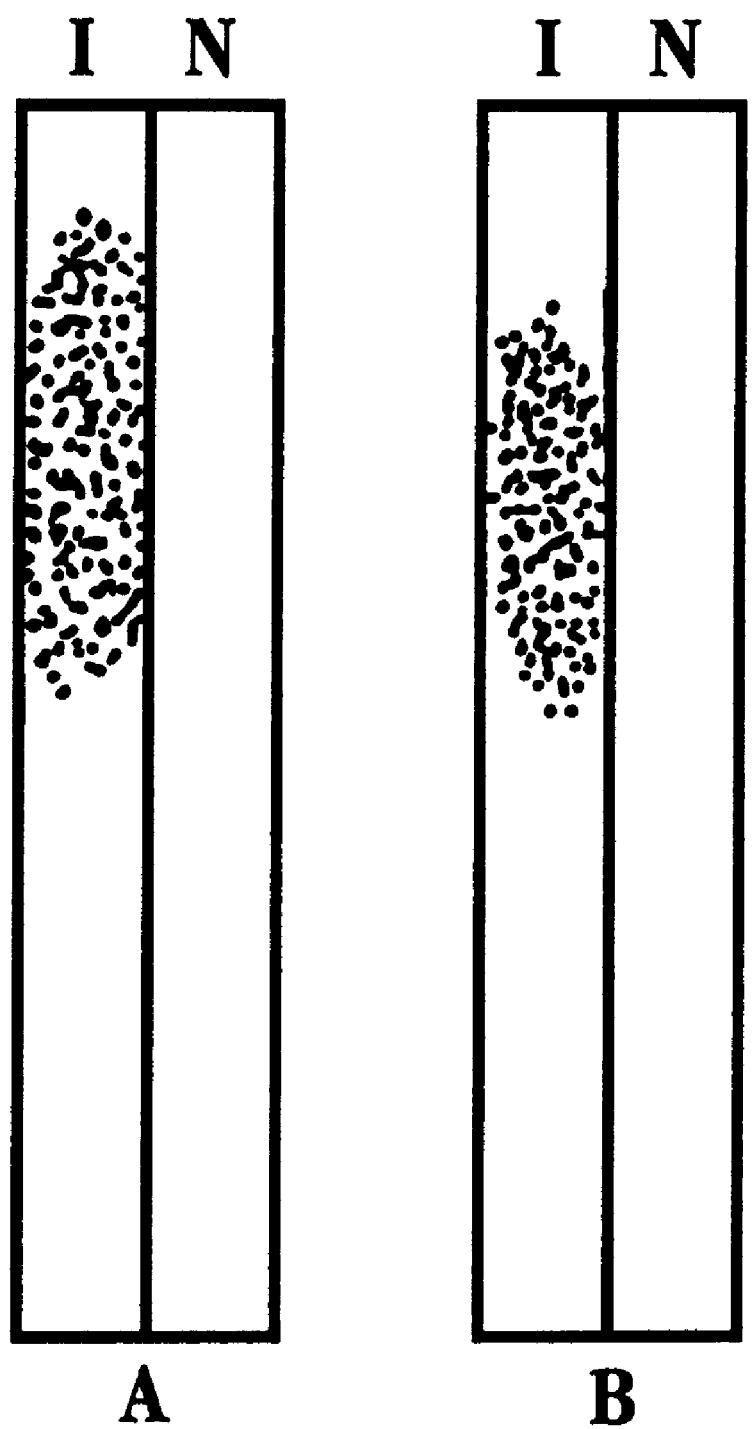
FIGS. 2A–2B are representations of Southern blots in which a radiolabeled ET-NANB probe was hybridized with amplified cDNA fragments prepared from RNA isolated from infected (I) and non-infected (N) bile sources (2A), and from infected (I) and non-infected (N) stool-sample sources (2B).

The amplified cDNA sequences were fractionated by agarose gel electrophoresis, using a 2% agarose matrix. After transfer of the DNA fragments from the agarose gels to nitrocellulose paper, the filters were hybridized to a random-labeled 32p probe prepared by (i) treating the pTZKF1(ET1.1) plasmid from above with EcoRI, (ii) isolating the released 1.33 kb ET-NANB fragment, and (iii) randomly labeling the isolated fragment. The probe hybridization wag performed by conventional Southern blotting methods (Maniatis, pp. 382–389). FIG. 2 shows the hybridization pattern obtained with cDNAs from infected (I) and non-infected (N) bile sources (2A) and from infected (I) and noninfected (N) human stool sources (2B). As seen, the ET-NANB probe hybridized with fragments obtained from both of the infected sources, but was non-homologous to sequences obtained from either of the non-infected sources, thus confirming the specificity of derived sequence.

Southern blots of the radiolabeled 1.33 kb fragment with genomic DNA fragments from both human and cynomolgus-monkey DNA were also prepared. No probe hybridization to either of the genomic fragment mixtures was observed, confirming that the ET-NANB sequence is exogenous to either human or cynomolgus genome.

EXAMPLE 5

Expressing ET-NANB Proteins

A. Preparing ET-NANB Coding Sequences

The pTZKF1(ET1.1) plasmid from Example 2 was digested with EcoRI to release the 1.33 kb ET-NANB insert which was purified from the linearized plasmid by gel electrophoresis. The purified fragment was suspended in a standard digest buffer (0.5M Tris HCl, pH 7.5; 1 mg/ml BSA; 10 mM MnC12) to a concentration of about 1 mg/ml and digested with DNAse I at room temperature for about 5 minutes. These reaction conditions were determined from a prior calibration study, in which the incubation time required to produce predominantly 100–300 basepair fragments was determined. The material was extracted with phenol/chloroform before ethanol precipitation.

The fragments in the digest mixture were blunt-ended and ligated with EcoRI linkers as in Example 1. The resultant fragments were analyzed by electrophoresis (5–10V/cm) on 1.2% agarose gel, using PhiX174/HaeIII and lambda/HindIII size markers. The 100–300 bp fraction was eluted onto NA45 strips (Schleicher and Schuell), which were then placed into 1.5 ml microtubes with eluting solution (1 M NaCl, 50 mM arginine, pH 9.0), and incubated at 67° C. for 30–60 minutes. The eluted DNA was phenol/chloroform extracted and then precipitated with two volumes of ethanol. The pellet was resuspended in 20 µl TE (0.01 M Tris HCl, pH 7.5, 0.001 M EDTA).

B. Cloning in an Expression Vector

Lambda gt11 phage vector (Huynh) was obtained from Promega Biotec (Madison, Wis.). This cloning vector has a unique EcoRI cloning site 53 base pairs upstream from the beta-galactosidase translation termination codon. The genomic fragments from above, provided either directly from coding sequences (Example 5) or after amplification of cDNA (Example 4), were introduced into the EcoRI site by mixing 0.5–1.0 µg EcoRI-cleaved gt11, 0.3–3 µl of the above sized fragments, 0.5 µl 10X ligation buffer (above), 0.5 µl ligase (200 units), and distilled water to 5 µl. The mixture was incubated overnight at 14° C., followed by in vitro packaging, according to standard methods (Maniatis, pp. 256–268).

The packaged phage were used to infect E. coli strain KM392, obtained from Dr. Kevin Moore, DNAX (Palo Alto, Calif.). Alternatively, E. Coli strain Y1090, available from the American Type Culture Collection (ATCC #37197), could be used. The infected bacteria were plated and the resultant colonies were checked for loss of beta-galactosidase activity-(clear plaques) in the presence of X-gal using a standard X-gal substrate plaque assay method (Maniatis). About 50% of the phage plaques showed loss of beta-galactosidase enzyme activity (recombinants).

C. Screening for ET-NANB Recombinant Proteins

ET-NANB convalescent antiserum was obtained from patients infected during documented ET-NANB outbreaks in Mexico, Borneo, Pakistan, Somalia, and Burma. The sera were immunoreactive with VLPs in stool specimens from each of several other patients with ET-NANB hepatitis.

A lawn of E. coli KM392 cells infected with about 104 pfu of the phage stock from above was prepared on a 150 mm plate and incubated, inverted, for 5–8 hours at 37° C. The lawn was overlaid with a nitrocellulose sheet, causing transfer of expressed ETNANB recombinant protein from the plaques to the paper. The plate and filter were indexed for matching corresponding plate and filter positions.

The filter was washed twice in TBST buffer (10 mM Tris, pH 8.0, 150 mM NaCl, 0.05% TWEEN® 20, a polyoxyethylene (20) sorbitan), blocked with AIB (TBST buffer with 1% gelatin), washed again in TEST, and incubated overnight after addition of antiserum (diluted to 1:50 in AIB, 12–15 ml/plate). The sheet was washed twice in TBST and then contacted with enzyme-labeled anti-human antibody to attach the labeled antibody at filter sites containing antigen recognized by the antiserum. After a final washing, the filter was developed in a substrate medium containing 33 µl NBT (50 mg/ml stock solution maintained at 4° C.) mixed with 16 µl BCIP (50 mg/ml stock solution maintained at 4° C.) in 5 ml of alkaline phosphatase buffer (100 mM Tris, 9.5, 100 mM NaCl, 5 mM MgC12). Purple color appeared at points of antigen production, as recognized by the antiserum.

D. Screening Plating

The areas of antigen production determined in the previous step were replated at about 100–200 pfu on an 82 mm plate. The above steps, beginning with a 5–8 hour incubation, through NBT-BCIP development, were repeated in order to plaque purify phage secreting an antigen capable of reacting with the ET-NANB antibody. The identified plaques were picked and eluted in phage buffer (Maniatis, p. 443).

E. Epitope Identification

A series of subclones derived from the original PTZKF1 (ET1.1) plasmid from Example 2 were isolated using the same techniques described above. Each of these five subclones were immunoreactive with a pool of anti-ET antisera noted in C. The subclones contained short sequences from the "reverse" sequence set forth previously. The beginning and ending points of the sequences in the subclones (relative to the full "reverse" sequence), are identified in the table below.

TABLE 1

| Subclone | Position in "Reverse" Sequence 5'-end | 3'-end |
|---|---|---|
| Y1 | 522 | 643 |
| Y2 | 594 | 667 |
| Y3 | 508 | 665 |
| Y4 | 558 | 752 |
| Y5 | 545 | 665 |

Since all of the gene sequences identified in the table must contain the coding sequence for the epitope, it is apparent that the coding sequence for the epitope falls in the region between nucleotide 594 (5'-end) and 643 (3'-end). Genetic sequences equivalent to and complementary to this relatively short sequence are therefore particularly preferred aspects of the present invention, as are peptides produced using this coding region.

A second series of clones identifying an altogether different epitope was isolated with only Mexican serum.

TABLE 2

| Subclone | Position in "Forward" Sequence | |
|---|---|---|
| | 5' end | 3' end |
| ET 2-2 | 2 | 193 |
| ET 8-3 | 2 | 135 |
| ET 9-1 | 2 | 109 |
| ET 13-1 | 2 | 101 |

The coding system for this epitope falls between nucleotide 2 (S-end) and 101 (3-end). Genetic sequences related to this short sequence are therefore also preferred, as are peptides produced using this coding region.

Two particularly preferred subclones for use in preparing polypeptides containing epitopes specific for HEV are the 406.3-2 and 406.4-2 clones whose sequences are set forth above. These sequences were isolated from an amplified cDNA library derived from a Mexican stool. Using the techniques described in this section, polypeptides expressed by these clones have been tested for immunoreactivity against a number of different human HEV-positive sera obtained from sources around the world. As shown in Table 3 below, 8 sera immunoreactive with the polypeptide expressed by the 406.4-2, and 6 sera immunoreacted with polypeptide expressed by the 406.3-2 clone.

For comparison, the Table also shows reactivity of the various human sera with the Y2 clone identified in Table 1 above. Only one of the sera reacted with the polypeptide expressed by this clone. No immunoreactivity was seen for normal expression products of the gt11 vector.

TABLE 3

Immunoreactivity of HEV Recombinant Proteins: Human Sera

| Sera | Source | Stage[1] | 406.3-2 | 406.4-2 | Y2 | λgt11 |
|---|---|---|---|---|---|---|
| FVH-21 | Burma | A | – | – | – | – |
| FVH-8 | Burma | A | – | + | + | – |
| SOM-19 | Somalia | A | + | + | – | – |
| SOM-20 | Somalia | A | + | + | – | – |
| IM-35 | Borneo | A | + | + | – | – |
| IM-36 | Borneo | A | – | – | – | – |
| PAK-1 | Pakistan | A | + | + | – | – |
| FFI-4 | Mexico | A | + | + | – | – |
| FFI-125 | Mexico | A | – | + | – | – |
| F 387 IC | Mexico | C | + | + | ND | – |
| Normal | U.S.A. | – | – | – | – | – |

[1]A = acute;
[1]C = convalescent

While the invention has been described with reference to particular embodiments, methods, construction and use, it will be apparent to those skilled in the art that various changes and modifications can be made without departing from the invention.

We claim:

1. An isolated DNA comprising the genome of an enterically transmitted nonA/nonB (ET-NANB) viral hepatitis agent (i) containing the nucleotide sequence identified by SEQ ID NO:1 or (ii) containing a region which hybridizes to the nucleotide sequence identified by SEQ ID NO:1, and which remains hybridized under the following wash conditions: 2× SSC, 0.1% SDS, room temperature, twice for 30 minutes each, then 2× SSC, room temperature, twice for 10 minutes each; or a fragment of such isolated DNA, said fragment comprising a nucleotide residue sequence found only in an ET-NANB viral hepatitis agent.

2. An isolated DNA comprising the genome of an enterically transmitted nonA/nonB (ET-NANB) viral hepatitis agent (i) containing the nucleotide sequence identified by SEQ ID NO:1 or (ii) containing a region which hybridizes to the nucleotide sequence identified by SEQ ID NO:1, and which remains hybridized under the following wash conditions: 2× SSC, 0.1% SDS, room temperature, twice for 30 minutes each, then 2× SSC, room temperature, twice for 10 minutes each; or a fragment of such isolated DNA, said fragment (i) being capable of selectively hybridizing to said genome, and (ii) having a length of at least 12 nucleotides.

3. The fragment of claim 2, wherein said fragment has a length of at least 14 nucleotides.

4. The fragment of claim 3, wherein said fragment has a length of at least 20 nucleotides.

5. The fragment of claim 4, wherein said fragment has a length of at least 30 nucleotides.

6. The fragment of claim 5, wherein said fragment has a length of at least 50 nucleotides.

* * * * *